(12) United States Patent
Gavai et al.

(10) Patent No.: US 8,822,454 B2
(45) Date of Patent: *Sep. 2, 2014

(54) BISFLUOROALKYL-1,4-BENZODIAZEPINONE COMPOUNDS

(71) Applicant: Bristol-Myers Squibb Company, Princeton, NJ (US)

(72) Inventors: Ashvinikumar V. Gavai, Princeton Junction, NJ (US); Claude A. Quesnelle, Skillman, NJ (US); Soong-Hoon Kim, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,896

(22) Filed: Dec. 9, 2013

(65) Prior Publication Data

US 2014/0100365 A1   Apr. 10, 2014

Related U.S. Application Data

(63) Continuation of application No. 13/426,730, filed on Mar. 22, 2012, now Pat. No. 8,629,136.

(60) Provisional application No. 61/466,238, filed on Mar. 22, 2011.

(51) Int. Cl.
| | | |
|---|---|---|
| C07D 243/24 | (2006.01) | |
| A61K 31/5513 | (2006.01) | |
| A61K 31/337 | (2006.01) | |
| A61K 31/138 | (2006.01) | |
| A61K 45/06 | (2006.01) | |
| A61K 31/555 | (2006.01) | |
| A61K 31/573 | (2006.01) | |

(52) U.S. Cl.
CPC ............ C07D 243/24 (2013.01); A61K 31/337 (2013.01); A61K 31/138 (2013.01); A61K 45/06 (2013.01); A61K 31/555 (2013.01); A61K 31/5513 (2013.01); A61K 31/573 (2013.01)
USPC .......................................... 514/221; 540/509

(58) Field of Classification Search
USPC .......................................... 540/509; 514/221
See application file for complete search history.

(56) References Cited

U.S. PATENT DOCUMENTS

| | | | |
|---|---|---|---|
| 5,324,726 A | 6/1994 | Bock et al. | |
| 5,852,010 A | 12/1998 | Graham et al. | |
| 5,998,407 A | 12/1999 | Graham et al. | |
| 6,331,408 B1 | 12/2001 | Zaczek et al. | |
| 6,495,540 B2 | 12/2002 | Thompson | |
| 6,503,901 B1 | 1/2003 | Thompson et al. | |
| 6,503,902 B2 | 1/2003 | Olson et al. | |
| 6,509,333 B2 | 1/2003 | Olson | |
| 6,525,044 B2 | 2/2003 | Olson et al. | |
| 6,544,978 B2 | 4/2003 | Wu et al. | |
| 6,632,812 B2 | 10/2003 | Han et al. | |
| 6,653,303 B1 | 11/2003 | Wu et al. | |
| 6,713,476 B2 | 3/2004 | Yang et al. | |
| 6,737,038 B1 | 5/2004 | Zaczek et al. | |
| 6,756,511 B2 | 6/2004 | Castro Pineiro et al. | |
| 6,759,404 B2 | 7/2004 | Olson et al. | |
| 6,794,381 B1 | 9/2004 | Olson et al. | |
| 6,878,363 B2 | 4/2005 | Zaczek et al. | |
| 6,900,199 B2 | 5/2005 | Han et al. | |
| 6,958,329 B2 | 10/2005 | Olson | |
| 6,960,576 B2 | 11/2005 | Olson et al. | |
| 6,962,913 B2 | 11/2005 | Olson et al. | |
| 6,984,626 B2 | 1/2006 | Nadin et al. | |
| 7,001,901 B2 | 2/2006 | Yang | |

(Continued)

FOREIGN PATENT DOCUMENTS

| | | |
|---|---|---|
| WO | WO 97/36879 | 10/1997 |
| WO | WO 01/74796 | 10/2001 |
| WO | WO 01/90084 | 11/2001 |
| WO | WO 2007/067048 | 6/2007 |
| WO | WO 2009/023453 | 2/2009 |

OTHER PUBLICATIONS

Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.

(Continued)

Primary Examiner — Bruck Kifle
(74) Attorney, Agent, or Firm — Gary D. Greenblatt

(57) ABSTRACT

Disclosed are compounds of Formula (I) or prodrugs thereof;

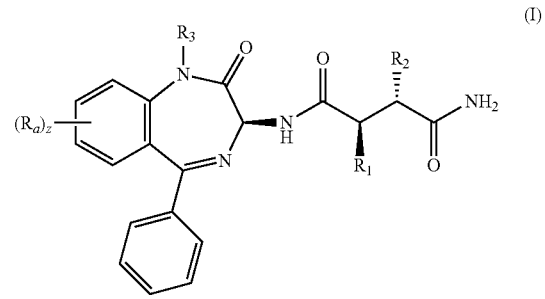

wherein: $R_1$ is —$CH_2CF_3$ or —$CH_2CH_2CF_3$; $R_2$ is —$CH_2CF_3$, —$CH_2CH_2CF_3$, or —$CH_2CH_2CH_2CF_3$; $R_3$ is H or —$CH_3$; each $R_a$ is independently F, Cl, —CN, —$OCH_3$, and/or —$NHCH_2CH_2OCH_3$; and z is zero, 1, or 2. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer.

6 Claims, 16 Drawing Sheets

(56) References Cited

U.S. PATENT DOCUMENTS

| | | | |
|---|---|---|---|
| 7,053,081 | B2 | 5/2006 | Olson et al. |
| 7,053,084 | B1 | 5/2006 | Olson |
| 7,101,870 | B2 | 9/2006 | Olson et al. |
| 7,105,509 | B2 | 9/2006 | Castro Pineiro et al. |
| 7,112,583 | B2 | 9/2006 | Olson et al. |
| 7,125,866 | B1 | 10/2006 | Glick et al. |
| 7,153,491 | B2 | 12/2006 | Zaczek et al. |
| 7,160,875 | B2 | 1/2007 | Flohr et al. |
| 7,276,495 | B2 | 10/2007 | Han et al. |
| 7,276,496 | B2 | 10/2007 | Olson et al. |
| 7,304,049 | B2 | 12/2007 | Olson |
| 7,304,055 | B2 | 12/2007 | Olson et al. |
| 7,304,056 | B2 | 12/2007 | Olson et al. |
| 7,342,008 | B2 | 3/2008 | Olson et al. |
| 7,354,914 | B2 | 4/2008 | Olson |
| 7,375,099 | B2 | 5/2008 | Galley et al. |
| 7,390,802 | B2 | 6/2008 | Han et al. |
| 7,390,896 | B2 | 6/2008 | Olson et al. |
| 7,414,049 | B2 | 8/2008 | Flohr et al. |
| 7,423,033 | B2 | 9/2008 | Olson et al. |
| 7,425,551 | B2 | 9/2008 | Flohr et al. |
| 7,456,172 | B2 | 11/2008 | Olson |
| 7,456,278 | B2 | 11/2008 | Olson |
| 7,498,324 | B2 | 3/2009 | Han et al. |
| 7,528,249 | B2 | 5/2009 | Olson et al. |
| 7,582,624 | B2 | 9/2009 | Carter et al. |
| 7,655,647 | B2 | 2/2010 | Han et al. |
| 7,718,795 | B2 | 5/2010 | Olson |
| 2007/0185094 | A1 | 8/2007 | Lattmann et al. |
| 2008/0058316 | A1 | 3/2008 | Eberhart et al. |
| 2009/0181944 | A1 | 7/2009 | Boylan et al. |
| 2011/0178046 | A1 | 7/2011 | Ross et al. |
| 2012/0225860 | A1 | 9/2012 | Boylan et al. |

OTHER PUBLICATIONS

Seiffert, D., et al., "Presenilin-1 and -2 Are Molecular Targets for gamma-Secretase Inhibitors," The Journal of Biological Chemistry, vol. 275, No. 44, pp. 34086-34091 (2000).

Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).

Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

Meredith, Jere, "Characterization of APP Activity and Notch Toxicity with gamma-Secretase Inhibitors," 8th International AD/PD Meeting, Salzberg, Austria, Mar. 17, 2007.

Prasad, C.V.C., et al., "Discovery of (S)-2-((S)-2(3,5-difluorophenyl)-2-hydroxyacetamido)-$N$-((S,Z)-3-methyl-4-oxo-4,5-dihydro-3$H$-benzo[$d$][1,2]diazepin-5-yl)propanamide (BMS-433796): A gamma-secretase inhibitor with a beta lowering activity in a transgenic mouse model of Alzheimer's disease," Bioorganic & Medicinal Chemistry Letters 17 pp. 4006-4011 (2007).

Jun, H.T., et al., "Top Notch Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

International Search Report mailed May 11, 2012; received May 22, 2012.

BISFLUOROALKYL-1,4-BENZODIAZEPINONE COMPOUNDS

The present invention generally relates to benzodiazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell* 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I.-M. et al., *Cancer Research*, 67:1879-1882 (2007); Yamaguchi, N. et al., *Cancer Research*, 68:1881-1888 (2008); Miele, L., *Expert Review Anti-cancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein. The reference does not disclose the use of these compounds in the treatment of proliferative diseases such as cancer.

Applicants have found potent compounds that have activity as Notch inhibitors and have sufficient metabolic stability to provide efficacious levels of drug exposure upon intravenous or oral administration. These compounds are provided to be useful as pharmaceuticals with desirable stability, bioavailability, therapeutic index, and toxicity values that are important to their drugability.

SUMMARY OF THE INVENTION

The present invention fills the foregoing need by providing bis(fluoroalkyl)-1,4-benzodiazepinone compounds that are useful as selective inhibitors of Notch signaling pathway, including prodrugs thereof.

The present invention also provides pharmaceutical compositions comprising a pharmaceutically acceptable carrier; and at least one compound of Formula (I) or prodrugs thereof.

The present invention also provides a method of treating a disease or disorder associated with the activity of the Notch receptor, the method comprising administering to a mammalian patient a compound of Formula (I) or pharmaceutically acceptable prodrugs thereof.

The present invention also provides processes and intermediates for making the compounds of Formula (I) or prodrugs thereof.

The present invention also provides the compounds of Formula (I), or prodrugs thereof, for use in therapy.

The present invention also provides the use of the compounds of Formula (I), or prodrugs thereof, for the manufacture of a medicament for the treatment of cancer.

The compounds of Formula (I) and compositions comprising the compounds are Notch inhibitors may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

BRIEF DESCRIPTION OF THE DRAWINGS

The invention is illustrated by reference to the accompanying drawings described below.

Figure 8:
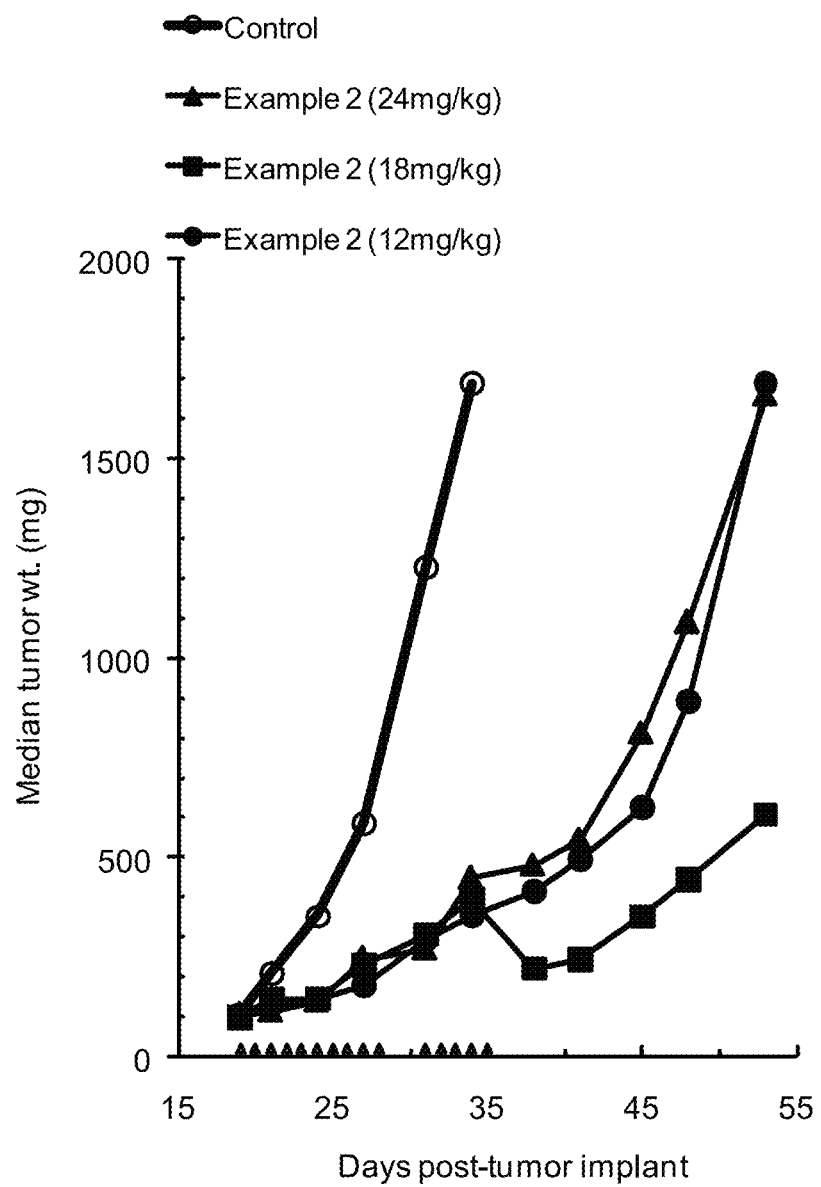

FIG. 8 shows the in vivo antitumor activity of Example 2 in human breast carcinoma cell line MDA-MB-157. Each symbol represents the median tumor burden of a group of 8 mice. (○) control; (▲) Example 2, 24 mg/kg; (■) Example 2, 18 mg/kg; (■) Example 2, 12 mg/kg.

Figure 9:
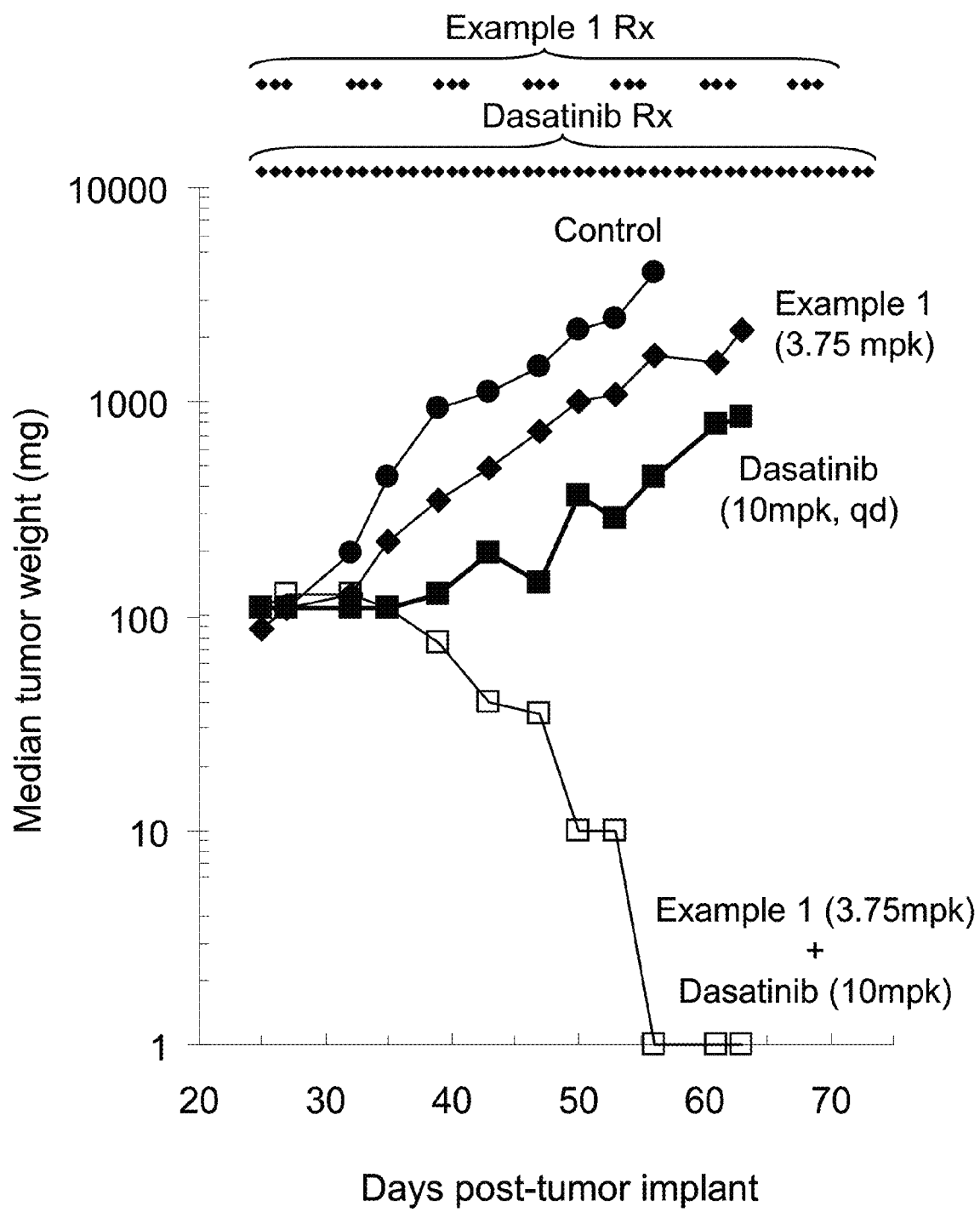

FIG. 9 shows the synergistic antitumor efficacy by combined chemotherapy with Example 1 and dasatinib in the ALL-SIL T-cell lymphoblastic leukemia. Each symbol represents the median tumor burden of a group of 8 mice. (●) control; (♦) Example 1, 3.75 mg/kg/adm, QD×3, weekly for 7 weeks, PO; (■) dasatinib, 10 mg/kg/adm, QD×49, PO; (□) Example 1, 3.75 mg/kg/adm, QD×3, weekly for 7 weeks, PO+dasatinib 10 mg/kg/adm, QD×49, PO. When administered on the same day, the two agents were given more or less simultaneously (Example 1 preceded dasatinib by less than 1 hr).

Figure 10:
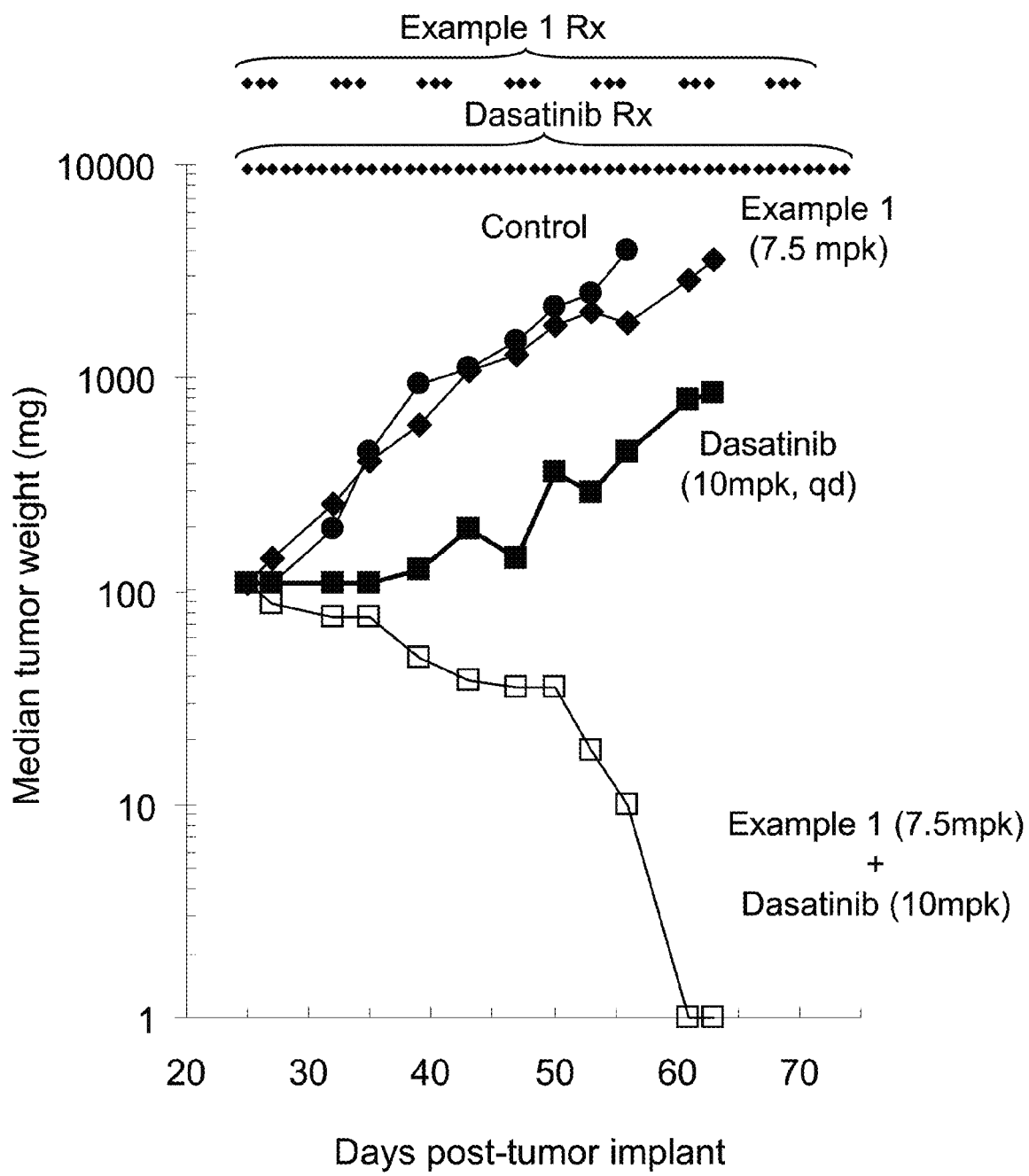

FIG. 10 shows the synergistic antitumor efficacy by combined chemotherapy with Example 1 and dasatinib in the ALL-SIL T-cell lymphoblastic leukemia. Each symbol represents the median tumor burden of a group of 8 mice. (●) control; (♦) Example 1, 7.5 mg/kg/adm QD×3, weekly for 7 weeks, PO; (■) dasatinib, 10 mg/kg/adm, QD×49, PO; (□) Example 1, 7.5 mg/kg/adm, QD×3, weekly for 7 weeks, PO+dasatinib 10 mg/kg/adm, QD×49, PO. When administered on the same day, the two agents were given more or less simultaneously (Example 1 preceded dasatinib by less than 1 hr).

Figure 11:
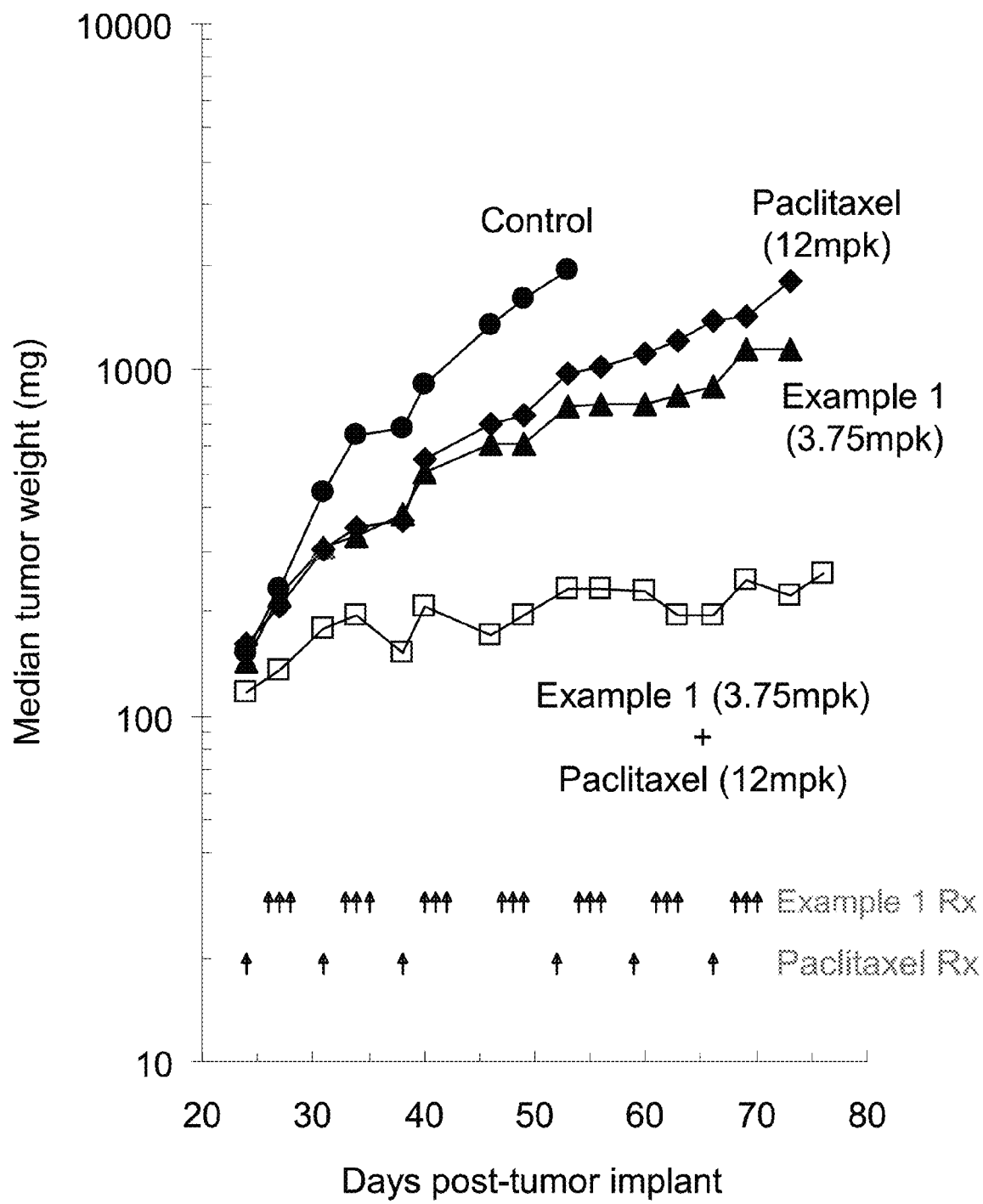

FIG. 11 shows the synergistic antitumor efficacy by combined chemotherapy with Example 1 and Paclitaxel in the MDA-MB-468 Human Breast Carcinoma. Each symbol represents the median tumor burden of a group of 8 mice. (●) control; (♦) Paclitaxel, 12 mg/kg/adm, Q7D×6, IV; (▲) Example 1, 3.75 mg/kg/adm, QD×3, weekly for 7 weeks, PO; (□) Combination of Example 1 and Paclitaxel.

Figure 12:
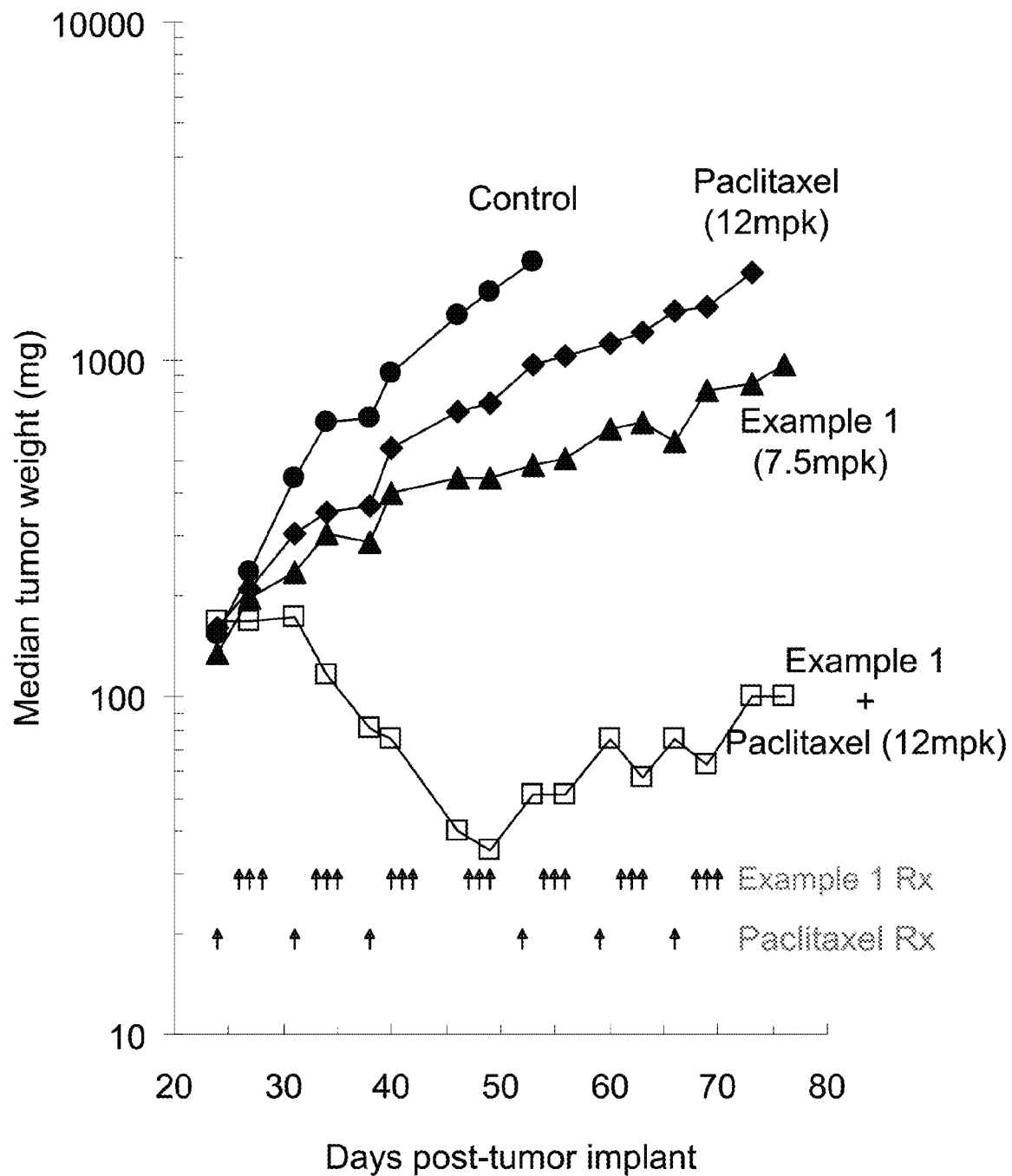

FIG. 12 shows the synergistic antitumor efficacy by combined chemotherapy with Example 1 and Paclitaxel in the MDA-MB-468 Human Breast Carcinoma. Each symbol represents the median tumor burden of a group of 8 mice. (●) control; (♦) Paclitaxel, 12 mg/kg/adm, Q7D×6, IV; (♦) Example 1, 7.5 mg/kg/adm, QD×3, weekly for 7 weeks, PO; (□) Combination of Example 1 and Paclitaxel.

Figure 13:
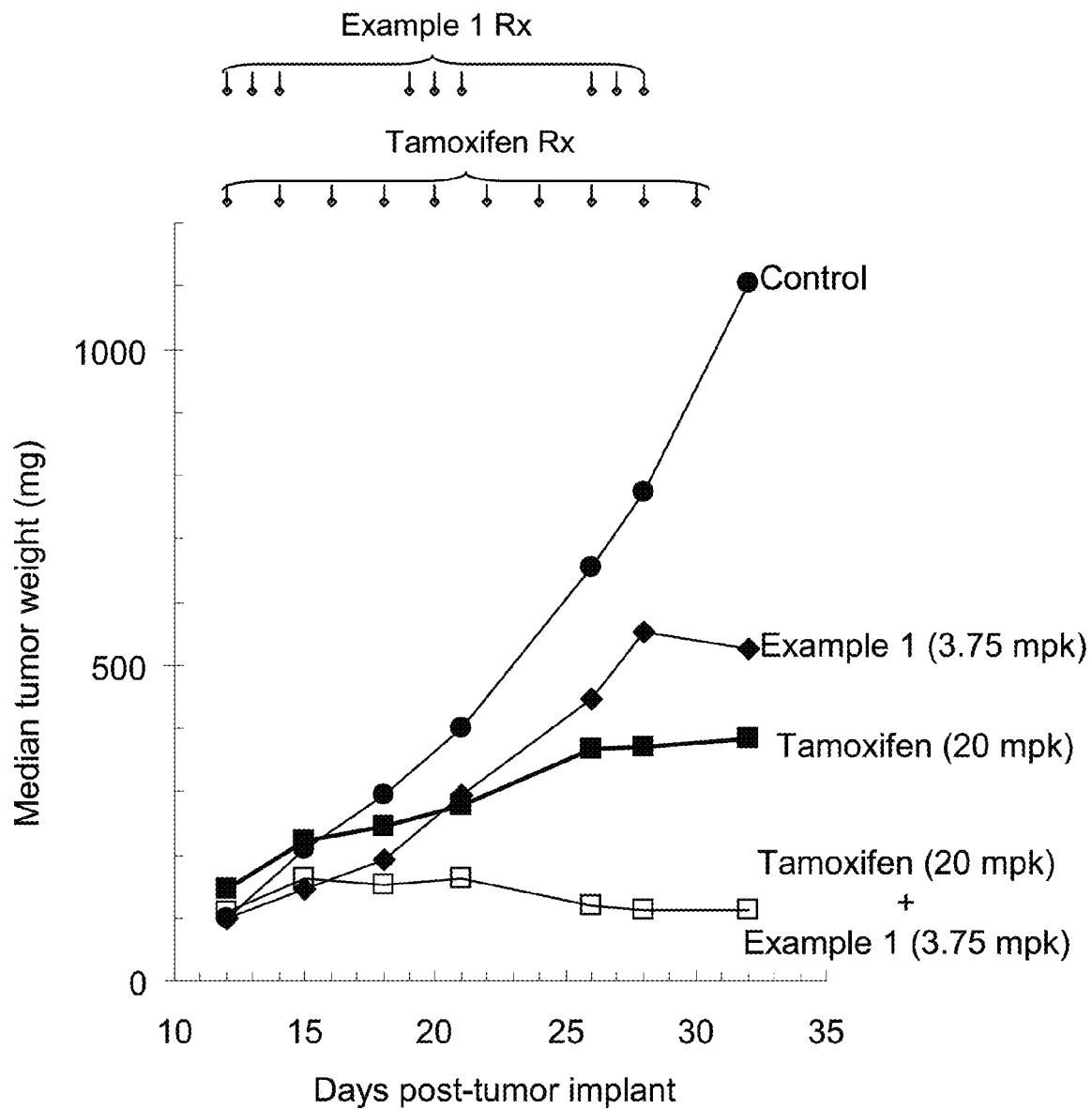

FIG. 13 shows the synergistic antitumor efficacy by combined chemotherapy with Example 1 and Tamoxifen in the MCF7 Human Breast Carcinoma. Each symbol represents the median tumor burden of a group of 8 mice. (●) control; (■) Tamoxifen, 20 mg/kg/adm, Q2D×12, IP; (♦) Example 1, 3.75 mg/kg/adm, QD×3, weekly for 3 weeks, PO; (□) Combination of Example 1 and Tamoxifen.

Figure 14:
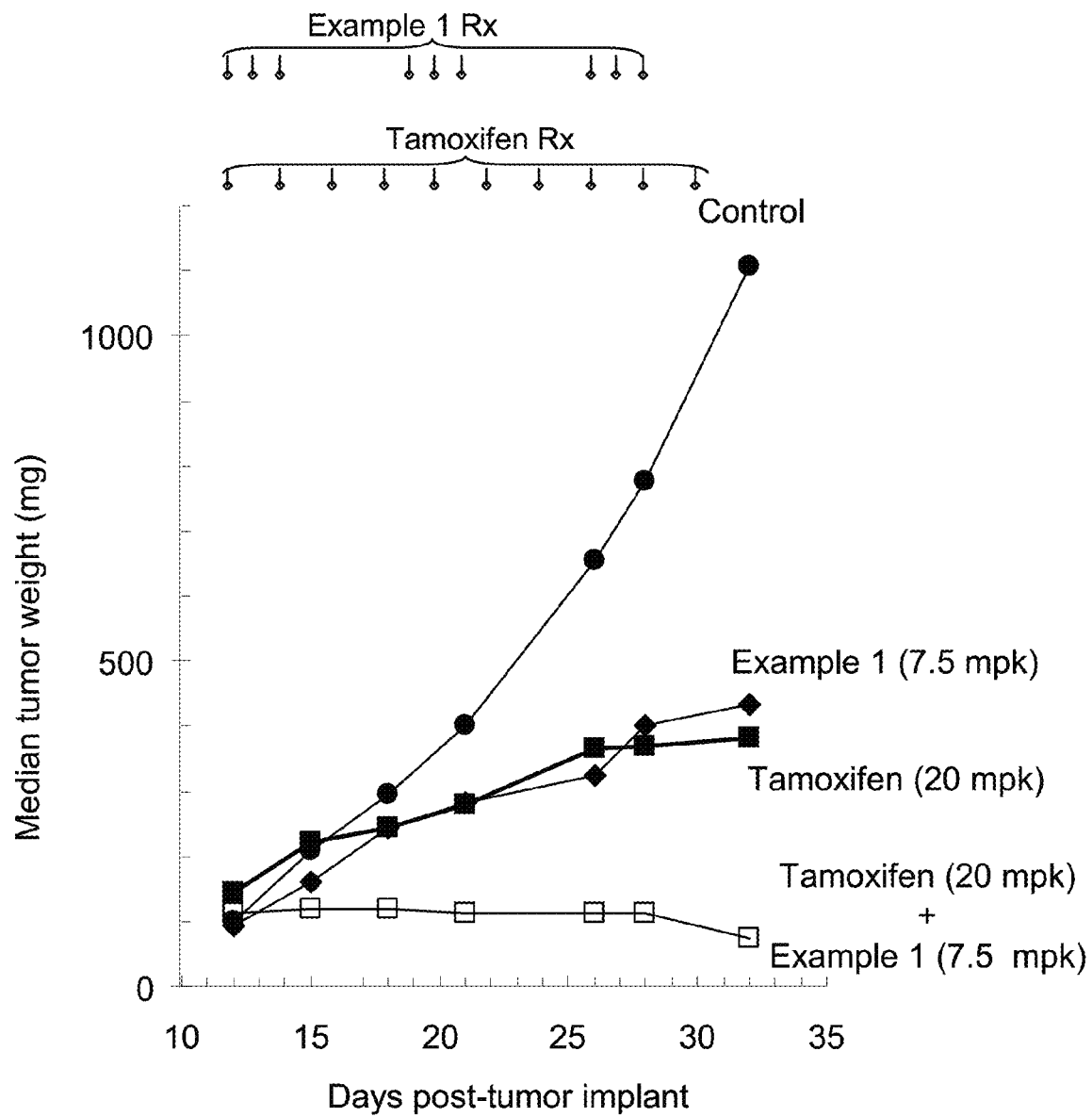

FIG. 14 shows the synergistic antitumor efficacy by combined chemotherapy with Example 1 and Tamoxifen in the MCF7 Human Breast Carcinoma. Each symbol represents the median tumor burden of a group of 8 mice. (●) control; (■) Tamoxifen, 20 mg/kg/adm, Q2D×12, IP; (♦) Example 1, 7.5 mg/kg/adm, QD×3, weekly for 3 weeks, PO; (□) Combination of Example 1 and Tamoxifen.

Figure 15:
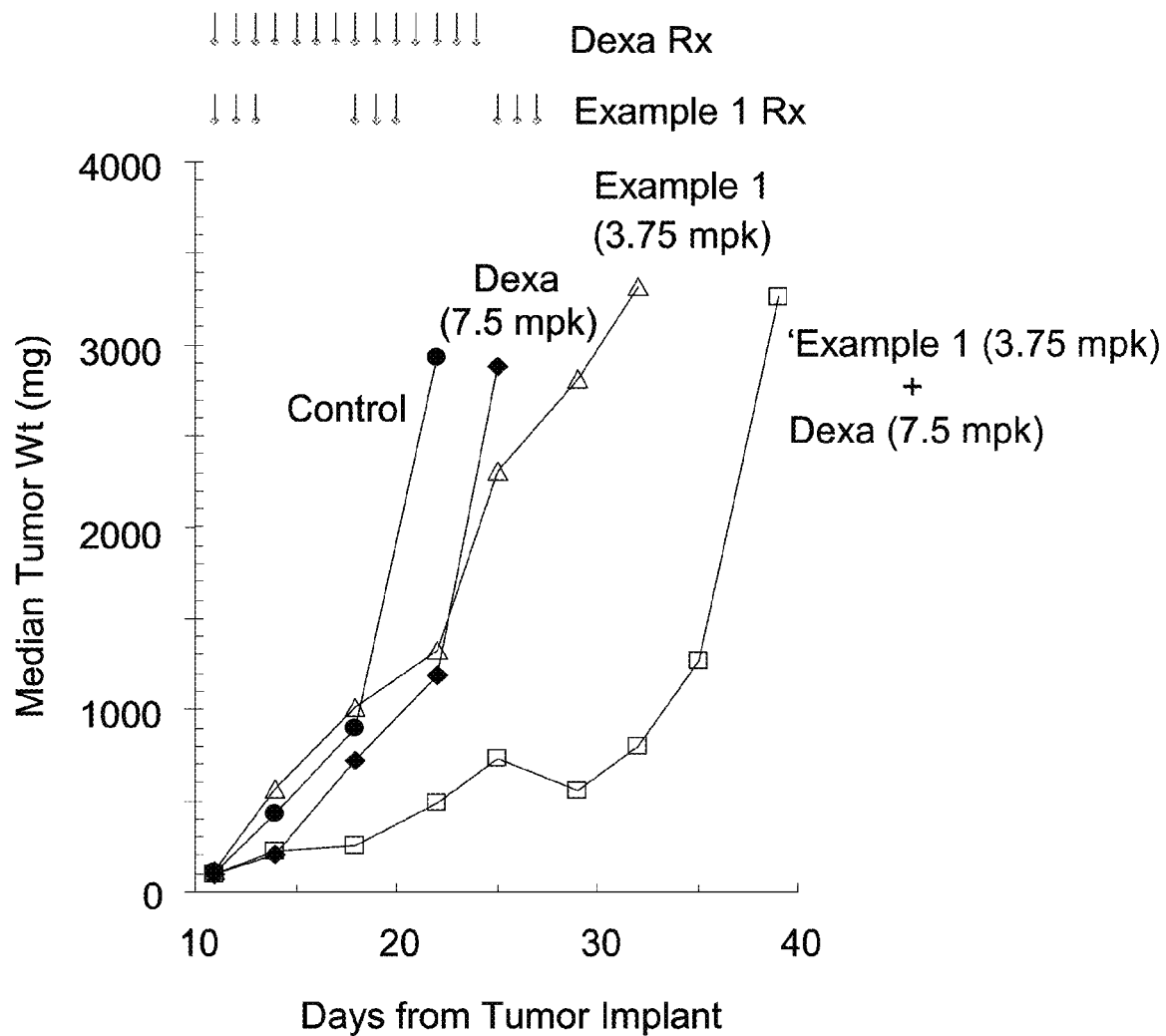

FIG. 15 shows the synergistic antitumor efficacy by combined chemotherapy with Example 1 and dexamethasone (Dexa) in human T-ALL leukemia xenografts HPB-ALL. Each symbol represents the median tumor burden of a group of 6-8 mice. (●) control; (♦) dexamethasone, 7.5 mg/kg/adm, QD×14, IP; (Δ) Example 1, 3.75 mg/kg/adm, QD×3, weekly for 3 weeks, PO; (□) Combination of Example 1 and dexamethasone.

Figure 16:
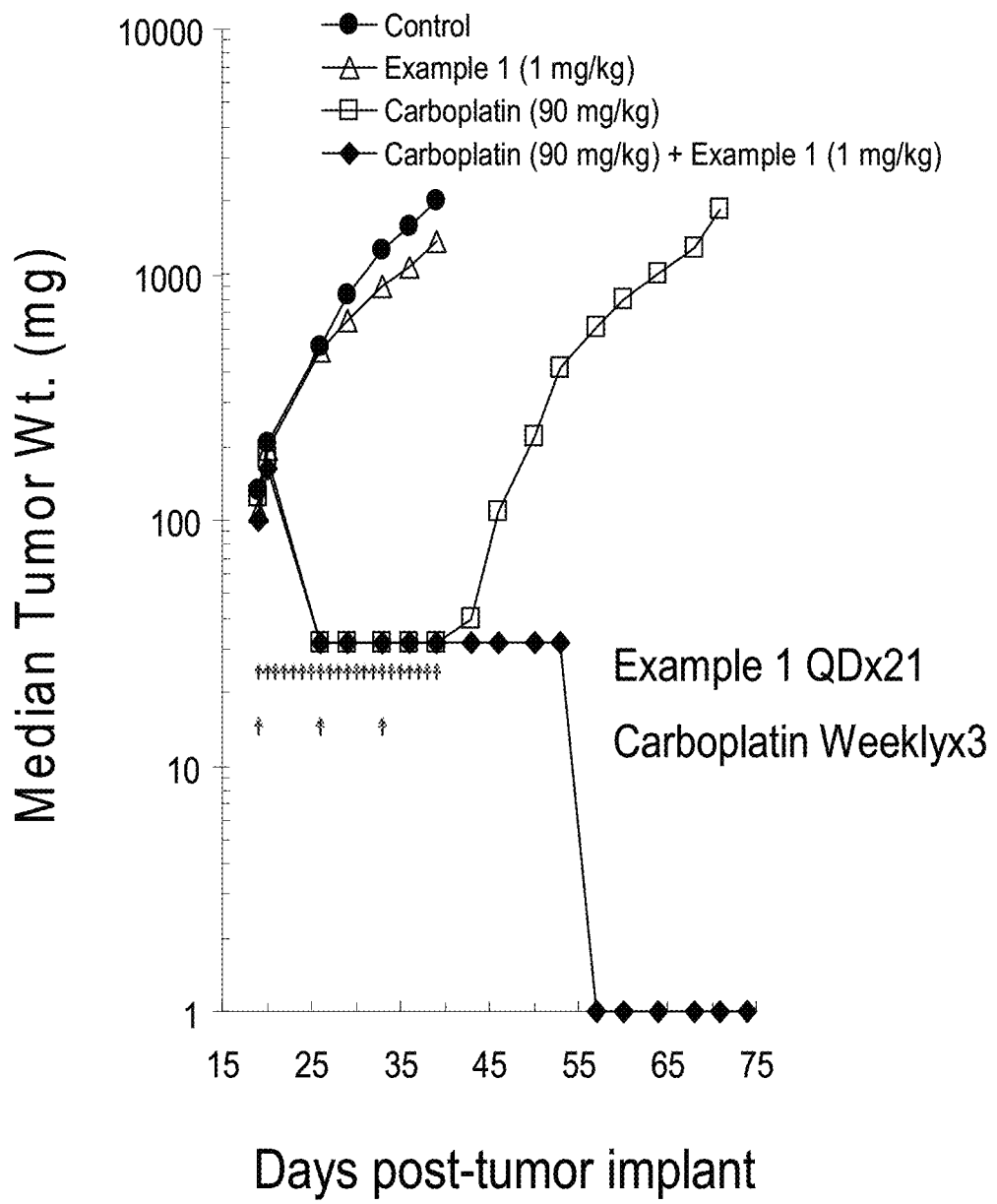

FIG. 16 shows the synergistic antitumor efficacy by combined chemotherapy with Example 1 and carboplatin in PA-1 human ovarian teratocarcinoma. Each symbol represents the median tumor burden of a group of 8 mice. (●) control; (□) carboplatin, 90 mg/kg/adm, Q7D×3, IV; (Δ) Example 1, 1 mg/kg/adm, QD×21, PO; (♦) Combination of Example 1 and carboplatin.

DETAILED DESCRIPTION

The first aspect of the present invention provides compounds of Formula (I):

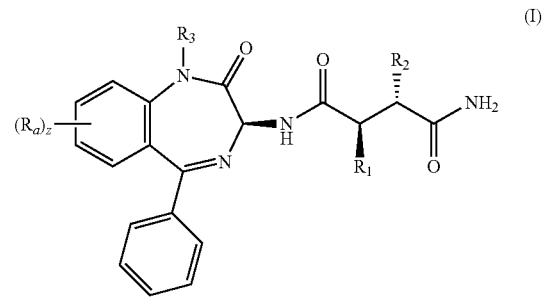

or prodrugs thereof; wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
z is zero, 1, or 2.

One embodiment provides a compound of Formula (I) or prodrugs thereof, wherein $R_1$ is —$CH_2CF_3$; and $R_2$, $R_3$, $R_a$, and z are defined in the first aspect. Included in this embodiment are compounds in which $R_2$ is —$CH_2CF_3$ or —$CH_2CH_2CF_3$.

One embodiment provides a compound of Formula (I) or prodrugs thereof, wherein $R_1$ is —$CH_2CH_2CF_3$; and $R_2$, $R_3$, $R_a$, and z are defined in the first aspect. Included in this embodiment are compounds in which $R_2$ is —$CH_2CF_3$ or —$CH_2CH_2CF_3$.

One embodiment provides a compound of Formula (I) or prodrugs thereof, wherein $R_2$ is —$CH_2CF_3$; and $R_1$, $R_3$, $R_a$, and z are defined in the first aspect. Included in this embodiment are compounds in which $R_1$ is —$CH_2CH_2CF_3$.

One embodiment provides a compound of Formula (I) or prodrugs thereof, wherein $R_2$ is —$CH_2CH_2CF_3$; and $R_1$, $R_3$, $R_a$, and z are defined in the first aspect. Included in this embodiment are compounds in which $R_1$ is —$CH_2CH_2CF_3$.

One embodiment provides a compound of Formula (I) or prodrugs thereof, wherein $R_2$ is —$CH_2CH_2CH_2CF_3$; and $R_1$, $R_3$, $R_a$, and z are defined in the first aspect. Included in this embodiment are compounds in which $R_1$ is —$CH_2CH_2CF_3$.

One embodiment provides a compound of Formula (I) or prodrugs thereof, wherein $R_3$ is H; and $R_1$, $R_2$, $R_a$, and z are defined in the first aspect. Included in this embodiment are compounds in which $R_1$ is deuterium (D) or tritium (T). Also included in this embodiment are compounds in which $R_1$ is —$CH_2CH_2CF_3$ and $R_2$ is —$CH_2CH_2CF_3$.

One embodiment provides a compound of Formula (I) or prodrugs thereof, wherein $R_3$ is —$CH_3$; and $R_1$, $R_2$, $R_a$, and z are defined in the first aspect. $R_3$ includes methyl groups in which one or more hydrogen atoms are isotopically substituted with deuterium (D) and/or tritium (T). In one example of this embodiment, $R_3$ is —$CD_3$. Also included in this embodiment are compounds in which $R_1$ is —$CH_2CH_2CF_3$ and $R_2$ is —$CH_2CH_2CF_3$.

One embodiment provides a compound of Formula (I) or prodrugs thereof, wherein z is 2 and each $R_a$ is independently F, Cl, —CN, —$OCH_3$, and/or —$NHCH_2CH_2OCH_3$; and $R_1$, $R_2$, and $R_3$ are defined in the first aspect. Included in this embodiment are compounds in which $R_1$ is —$CH_2CH_2CF_3$ and $R_2$ is —$CH_2CH_2CF_3$.

One embodiment provides a compound of Formula (I) or prodrugs thereof, wherein z is 1 and $R_a$ is F, Cl, —CN, —$OCH_3$, or —$NHCH_2CH_2OCH_3$; and $R_1$, $R_2$, and $R_3$ are defined in the first aspect. Included in this embodiment are compounds in which $R_1$ is —$CH_2CH_2CF_3$ and $R_2$ is —$CH_2CH_2CF_3$.

One embodiment provides a compound of Formula (I) or prodrugs thereof, wherein z is zero; and $R_1$, $R_2$, and $R_3$ are defined in the first aspect. Included in this embodiment are compounds in which $R_1$ is —$CH_2CH_2CF_3$ and $R_2$ is —$CH_2CF_3$ or —$CH_2CH_2CF_3$.

One embodiment provides a compound of Formula (I) or prodrugs thereof, wherein $R_1$ is —$CH_2CF_3$; $R_2$ is —$CH_2CF_3$; $R_3$ is H or —$CH_3$; and z is zero.

One embodiment provides a compound of Formula (I) or prodrugs thereof, wherein $R_1$ is —$CH_2CF_3$; $R_2$ is —$CH_2CH_2CF_3$; $R_3$ is H or —$CH_3$; and z is zero.

One embodiment provides a compound of Formula (I) or prodrugs thereof, wherein $R_1$ is —$CH_2CF_3$; $R_2$ is —$CH_2CH_2CH_2CF_3$; $R_3$ is H or —$CH_3$; and z is zero.

One embodiment provides a compound of Formula (I) or prodrugs thereof, wherein $R_1$ is —$CH_2CH_2CF_3$; $R_2$ is —$CH_2CF_3$; $R_3$ is H or —$CH_3$; and z is zero.

One embodiment provides a compound of Formula (I) or prodrugs thereof, wherein $R_1$ is —$CH_2CH_2CF_3$; $R_2$ is —$CH_2CH_2CF_3$; $R_3$ is H or —$CH_3$; and z is zero.

One embodiment provides a compound of Formula (I) or prodrugs thereof, wherein $R_1$ is —$CH_2CH_2CF_3$; $R_2$ is —$CH_2CH_2CH_2CF_3$; $R_3$ is H or —$CH_3$; and z is zero.

One embodiment provides a compound of Formula (I) or prodrugs thereof, wherein $R_1$ is —$CH_2CF_3$; $R_2$ is —$CH_2CF_3$; $R_3$ is H or —$CH_3$; z is 1; and $R_a$ is F, Cl, —CN, —$OCH_3$, and/or —$NHCH_2CH_2OCH_3$.

One embodiment provides a compound of Formula (I) or prodrugs thereof, wherein $R_1$ is —$CH_2CF_3$; $R_2$ is —$CH_2CH_2CF_3$; $R_3$ is H or —$CH_3$; z is 1; and $R_a$ is F, Cl, —CN, —$OCH_3$, and/or —$NHCH_2CH_2OCH_3$.

One embodiment provides a compound of Formula (I) or prodrugs thereof, wherein $R_1$ is —$CH_2CF_3$; $R_2$ is —$CH_2CH_2CH_2CF_3$; $R_3$ is H or —$CH_3$; z is 1; and $R_a$ is F, Cl, —CN, —$OCH_3$, and/or —$NHCH_2CH_2OCH_3$.

One embodiment provides a compound of Formula (I) or prodrugs thereof, wherein $R_1$ is —$CH_2CH_2CF_3$; $R_2$ is —$CH_2CF_3$; $R_3$ is H or —$CH_3$; z is 1; and $R_a$ is F, Cl, —CN, —$OCH_3$, and/or —$NHCH_2CH_2OCH_3$.

One embodiment provides a compound of Formula (I) or prodrugs thereof, wherein $R_1$ is —$CH_2CH_2CF_3$; $R_2$ is —$CH_2CH_2CF_3$; $R_3$ is H or —$CH_3$; z is 1; and $R_a$ is F, Cl, —CN, —$OCH_3$, and/or —$NHCH_2CH_2OCH_3$.

One embodiment provides a compound of Formula (I) or prodrugs thereof, wherein $R_1$ is —$CH_2CH_2CF_3$; $R_2$ is —$CH_2CH_2CH_2CF_3$; $R_3$ is H or —$CH_3$; z is 1; and $R_a$ is F, Cl, —CN, —$OCH_3$, and/or —$NHCH_2CH_2OCH_3$.

One embodiment provides a compound according to claim 1 or prodrugs thereof, selected from:

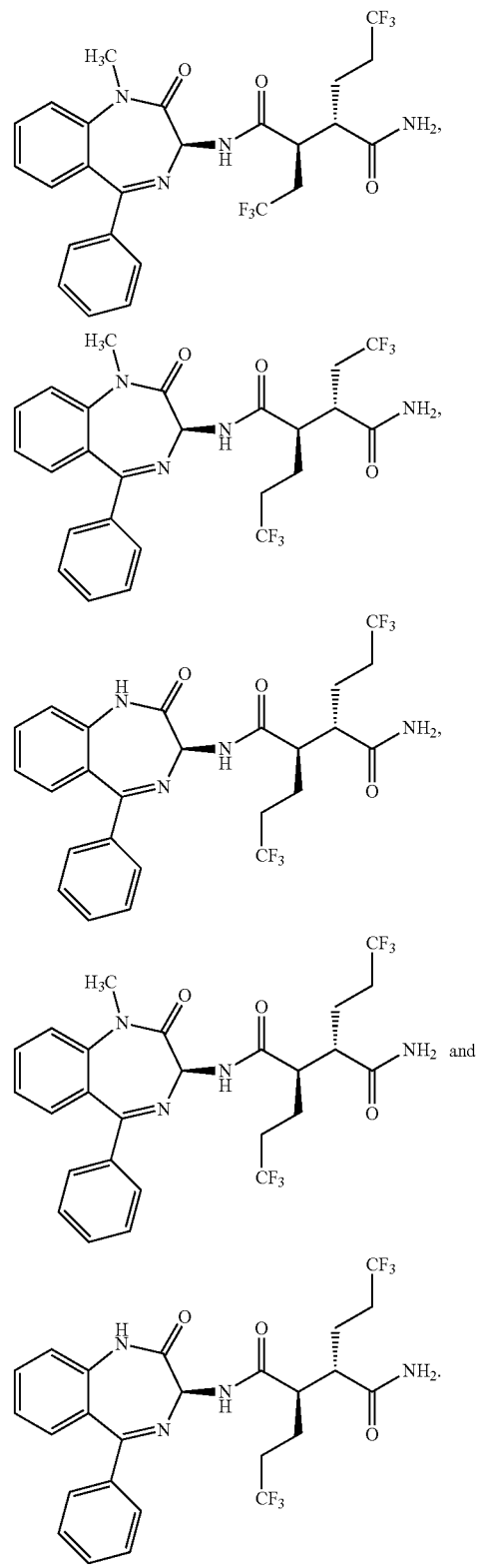

One embodiment provides a compound according to claim 1 or prodrugs thereof, selected from:

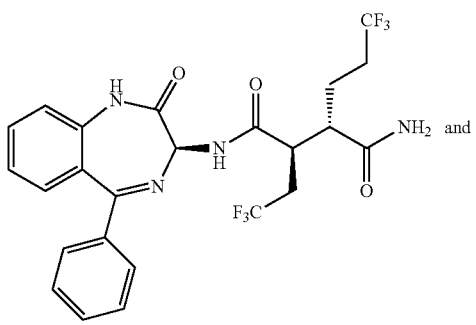

One embodiment provides a compound according to claim 1 or prodrugs thereof, selected from:

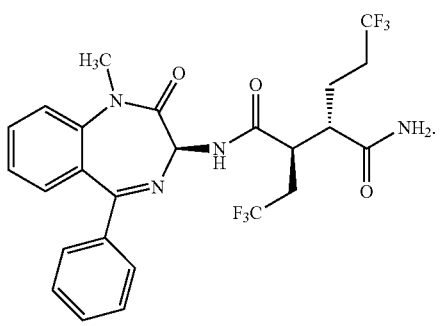

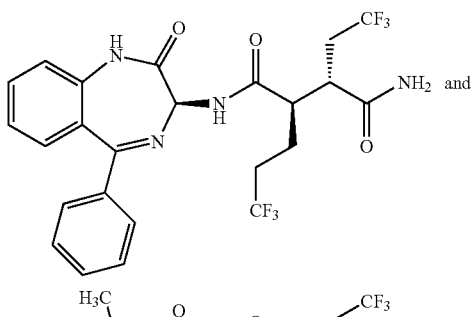

One embodiment provides a compound according to claim 1 or prodrugs thereof, selected from:

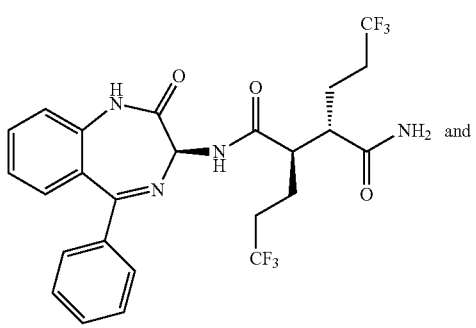

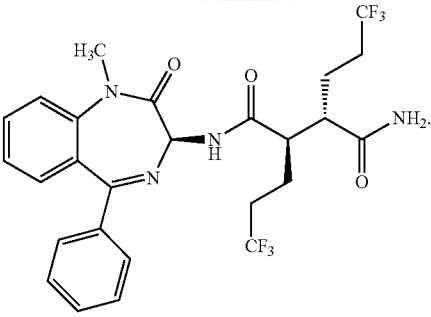

One embodiment provides a compound of Formula (I) selected from: (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide (1); (2R,3S)—N-((3S)-2-oxo-5-phenyl-2,3-dihydro-1H-1,4-benzodiazepin-3-yl)-2,3-bis(3,3,3-trifluoropropyl)succinamide (2); (2R,3S)—N-((3S)-1-methyl-2-oxo-5-phenyl-2,3-dihydro-1H-1,4-benzodiazepin-3-yl)-2-(2,2,2-trifluoroethyl)-3-(3,3,3-trifluoropropyl)succinamide (3); (2R,3S)—N-((3S)-1-methyl-2-oxo-5-phenyl-2,3-dihydro-1H-1,4-benzodiazepin-3-yl)-3-(2,2,2-trifluoroethyl)-2-(3,3,3-trifluoropropyl)succinamide (4); (2R,3S)—N-((3S)-1-($^2$H$_3$)methyl-2-oxo-5-phenyl-2,3-dihydro-1H-1,4-benzodiazepin-3-yl)-2,3-bis(3,3,3-trifluoropropyl)succinamide (5); (2R,3S)—N-((3S)-7-chloro-1-methyl-2-oxo-5-phenyl-2,3-dihydro-1H-1,4-benzodiazepin-3-yl)-2,3-bis(3,3,3-trifluoropropyl)succinamide (6); (2R,3S)—N-((3S)-8-methoxy-1-methyl-2-oxo-5-phenyl-2,3-dihydro-1H-1,4-benzodiazepin-3-yl)-2,3-bis(3,3,3-trifluoropropyl)succinamide (7); (2R,3S)—N-((3S)-8-fluoro-1-methyl-2-oxo-5-phenyl-2,3-dihydro-1H-1,4-benzodiazepin-3-yl)-2,3-bis(3,3,3-trifluoropropyl)succinamide (8); (2R,3S)—N-((3S)-7-methoxy-1-methyl-2-oxo-5-phenyl-2,3-dihydro-1H-1,4-benzodiazepin-3-yl)-2,3-bis(3,3,3-trifluoropropyl)succinamide (9); (2R,3S)—N-((3S)-7-fluoro-1-methyl-2-oxo-5-phenyl-2,3-dihydro-1H-1,4-benzodiazepin-3-yl)-2,3-bis(3,3,3-trifluoropropyl)succinamide (10); (2R,3S)—N-((3S)-8-chloro-1-methyl-2-oxo-5-phenyl-2,3-dihydro-1H-1,4-benzodiazepin-3-yl)-2,3-bis(3,3,3-trifluoropropyl)succinamide (11); (2R,3S)—N-((3S)-9-methoxy-2-oxo-5-phenyl-2,3-dihydro-1H-1,4-benzodiazepin-3-yl)-2,3-bis(3,3,3-trifluoropropyl)succinamide (12); (2R,3S)—N-((3S)-8-methoxy-2-oxo-5-phenyl-2,3-dihydro-1H-1,4-benzodiazepin-3-yl)-2,3-bis(3,3,3-trifluoropropyl)succinamide (13); (2R,3S)—N-((3S)-7-methoxy-2-oxo-5-phenyl-2,3-dihydro-1H-1,4-benzodiazepin-3-yl)-2,3-bis(3,3,3-trifluoropropyl)succinamide (14); (2R,3S)—N-((3S)-8-cyano-9-methoxy-2-oxo-5-phenyl-2,3-dihydro-1H-1,4-benzodiazepin-3-yl)-2,3-bis(3,3,3-trifluoropropyl)succinamide (15); (2R,3S)—N-((3S)-8,9-dichloro-2-oxo-5-phenyl-2,3-dihydro-1H-1,4-benzodiazepin-3-yl)-2,3-bis(3,3,3-trifluoropropyl)succinamide (16); (2R,3S)—N-((3S)-9-fluoro-2-oxo-5-phenyl-2,3-dihydro-1H-1,4-benzodiazepin-3-yl)-2,3-bis(3,3,3-trifluoropropyl)succinamide (17); (2R,3S)—N-((3S)-9-chloro-2-oxo-5-phenyl-2,3-dihydro-1H-1,4-benzodiazepin-3-yl)-2,3-bis(3,3,3-trifluoropropyl)succinamide (18); (2R,3S)—N-((3S)-2-oxo-5-phenyl-2,3-dihydro-1H-1,4-benzodiazepin-3-yl)-3-(4,4,4-trifluorobutyl)-2-(3,3,3-trifluoropropyl)succinamide (19); (2R,3S)—N1-((3S)-8-methoxy-2-oxo-5-phenyl-2,3-dihydro-1H-1,4-benzodiazepin-3-yl)-3-(4,4,4-trifluorobutyl)-2-(3,3,3-trifluoropropyl)succinamide (20); and (2R,3S)—N-((3S)-9-((2-methoxyethyl)amino)-2-oxo-5-phenyl-2,3- dihydro-1H-1,4-benzodiazepin-3-yl)-2,3-bis(3,3,3-trifluoropropyl)succinamide (21); and prodrugs of one or more of the above compounds.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, or I.

The term "alkyl" as used herein, refers to both branched and straight chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as a solid.

Any compound that can be converted in vivo to provide the bioactive agent (i.e., the compound of Formula (I)) is a prodrug within the scope and spirit of the invention.

Various forms of prodrugs are well known in the art and are described in:
a) Wermuth, C. G. et al., *The Practice of Medicinal Chemistry*, Chapter 31, Academic Press (1996);
b) Bundgaard, H. ed., *Design of Prodrugs*, Elsevier (1985);
c) Bundgaard, H., Chapter 5, "Design and Application of Prodrugs," Krosgaard-Larsen, P. et al., eds., *A Textbook of Drug Design and Development*, pp. 113-191, Harwood Academic Publishers (1991); and
d) Testa, B. et al., *Hydrolysis in Drug and Prodrug Metabolism*, Wiley-VCH (2003).

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Crystal Forms of the Compound of Example 1

In one embodiment, the compound of Example 1

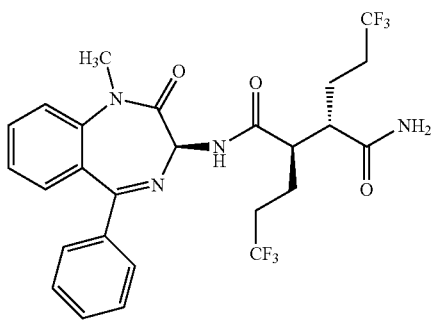 [SMILES: CN1C(=O)[C@@H](NC(=O)[C@H](CCC(F)(F)F)[C@H](CCC(F)(F)F)C(N)=O)N=C(c2ccccc2)c2ccccc21]

is provided as a crystalline material comprising one or more crystalline forms. Examples of suitable crystalline forms of the compound of Example 1 include Forms N-1, A-2, and EA-3.

In one embodiment, the compound of Example 1 is provided as a crystalline material comprising the first crystalline form. A first crystalline form of the compound of Example 1 comprises a neat crystalline form referred to herein as "Form N-1" or "N-1 Form".

In one embodiment, the N-1 Form of the compound of Example 1 is characterized by unit cell parameters approximately equal to the following:

Cell dimensions:
a=9.41 Å
b=17.74 Å
c=31.94 Å
α=90.0°
β=98.4°
γ=90.0°
Space group: $P2_1$
Molecules of Example 1/asymmetric unit: 4
Volume/Number of molecules in the unit cell=659 Å³
Density (calculated)=1.402 g/cm³, wherein the unit cell parameters of Form N-1 are measured at a temperature of about −10° C.

Figure 1:
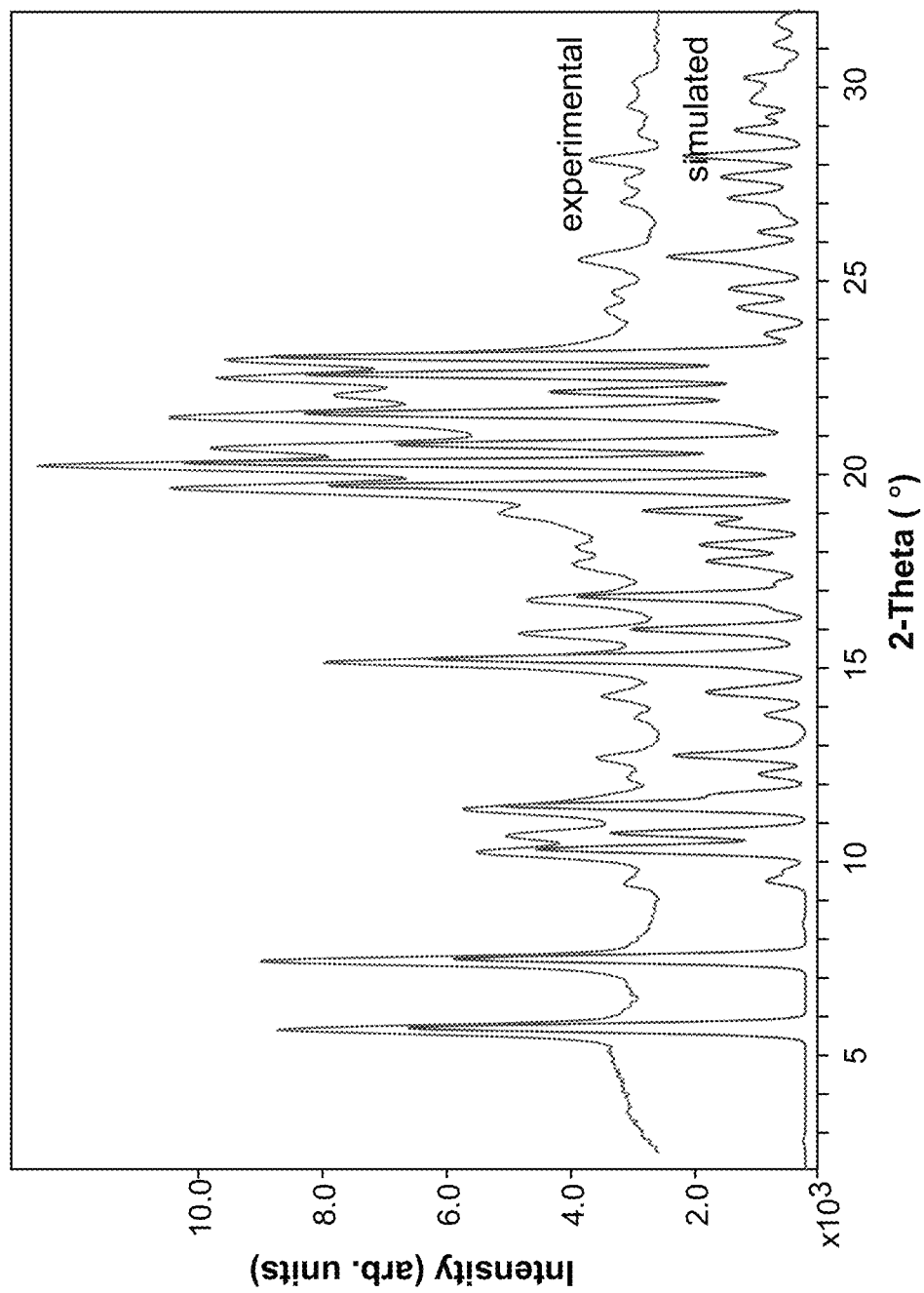
FIG. 1 shows the experimental (at approximately 25° C.) and the simulated (at approximately 25° C.) PXRD patterns (CuKα λ=1.5418 Å) of the N-1 Form of the compound of Example 1.

In another embodiment, the N-1 Form of the compound of Example 1 is characterized by a simulated powder x-ray diffraction (PXRD) pattern substantially in accordance with the pattern shown in FIG. 1 and/or by an observed PXRD pattern substantially in accordance with the pattern shown in FIG. 1

In yet another embodiment, the N-1 Form of the compound of Example 1 is characterized by a PXRD pattern (CuKα λ=1.5418 Å at a temperature of about 25° C.) comprising four or more, preferably five or more, 2θ values selected from: 5.7±0.2, 7.5±0.2, 10.3±0.2, 10.7±0.2, 15.2±0.2, 16.8±0.2, 20.2±0.2, and 20.7±0.2, wherein the PXRD pattern of Form N-1 is measured at a temperature of about 20° C.

In yet an even further embodiment, the N-1 Form of Example 1 is characterized by fractional atomic coordinates substantially as listed in Table 1.

TABLE 1

Fractional Atomic Coordinates of Form N-1 of Example 1 Calculated at a Temperature of about 25° C.; Atomic Coordinates (×10⁴) and Equivalent Isotropic Displacement Parameters (Å² × 10³)

| | x | y | z | U(eq)* |
|---|---|---|---|---|
| N(7) | 10824(5) | 7415(3) | 1732(1) | 39(1) |
| N(3) | 4985(5) | 565(2) | 1293(1) | 33(1) |
| O(3) | 7152(4) | 45(2) | 1509(1) | 45(1) |
| N(8) | 9981(6) | 10557(3) | 1329(2) | 60(2) |
| O(7) | 12033(5) | 10000(2) | 1229(1) | 55(1) |
| O(6) | 8697(5) | 7992(2) | 1768(1) | 53(1) |
| F(4) | 11039(5) | 8541(3) | 79(1) | 76(1) |
| C(17) | 5836(7) | 8(3) | 1469(1) | 30(1) |
| N(11) | 3979(5) | 1500(3) | 3735(1) | 35(1) |
| N(2) | 5338(6) | 2530(3) | 994(1) | 41(1) |
| C(8) | 7012(6) | 1237(3) | 77(2) | 35(1) |
| N(15) | 9277(5) | 4606(3) | 3230(1) | 37(1) |
| C(39) | 9990(7) | 8020(3) | 1739(2) | 36(1) |
| O(2) | 3365(5) | 1827(2) | 1076(1) | 49(1) |
| N(6) | 10513(6) | 5383(3) | 1910(2) | 46(1) |
| C(41) | 10028(6) | 9204(3) | 1300(2) | 36(1) |
| C(18) | 5094(6) | −692(3) | 1616(2) | 33(1) |
| C(22) | 5502(6) | −1369(3) | 1360(2) | 34(1) |
| C(23) | 4828(7) | −2081(3) | 1501(2) | 35(1) |
| C(2) | 6832(7) | 2584(3) | 978(2) | 44(2) |
| C(14) | 5639(7) | 1198(3) | 1113(2) | 37(1) |
| C(36) | 10130(7) | 6682(3) | 1698(2) | 37(1) |
| C(15) | 4647(7) | 1875(3) | 1071(2) | 37(1) |
| O(14) | 3524(5) | −2130(3) | 1484(2) | 63(1) |
| O(9) | 5867(5) | 1970(2) | 3461(1) | 46(1) |
| C(64) | 4608(7) | 2008(3) | 3517(2) | 35(1) |
| C(49) | 7025(7) | 893(4) | 5004(2) | 47(2) |
| O(12) | 7212(5) | 3943(2) | 3143(1) | 57(1) |
| F(5) | 8960(5) | 8082(2) | 93(1) | 73(1) |
| C(33) | 8030(8) | 6274(4) | −21(2) | 55(2) |
| N(5) | 9704(5) | 6528(3) | 1249(1) | 36(1) |
| C(42) | 10783(8) | 9965(4) | 1287(2) | 46(2) |
| O(5) | 12472(5) | 6155(3) | 1945(1) | 62(1) |
| C(37) | 11163(8) | 6062(4) | 1872(2) | 46(2) |
| F(7) | 9290(6) | 2987(3) | 5202(1) | 94(2) |
| C(65) | 3707(6) | 2688(3) | 3341(2) | 33(1) |
| N(4) | 5716(6) | −2636(3) | 1628(2) | 53(1) |
| C(7) | 6778(6) | 1429(3) | 518(2) | 34(1) |
| O(8) | 2612(5) | 231(2) | 3943(1) | 53(1) |
| O(11) | 10584(6) | 5864(3) | 3001(1) | 61(1) |
| C(89) | 8963(6) | 2807(3) | 3658(2) | 41(1) |
| C(70) | 4269(7) | 3355(4) | 4041(2) | 47(2) |
| N(13) | 8438(5) | 5493(3) | 3689(1) | 37(1) |
| C(20) | 5588(7) | −808(3) | 2089(2) | 38(1) |
| C(85) | 9369(8) | 5946(4) | 3070(2) | 46(2) |
| N(14) | 8611(7) | 6593(3) | 3016(2) | 55(1) |
| N(16) | 8948(7) | 1437(3) | 3656(2) | 68(2) |
| N(9) | 5416(5) | 1109(3) | 4375(1) | 37(1) |
| C(71) | 4930(8) | 4055(3) | 4280(2) | 51(2) |
| N(12) | 4314(6) | 4592(3) | 3189(2) | 68(2) |
| C(1) | 7546(7) | 2068(3) | 746(2) | 41(2) |
| O(13) | 11084(5) | 2050(3) | 3796(2) | 67(1) |
| C(73) | 7471(7) | 6206(4) | 4209(2) | 46(2) |
| C(6) | 9033(7) | 2147(4) | 744(2) | 51(2) |
| C(88) | 9391(7) | 3239(3) | 3270(2) | 44(2) |
| C(40) | 10716(7) | 8794(3) | 1708(2) | 41(1) |
| C(54) | 7871(7) | 381(4) | 5261(2) | 47(2) |
| C(67) | 3574(8) | 4095(4) | 3382(2) | 51(2) |
| F(6) | 8838(6) | 3995(2) | 4842(1) | 84(1) |
| C(79) | 7137(9) | 6649(4) | 3054(2) | 56(2) |
| C(24) | 8991(7) | 5283(3) | 1841(2) | 45(2) |
| C(31) | 8282(6) | 5837(3) | 703(2) | 37(1) |
| C(47) | 9570(7) | 9167(4) | 501(2) | 46(2) |
| C(63) | 4839(6) | 898(3) | 3940(2) | 34(1) |
| C(90) | 9762(7) | 2060(3) | 3707(2) | 45(2) |
| C(55) | 6443(6) | 715(3) | 4559(2) | 39(1) |
| C(68) | 3723(8) | 2732(4) | 2864(2) | 60(2) |
| C(59) | 8345(10) | −1056(5) | 3924(2) | 70(2) |
| C(75) | 7821(8) | 5880(5) | 4945(2) | 68(2) |
| C(32) | 8425(7) | 6417(3) | 405(2) | 50(2) |
| O(10) | 2312(5) | 4203(3) | 3420(2) | 75(2) |
| C(48) | 9694(8) | 8740(4) | 112(2) | 57(2) |
| N(10) | 4682(6) | −430(3) | 4071(1) | 46(1) |
| C(60) | 9196(10) | −525(5) | 4132(3) | 78(3) |

TABLE 1-continued

Fractional Atomic Coordinates of Form N-1 of Example 1 Calculated at a Temperature of about 25° C.; Atomic Coordinates (×10⁴) and Equivalent Isotropic Displacement Parameters (Å² × 10³)

|       | x        | y        | z       | U(eq)*  |
|-------|----------|----------|---------|---------|
| C(72) | 7560(6)  | 5996(3)  | 3766(2) | 38(1)   |
| C(11) | 7228(8)  | 906(5)   | −774(2) | 65(2)   |
| C(95) | 9510(8)  | 3334(4)  | 4845(2) | 56(2)   |
| C(86) | 8534(6)  | 5301(3)  | 3249(2) | 36(1)   |
| C(16) | 4463(10) | 3237(4)  | 980(2)  | 75(3)   |
| C(62) | 3917(7)  | 205(4)   | 3981(2) | 43(2)   |
| C(46) | 10181(7) | 8747(4)  | 901(2)  | 44(2)   |
| C(57) | 6210(8)  | −445(3)  | 4106(2) | 51(2)   |
| C(30) | 8759(6)  | 5995(3)  | 1157(2) | 35(1)   |
| C(66) | 4345(6)  | 3404(3)  | 3568(2) | 37(1)   |
| C(87) | 8540(6)  | 3940(3)  | 3212(2) | 40(1)   |
| C(93) | 9371(7)  | 3266(3)  | 4063(2) | 46(2)   |
| C(58) | 6870(9)  | −1041(4) | 3907(2) | 60(2)   |
| F(2)  | 11777(9) | 10008(4) | 2879(2) | 151(3)  |
| C(74) | 7871(7)  | 5699(4)  | 4528(2) | 55(2)   |
| C(25) | 8132(7)  | 5566(3)  | 1483(2) | 41(1)   |
| C(4)  | 9061(10) | 3259(5)  | 1173(2) | 76(2)   |
| C(26) | 6645(7)  | 5450(3)  | 1443(2) | 48(2)   |
| C(12) | 7727(9)  | 1590(5)  | −595(2) | 66(2)   |
| C(56) | 7085(7)  | 83(4)    | 4344(2) | 45(2)   |
| C(34) | 7488(7)  | 5600(4)  | −167(2) | 55(2)   |
| C(9)  | 6519(7)  | 574(4)   | −101(2) | 49(2)   |
| C(3)  | 7607(10) | 3182(5)  | 1190(2) | 66(2)   |
| C(81) | 5158(10) | 6468(4)  | 3438(2) | 76(2)   |
| C(45) | 11099(16)| 9317(7)  | 2895(3) | 121(4)  |
| C(43) | 10543(9) | 9268(4)  | 2103(2) | 64(2)   |
| F(3)  | 9787(11) | 9550(9)  | 2938(2) | 245(7)  |
| C(53) | 8327(8)  | 558(5)   | 5683(2) | 66(2)   |
| C(29) | 8344(10) | 4873(4)  | 2138(2) | 61(2)   |
| C(5)  | 9774(10) | 2734(5)  | 964(2)  | 76(2)   |
| C(80) | 6621(7)  | 6399(3)  | 3417(2) | 53(2)   |
| C(94) | 9050(7)  | 2877(4)  | 4460(2) | 51(2)   |
| C(38) | 11435(8) | 4768(4)  | 2102(2) | 71(2)   |
| C(13) | 7606(7)  | 1760(3)  | −179(2) | 48(2)   |
| C(61) | 3913(9)  | −1147(4) | 4095(2) | 71(2)   |
| C(52) | 8010(10) | 1214(6)  | 5841(2) | 79(2)   |
| C(10) | 6633(9)  | 406(4)   | −526(2) | 68(2)   |
| C(35) | 7696(8)  | 5160(4)  | 553(2)  | 57(2)   |
| C(84) | 9357(12) | 7262(4)  | 2869(3) | 91(3)   |
| C(91) | 9330(8)  | 2785(4)  | 2864(2) | 59(2)   |
| C(27) | 6019(9)  | 5060(4)  | 1739(2) | 69(2)   |
| C(44) | 11196(10)| 8906(4)  | 2495(2) | 78(2)   |
| C(69) | 3191(8)  | 2018(4)  | 2628(2) | 61(2)   |
| C(78) | 7034(8)  | 6922(4)  | 4311(2) | 64(2)   |
| C(83) | 6199(12) | 7012(5)  | 2740(3) | 87(3)   |
| C(82) | 4221(10) | 6784(6)  | 3121(4) | 100(3)  |
| C(51) | 7187(10) | 1748(5)  | 5591(2) | 79(2)   |
| C(76) | 7428(9)  | 6592(6)  | 5047(2) | 80(3)   |
| F(1)  | 11661(10)| 8983(5)  | 3228(2) | 186(4)  |
| C(50) | 6711(8)  | 1571(4)  | 5174(2) | 58(2)   |
| C(77) | 7057(9)  | 7114(5)  | 4734(3) | 85(3)   |
| N(1)  | 5875(5)  | 999(2)   | 684(1)  | 34(1)   |
| C(102)| 5582(7)  | −1953(3) | 630(2)  | 49(2)   |
| C(101)| 5084(7)  | −1277(3) | 879(2)  | 44(2)   |
| C(100)| 5214(10) | −152(4)  | 2344(2) | 73(2)   |
| C(104)| 7326(8)  | 5036(4)  | 115(2)  | 70(2)   |
| C(28) | 6897(11) | 4774(4)  | 2086(3) | 75(2)   |
| F(40) | 9173(5)  | 9112(2)  | −241(1) | 74(1)   |
| C(105)| 8587(8)  | 41(4)    | 4352(2) | 60(2)   |
| C(124)| 2922(10) | 2104(6)  | 2165(3) | 82(3)   |
| F(42) | 4029(8)  | 2397(5)  | 2012(2) | 142(3)  |
| F(43) | 1850(8)  | 2595(5)  | 2046(2) | 134(2)  |
| F(41) | 2570(8)  | 1475(4)  | 1965(2) | 139(2)  |
| C(122)| 5045(7)  | 3962(4)  | 4744(2) | 51(2)   |
| F(44) | 5920(5)  | 3370(2)  | 4887(1) | 74(1)   |
| C(45) | 5616(8)  | 4563(2)  | 4959(1) | 75(1)   |
| F(46) | 3833(5)  | 3823(2)  | 4879(1) | 75(1)   |
| C(108)| 4748(13) | 7054(5)  | 2773(3) | 100(3)  |
| F(47) | 8547(9)  | 2143(4)  | 2026(2) | 152(3)  |
| F(48) | 6731(8)  | 1653(4)  | 2180(2) | 145(2)  |
| F(49) | 10919(5) | 3510(3)  | 4901(1) | 81(1)   |
| C(123)| 7913(9)  | 2494(5)  | 2683(2) | 73(2)   |
| C(121)| 7997(12) | 1902(6)  | 2341(3) | 89(3)   |
| C(120)| 5377(8)  | −1834(4) | 184(2)  | 53(2)   |

TABLE 1-continued

Fractional Atomic Coordinates of Form N-1 of Example 1 Calculated at a Temperature of about 25° C.; Atomic Coordinates (×10⁴) and Equivalent Isotropic Displacement Parameters (Å² × 10³)

|       | x        | y        | z       | U(eq)*  |
|-------|----------|----------|---------|---------|
| C(109)| 5564(11) | −282(5)  | 2811(2) | 79(3)   |
| F(55) | 3970(4)  | −1704(2) | 15(1)   | 70(1)   |
| F(54) | 6048(5)  | −1235(2) | 59(1)   | 67(1)   |
| F(56) | 5748(5)  | −2425(2) | −34(1)  | 69(1)   |
| F(53) | 4868(7)  | −845(3)  | 2948(1) | 100(2)  |
| F(51) | 5179(13) | 300(4)   | 3035(2) | 189(4)  |
| F(52) | 6924(8)  | −420(6)  | 2920(2) | 181(4)  |
| F(60) | 8732(11) | 1307(3)  | 2477(2) | 192(4)  |

*U(eq) is defined as one third of the trace of the orthogonalized $U^{ij}$ tensor.

In still yet an even further embodiment, the N-1 form of the compound of Example 1 is substantially pure.

In still yet another embodiment, the N-1 form of the compound of Example 1 contains at least about 90 wt. %, preferably at least about 95 wt. %, and more preferably at least about 99 wt. %, based on weight of the Form N-1 of the compound of Example 1.

In yet another embodiment, a substantially pure Form N-1 of the compound of Example 1 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure crystalline Form N-1 has substantially pure phase homogeneity with less than about 1% of the total peak area of the experimentally measured PXRD pattern arising from peaks that are absent from the simulated PXRD pattern.

In another embodiment, the crystalline form of the compound of Example 1 consists essentially of Form N-1. The crystalline form of this embodiment may comprise at least about 90 wt. %, preferably at least about 95 wt. %, and more preferably at least about 99 wt. %, based on the weight of the crystalline form, Form N-1 of the compound of Example 1.

In yet another embodiment, a pharmaceutical composition is provided comprising Form N-1 of the compound of Example 1; and at least one pharmaceutically-acceptable carrier and/or diluent.

In still another embodiment, a pharmaceutical composition comprises substantially pure Form N-1 of compound of Example 1; and at least one pharmaceutically-acceptable carrier and/or diluent.

In still an even further embodiment, a therapeutically effective amount of Form N-1 of the compound of Example 1 is combined with at least one pharmaceutically acceptable carrier and/or diluent to provide at least one pharmaceutical composition.

In one embodiment, the compound of Example 1 is provided in a second crystalline form. The second crystalline form is an acetone solvate crystalline form referred to herein as "Form A-2" or "A-2 Form". The A-2 Form comprises about one acetone molecule for each molecule of Example 1.

In one embodiment, the A-2 Form is characterized by unit cell parameters approximately equal to the following:

Cell dimensions:

a=9.25 Å b=17.11 Å c=19.63 Å

α=90.0°

β=99.2°
γ=90.0°
Space group: P2$_1$
Molecules of Example 1/asymmetric unit: 2
Volume/number of molecules in the unit cell=767 Å$^3$
Density (calculated)=1.331 g/cm$^3$,
wherein the unit cell parameters of Form A-2 are measured at a temperature of about −50° C.

Figure 2:
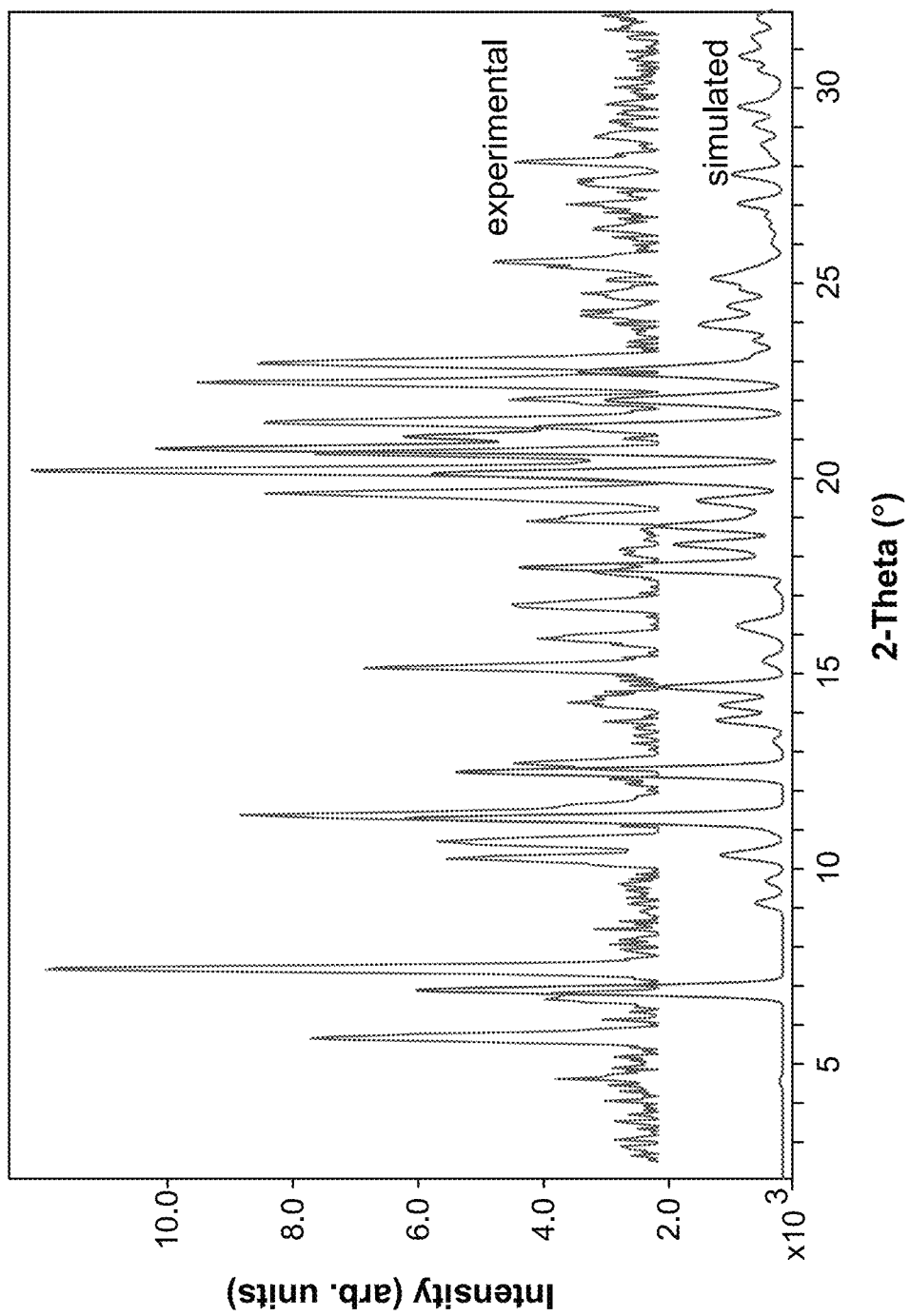
FIG. 2 shows the experimental (at approximately 25° C.) and the simulated (at approximately 25° C.) PXRD patterns (CuKα λ=1.5418 Å) of the A-2 Form of the compound of Example 1.

In another embodiment, the A-2 Form is characterized by a simulated powder x-ray diffraction (PXRD) pattern substantially in accordance with the pattern shown in FIG. 2 and/or by an observed PXRD pattern substantially in accordance with the pattern shown in FIG. 2.

In yet an even further embodiment, the A-2 Form of Example 1 is characterized by fractional atomic coordinates substantially as listed in Table 2.

TABLE 2

Fractional Atomic Coordinates of Form A-2 of Example 1 Calculated at a Temperature of about 25° C.; Atomic Coordinates (×10$^4$) and Equivalent Isotropic Displacement Parameters (Å$^2$ × 10$^3$)

| | x | y | z | U(eq)* |
|---|---|---|---|---|
| C(7) | 6904(4) | 4997(2) | 5292(2) | 48(1) |
| C(1) | 8004(4) | 5982(2) | 6174(2) | 54(1) |
| C(2) | 6800(4) | 5545(2) | 5859(2) | 54(1) |
| C(8) | 6141(4) | 4232(2) | 5284(2) | 54(1) |
| C(3) | 5457(5) | 5651(3) | 6082(2) | 76(1) |
| C(11) | 4844(6) | 2766(3) | 5230(3) | 85(2) |
| C(6) | 7848(6) | 6490(3) | 6720(2) | 71(1) |
| C(13) | 6027(5) | 3824(3) | 5876(2) | 70(1) |
| C(9) | 5582(5) | 3890(3) | 4653(2) | 71(1) |
| C(12) | 5401(6) | 3097(3) | 5850(3) | 83(2) |
| C(10) | 4917(6) | 3170(3) | 4628(3) | 90(2) |
| C(5) | 6489(7) | 6573(3) | 6912(3) | 90(2) |
| C(4) | 5305(7) | 6149(4) | 6600(3) | 97(2) |
| N(1) | 9412(3) | 5900(2) | 5975(2) | 51(1) |
| N(2) | 7595(3) | 5151(2) | 4788(2) | 44(1) |
| C(14) | 10740(5) | 5965(3) | 6513(2) | 74(1) |
| O(2) | 10864(3) | 5937(2) | 5145(1) | 55(1) |
| C(16) | 8251(3) | 5933(2) | 4786(2) | 40(1) |
| C(15) | 9646(4) | 5938(2) | 5311(2) | 44(1) |
| N(3) | 8562(3) | 6099(2) | 4109(1) | 41(1) |
| C(17) | 7467(4) | 6272(2) | 3606(2) | 39(1) |
| O(3) | 6194(2) | 6341(2) | 3715(1) | 51(1) |
| C(18) | 7818(4) | 6368(2) | 2879(2) | 42(1) |
| C(19) | 7150(4) | 5692(2) | 2427(2) | 43(1) |
| C(20) | 7742(4) | 5710(2) | 1743(2) | 47(1) |
| C(21) | 7295(4) | 7162(2) | 2603(2) | 53(1) |
| C(22) | 7920(6) | 7834(3) | 3079(2) | 71(1) |
| C(23) | 7430(10) | 8614(3) | 2824(3) | 107(2) |
| C(24) | 7536(4) | 4901(2) | 2785(2) | 52(1) |
| C(25) | 7093(6) | 4206(3) | 2330(2) | 71(1) |
| C(26) | 7241(8) | 3455(3) | 2704(3) | 94(2) |
| F(6) | 6297(5) | 3386(2) | 3134(2) | 129(1) |
| F(1) | 7959(8) | 9176(2) | 3262(2) | 185(3) |
| F(5) | 8543(6) | 3362(2) | 3105(3) | 150(2) |
| F(3) | 7942(5) | 8794(2) | 2229(2) | 126(1) |
| F(4) | 7086(8) | 2841(2) | 2316(3) | 195(3) |
| F(2) | 5988(6) | 8693(2) | 2664(3) | 144(2) |
| O(4) | 9043(3) | 5579(2) | 1739(1) | 64(1) |
| N(4) | 6801(3) | 5840(2) | 1174(2) | 58(1) |
| C(28) | 3228(5) | 5219(2) | −666(2) | 58(1) |
| C(27) | 2067(5) | 5688(2) | −980(2) | 58(1) |
| C(34) | 3784(6) | 3921(3) | −46(2) | 72(1) |
| C(33) | 3100(5) | 4701(2) | −78(2) | 58(1) |
| C(35) | 4203(7) | 3574(3) | 594(3) | 97(2) |
| C(39) | 3986(6) | 3507(3) | −636(3) | 83(2) |
| C(32) | 2285(6) | 6154(3) | −1536(2) | 75(1) |
| C(30) | 4731(7) | 5711(3) | −1475(3) | 91(2) |
| C(38) | 4583(7) | 2762(3) | −576(3) | 98(2) |
| C(29) | 4568(6) | 5253(2) | −917(2) | 72(1) |
| C(31) | 3577(7) | 6155(3) | −1784(3) | 87(2) |
| C(37) | 4968(9) | 2422(4) | 54(4) | 118(2) |
| C(36) | 4771(9) | 2808(4) | 624(4) | 128(3) |
| N(5) | 661(4) | 5680(2) | −773(2) | 60(1) |
| N(6) | 2443(4) | 4911(2) | 431(2) | 54(1) |
| C(40) | −651(6) | 5774(3) | −1302(2) | 86(2) |
| O(5) | −740(4) | 5772(2) | 72(2) | 68(1) |
| C(41) | 469(4) | 5735(2) | −103(2) | 53(1) |
| C(42) | 1863(4) | 5705(2) | 419(2) | 46(1) |
| N(7) | 1560(3) | 5910(2) | 1090(1) | 45(1) |
| C(43) | 2620(4) | 6162(2) | 1576(2) | 46(1) |
| O(6) | 3897(3) | 6255(2) | 1483(1) | 57(1) |
| C(44) | 2172(4) | 6353(3) | 2271(2) | 52(1) |
| C(46) | 2395(4) | 5950(4) | 3504(2) | 74(1) |
| C(45) | 3085(4) | 5884(3) | 2850(2) | 62(1) |
| C(48) | 1358(6) | 7707(3) | 1848(3) | 83(1) |
| C(47) | 2339(5) | 7234(3) | 2392(2) | 67(1) |
| C(51) | 1858(6) | 4543(4) | 2518(4) | 107(2) |
| C(50) | 3255(4) | 5013(3) | 2687(2) | 70(1) |
| C(49) | 1563(10) | 8561(4) | 1908(5) | 124(2) |
| C(52) | 2084(6) | 3715(4) | 2468(4) | 99(2) |
| F(12) | 3031(5) | 3498(3) | 2086(3) | 142(2) |
| F(10) | 2663(6) | 3415(3) | 3096(3) | 163(2) |
| F(9) | 1342(6) | 8818(3) | 2530(3) | 163(2) |
| F(11) | 888(5) | 3295(3) | 2278(4) | 183(3) |
| F(8) | 2877(7) | 8787(3) | 1859(4) | 207(3) |
| F(7) | 614(7) | 8955(3) | 1439(3) | 173(2) |
| O(7) | 3291(3) | 5999(2) | 4102(2) | 84(1) |
| N(8) | 1075(3) | 5907(4) | 3480(2) | 127(3) |
| O(1S) | 8859(5) | 7601(2) | 5406(3) | 125(2) |
| C(2S) | 9451(6) | 8179(2) | 5220(3) | 93(2) |
| C(1S) | 8949(12) | 8987(3) | 5332(6) | 178(4) |
| C(3S) | 10720(8) | 8060(6) | 4852(5) | 170(4) |
| C(5S) | 894(7) | 8038(3) | 9719(4) | 114(2) |
| C(6S) | 1519(16) | 8821(4) | 9622(7) | 237(7) |
| C(4S) | −672(9) | 7980(10) | 9801(11) | 366(14) |
| O(2S) | 1390(8) | 7390(3) | 9852(6) | 226(4) |

*U(eq) is defined as one third of the trace of the orthogonalized U$^{ij}$ tensor.

In still yet an even further embodiment, the A-2 form of the compound of Example 1 is substantially pure.

In still yet another embodiment, the A-2 form of the compound of Example 1 contains at least about 90 wt. %, preferably at least about 95 wt. %, and more preferably at least about 99 wt. %, based on weight of the second crystalline form, Form A-2.

In yet another embodiment, a substantially pure second crystalline form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure second crystalline form has substantially pure phase homogeneity with less than about 1% of the total peak area of the experimentally measured PXRD pattern arising from peaks that are absent from the simulated PXRD pattern.

In another embodiment, the second crystalline form of the compound of Example 1 consists essentially of Form A-2. The second crystalline form of this embodiment may comprise at least about 90 wt. %, preferably at least about 95 wt. %, and more preferably at least about 99 wt. %, based on the weight of the second crystalline form, Form A-2.

In one embodiment, the compound of Example 1 is provided in a third crystalline form. The third crystalline form is an ethyl acetate solvate crystalline form referred to herein as "Form EA-3" or "EA-3 Form". The EA-3 Form comprises about one ethyl acetate molecule for each molecule of Example 1.

In one embodiment, the EA-3 Form is characterized by unit cell parameters approximately equal to the following:
Cell dimensions:
a=8.84 Å
b=15.95 Å
c=22.38 Å
α=90.0°
β=90.0°
γ=90.0°
Space group: P2$_1$2$_1$2$_1$
Molecules of Example 1/asymmetric unit: 1
Volume/number of molecules in the unit cell=789 Å$^3$
Density (calculated)=1.357 g/cm$^3$,
wherein the unit cell parameters of Form EA-3 are measured at a temperature of about −50° C.

Figure 3:
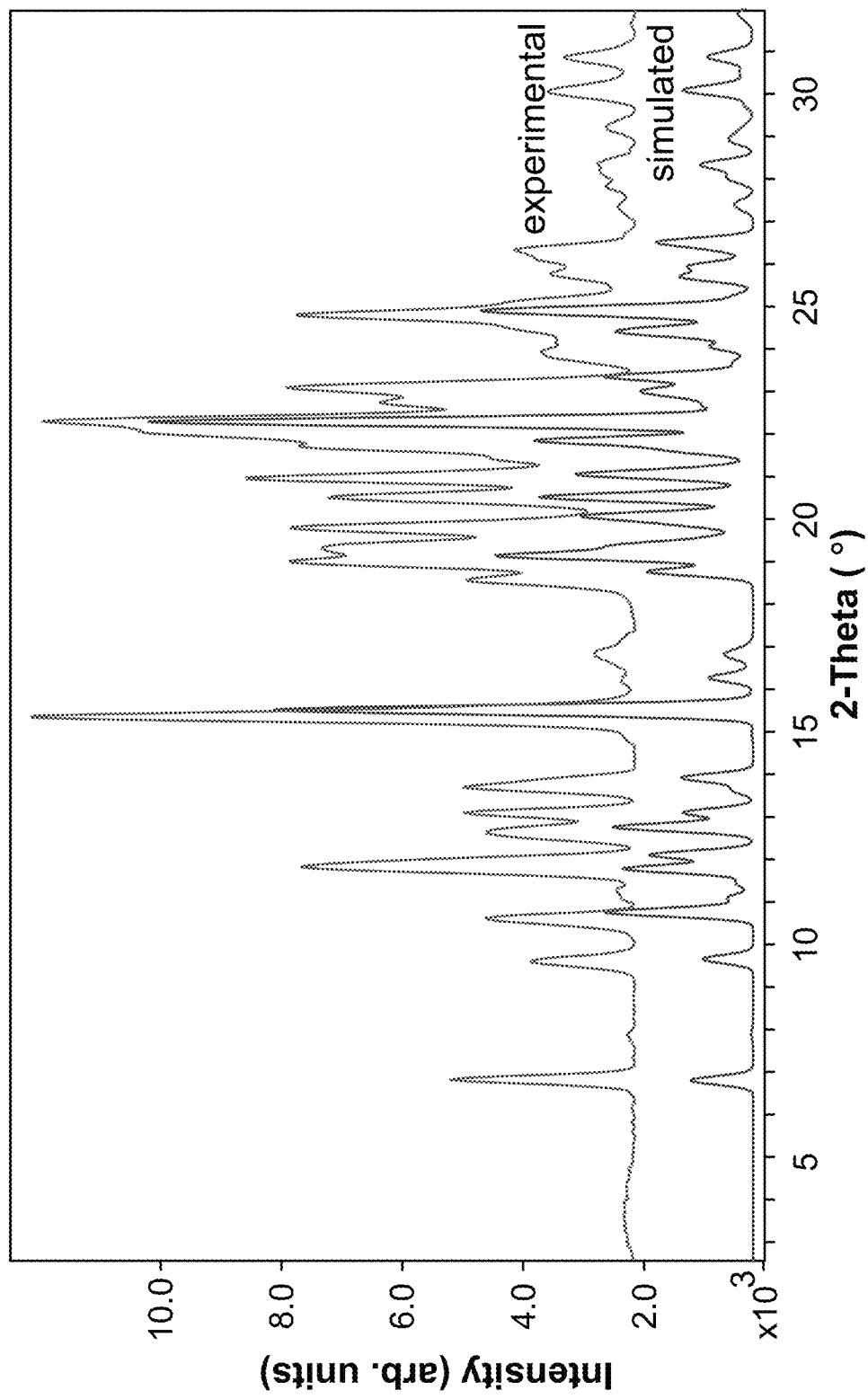
FIG. 3 shows the experimental (at approximately 25° C.) and the simulated (at approximately 25° C.) PXRD patterns (CuKα λ=1.5418 Å) of the EA-3 Form of the compound of Example 1.

In another embodiment, the EA-3 Form is characterized by a simulated powder x-ray diffraction (PXRD) pattern substantially in accordance with the pattern shown in FIG. 3 and/or by an observed PXRD pattern substantially in accordance with the pattern shown in FIG. 3.

In yet another embodiment, the EA-3 Form of the compound of Example 1 is characterized by a PXRD pattern (CuKα λ=1.5418 Å at a temperature of about 25° C.) comprising four or more, preferably five or more, 2θ values selected from: 6.8±0.2, 9.6±0.2, 10.6±0.2, 15.4±0.2, 20.5±0.2, 21.0±0.2, and 24.8±0.2, wherein the PXRD pattern of Form N-1 is measured at a temperature of about 20° C.

In yet an even further embodiment, the EA-3 Form of Example 1 is characterized by fractional atomic coordinates substantially as listed in Table 3.

TABLE 3

Fractional Atomic Coordinates of Form EA-3 of Example 1 Calculated at a Temperature of about 25° C.; Atomic Coordinates (×10$^4$) and Equivalent Isotropic Displacement Parameters (Å$^2$ × 10$^3$)

|       | x        | y       | z       | U(eq)*  |
|-------|----------|---------|---------|---------|
| F(1)  | 10284(3) | −324(1) | 8889(1) | 110(1)  |
| F(2)  | 8491(2)  | −284(1) | 9520(1) | 93(1)   |
| F(3)  | 10700(3) | 44(1)   | 9784(1) | 113(1)  |
| F(4)  | 10501(3) | 5623(1) | 9310(1) | 130(1)  |
| F(5)  | 8241(3)  | 5391(1) | 9141(1) | 115(1)  |
| F(6)  | 8839(3)  | 5780(1) | 9997(1) | 105(1)  |
| O(1)  | 11040(2) | 2804(1) | 6756(1) | 47(1)   |
| O(2)  | 7956(1)  | 2449(1) | 8498(1) | 36(1)   |
| O(3)  | 12740(2) | 2982(1) | 9716(1) | 40(1)   |
| N(1)  | 8842(2)  | 2728(1) | 6240(1) | 33(1)   |
| N(2)  | 8089(2)  | 3668(1) | 7331(1) | 33(1)   |
| N(3)  | 9769(2)  | 2708(1) | 7813(1) | 33(1)   |
| N(4)  | 10970(2) | 2584(1) | 10384(1)| 35(1)   |
| C(1)  | 7242(2)  | 2620(1) | 6240(1) | 31(1)   |
| C(2)  | 6305(2)  | 3136(1) | 6588(1) | 32(1)   |
| C(3)  | 4744(2)  | 2988(1) | 6568(1) | 41(1)   |
| C(4)  | 4146(3)  | 2361(2) | 6218(1) | 46(1)   |
| C(5)  | 5082(2)  | 1865(2) | 5875(1) | 45(1)   |
| C(6)  | 6619(2)  | 1993(2) | 5884(1) | 41(1)   |
| C(7)  | 6958(2)  | 3796(1) | 6978(1) | 32(1)   |
| C(8)  | 6335(2)  | 4667(1) | 6961(1) | 38(1)   |
| C(9)  | 6764(3)  | 5243(2) | 7398(1) | 49(1)   |
| C(10) | 6266(3)  | 6066(2) | 7374(1) | 62(1)   |
| C(11) | 5332(3)  | 6325(2) | 6919(1) | 65(1)   |
| C(12) | 4902(3)  | 5765(2) | 6489(1) | 61(1)   |
| C(13) | 5402(3)  | 4943(2) | 6502(1) | 49(1)   |
| C(14) | 9661(2)  | 2771(1) | 6748(1) | 33(1)   |
| C(15) | 8737(2)  | 2828(1) | 7322(1) | 31(1)   |
| C(16) | 9646(3)  | 2733(1) | 5664(1) | 42(1)   |
| C(17) | 9303(2)  | 2523(1) | 8366(1) | 28(1)   |
| C(18) | 10560(2) | 2404(1) | 8823(1) | 28(1)   |
| C(19) | 10812(2) | 1469(1) | 8954(1) | 33(1)   |
| C(20) | 9417(3)  | 1000(1) | 9175(1) | 40(1)   |
| C(21) | 9715(3)  | 119(2)  | 9337(1) | 56(1)   |
| C(22) | 10180(2) | 2934(1) | 9377(1) | 28(1)   |

TABLE 3-continued

Fractional Atomic Coordinates of Form EA-3 of Example 1 Calculated at a Temperature of about 25° C.; Atomic Coordinates (×10$^4$) and Equivalent Isotropic Displacement Parameters (Å$^2$ × 10$^3$)

|       | x        | y       | z       | U(eq)*  |
|-------|----------|---------|---------|---------|
| C(23) | 10038(2) | 3867(1) | 9211(1) | 35(1)   |
| C(24) | 9480(3)  | 4403(1) | 9721(1) | 53(1)   |
| C(25) | 9272(3)  | 5289(2) | 9554(1) | 62(1)   |
| C(26) | 11411(2) | 2830(1) | 9845(1) | 28(1)   |
| O(1S) | 3231(2)  | 3405(1) | 7982(1) | 68(1)   |
| O(2S) | 2969(2)  | 4783(1) | 8077(1) | 64(1)   |
| C(1S) | 4926(3)  | 4166(2) | 8613(1) | 78(1)   |
| C(2S) | 3651(3)  | 4066(2) | 8192(1) | 54(1)   |
| C(3S) | 1698(3)  | 4746(2) | 7661(1) | 70(1)   |
| C(4S) | 1132(4)  | 5596(2) | 7579(2) | 85(1)   |

*U(eq) is defined as one third of the trace of the orthogonalized U$^{ij}$ tensor.

In still yet an even further embodiment, the EA-3 form of the compound of Example 1 is substantially pure.

In still yet another embodiment, the EA-3 form of the compound of Example 1 contains at least about 90 wt. %, preferably at least about 95 wt. %, and more preferably at least about 99 wt. %, based on weight of the third crystalline form, Form EA-3.

In yet another embodiment, a substantially pure Form EA-3 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially crystalline Form EA-3 has substantially pure phase homogeneity with less than about 1% of the total peak area of the experimentally measured PXRD pattern arising from peaks that are absent from the simulated PXRD pattern.

In another embodiment, the third crystalline form of the compound of Example 1 consists essentially of Form EA-3. The third crystalline form of this embodiment may comprise at least about 90 wt. %, preferably at least about 95 wt. %, and more preferably at least about 99 wt. %, based on the weight of the third crystalline form, Form EA-3.

In one embodiment, the compound of Example 1 is provided in a fourth crystalline form. The fourth crystalline form is an tetrahydrofuran solvate crystalline form referred to herein as "Form THF-2" or "THF-2 Form". The THF-2 Form comprises about one tetrahydrofuran molecule for each molecule of Example 1.

In one embodiment, the THF-2 Form is characterized by unit cell parameters approximately equal to the following:
Cell dimensions:
a=9.34 Å
b=16.44 Å
c=20.60 Å
α=90.0°
β=102.8°
γ=90.0°
Space group: P2$_1$
Molecules of Example 1/asymmetric unit: 2
Molecules of tetrahydrofuran/asymmetric unit: 2
Volume=3082 Å$^3$,
wherein the unit cell parameters of Form THF-2 are measured at a temperature of about −50° C.

Figure 4:
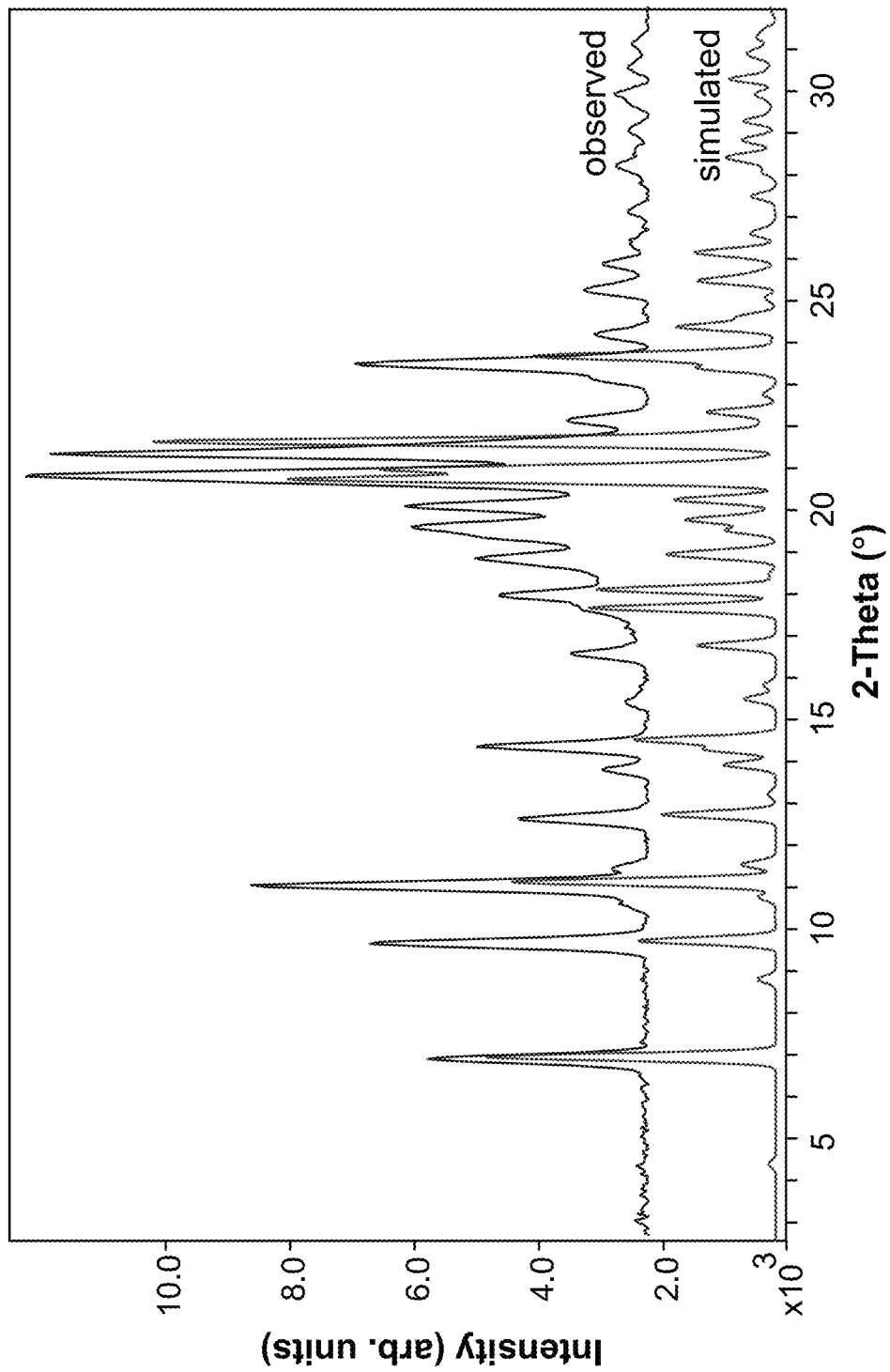
FIG. 4 shows the experimental (at approximately 25° C.) and the simulated (at approximately −50° C.) PXRD patterns (CuKα λ=1.5418 Å) of the THF-2 Form of the compound of Example 1.

In another embodiment, the THF-2 Form is characterized by a simulated powder x-ray diffraction (PXRD) pattern substantially in accordance with the pattern shown in FIG. 4 and/or by an observed PXRD pattern substantially in accordance with the pattern shown in FIG. 4.

In yet another embodiment, the THF-2 Form of the compound of Example 1 is characterized by a PXRD pattern (CuKα λ=1.5418 Å at a temperature of about 25° C.) comprising four or more, preferably five or more, 2θ values selected from: 6.9±0.2, 9.6±0.2, 11.2±0.2, 12.6±0.2, 16.6±0.2, 21.4±0.2, and 24.2±0.2, wherein the PXRD pattern of Form N-1 is measured at a temperature of about 20° C.

In yet an even further embodiment, the THF-2 Form of Example 1 is characterized by fractional atomic coordinates substantially as listed in Table 4.

TABLE 4

Fractional Atomic Coordinates of Form THF-2 of Example 1 (Not Including Solvent Molecules) Calculated at a Temperature of about −50° C.; Atomic Coordinates (×10$^4$) and Equivalent Isotropic Displacement Parameters (Å$^2$ × 10$^3$)

| | x | y | z | U(eq)* |
|---|---|---|---|---|
| C(15) | 5518(8) | 5421(5) | −198(4) | 40(2) |
| C(7) | 8183(7) | 4416(4) | −230(3) | 37(2) |
| C(1) | 6912(8) | 5409(5) | −1086(3) | 40(2) |
| C(14) | 7026(7) | 5430(4) | 285(3) | 33(2) |
| C(8) | 8844(8) | 3587(5) | −216(4) | 43(2) |
| C(10) | 9968(13) | 2433(7) | 425(5) | 77(3) |
| C(3) | 9384(9) | 5015(5) | −1084(4) | 53(2) |
| C(13) | 8784(8) | 3143(5) | −809(4) | 48(2) |
| C(9) | 9434(11) | 3222(6) | 378(4) | 63(2) |
| C(2) | 8146(8) | 4952(5) | −811(3) | 39(2) |
| C(16) | 4171(9) | 5392(7) | −1345(4) | 67(2) |
| C(11) | 9807(11) | 1985(6) | −145(5) | 65(2) |
| C(4) | 9404(10) | 5497(6) | −1633(4) | 57(2) |
| C(12) | 9264(9) | 2348(5) | −782(4) | 53(2) |
| C(6) | 6924(11) | 5907(5) | −1633(4) | 54(2) |
| C(5) | 8182(12) | 5952(6) | −1902(4) | 64(3) |
| N(1) | 5578(6) | 5360(4) | −848(3) | 42(1) |
| N(3) | 6888(8) | 5605(4) | 938(3) | 36(1) |
| N(2) | 7672(6) | 4610(4) | 275(3) | 35(1) |
| O(1) | 4390(5) | 5416(4) | −2(3) | 52(1) |
| O(2) | 9346(5) | 5736(3) | 1309(2) | 39(1) |
| C(18) | 7891(7) | 5843(4) | 2128(3) | 34(2) |
| C(19) | 8603(6) | 5146(4) | 2580(3) | 32(2) |
| C(17) | 8107(7) | 5722(4) | 1427(3) | 31(2) |
| C(24) | 8791(9) | 3596(5) | 2706(4) | 48(2) |
| C(23) | 8173(8) | 4312(5) | 2258(3) | 39(2) |
| C(22) | 8487(11) | 8173(5) | 2261(5) | 62(2) |
| C(20) | 8557(8) | 6655(5) | 2400(3) | 39(2) |
| C(21) | 7907(9) | 7385(5) | 1964(4) | 49(2) |
| C(25) | 8741(10) | 2810(5) | 2355(4) | 52(2) |
| C(26) | 8152(8) | 5186(6) | 3247(3) | 37(2) |
| F(1) | 9955(6) | 8219(4) | 2328(4) | 93(2) |
| F(2) | 7946(8) | 8805(4) | 1891(4) | 99(2) |
| F(3) | 8223(9) | 8310(5) | 2860(3) | 95(2) |
| F(6) | 9312(8) | 2189(5) | 2738(3) | 85(2) |
| F(4) | 9544(10) | 2827(4) | 1887(3) | 107(3) |
| F(5) | 7371(8) | 2601(4) | 2055(4) | 99(2) |
| O(3) | 6868(5) | 5095(4) | 3269(2) | 53(2) |
| N(4) | 9201(7) | 5323(5) | 3773(3) | 50(2) |
| C(41) | 5606(8) | 5376(5) | 5015(4) | 44(2) |
| C(33) | 2941(8) | 4383(5) | 5034(4) | 44(2) |
| C(40) | 4123(8) | 5383(5) | 4524(3) | 40(2) |
| C(34) | 2252(8) | 3558(5) | 5001(3) | 43(2) |
| C(35) | 1639(9) | 3211(5) | 4394(4) | 50(2) |
| C(28) | 2933(9) | 4914(5) | 5586(4) | 46(2) |
| C(39) | 2268(11) | 3105(6) | 5556(4) | 64(2) |
| C(36) | 1122(10) | 2419(6) | 4377(4) | 63(2) |
| C(27) | 4177(9) | 5378(5) | 5892(4) | 49(2) |
| C(29) | 1675(10) | 4985(6) | 5845(4) | 57(2) |
| C(30) | 1676(13) | 5507(6) | 6397(5) | 73(2) |
| C(38) | 1829(14) | 2307(7) | 5543(5) | 87(3) |
| C(32) | 4177(12) | 5857(6) | 6447(4) | 62(2) |
| C(37) | 1212(13) | 1993(6) | 4941(5) | 78(3) |
| C(31) | 2903(15) | 5910(7) | 6692(5) | 82(3) |
| N(7) | 4371(6) | 5572(4) | 3879(3) | 39(1) |
| N(5) | 3496(6) | 4583(4) | 4522(3) | 40(1) |
| N(6) | 5540(8) | 5326(4) | 5672(3) | 52(2) |
| C(42) | 6922(10) | 5333(7) | 6176(4) | 70(3) |
| O(4) | 6769(6) | 5366(4) | 4854(3) | 61(2) |
| O(5) | 1990(5) | 5881(3) | 3468(2) | 47(1) |
| C(43) | 3254(7) | 5799(5) | 3385(3) | 37(2) |
| C(44) | 3604(7) | 5919(5) | 2715(3) | 38(2) |
| C(48) | 2633(7) | 5381(5) | 2189(3) | 39(2) |
| C(45) | 3372(8) | 6832(5) | 2508(3) | 42(2) |
| C(47) | 4193(9) | 8255(6) | 2732(6) | 68(3) |
| C(49) | 2530(8) | 4500(5) | 2392(4) | 47(2) |
| C(46) | 4402(9) | 7411(5) | 2964(4) | 48(2) |
| C(50) | 3935(11) | 4011(6) | 2526(5) | 64(2) |
| F(7) | 5101(7) | 8786(4) | 3126(4) | 96(2) |
| F(8) | 2886(6) | 8555(4) | 2680(4) | 93(2) |
| F(9) | 4504(7) | 8366(4) | 2111(3) | 82(2) |
| C(51) | 3205(7) | 5393(5) | 1551(3) | 43(2) |
| N(8) | 2237(6) | 5343(5) | 980(3) | 50(2) |
| O(6) | 4529(6) | 5406(6) | 1582(3) | 84(2) |
| C(52) | 3758(13) | 3148(6) | 2623(6) | 75(3) |
| F(12) | 4965(9) | 2712(5) | 2742(5) | 121(3) |
| F(11) | 2916(13) | 2808(5) | 2068(5) | 146(4) |
| F(10) | 3056(12) | 2973(5) | 3096(5) | 148(4) |

*U(eq) is defined as one third of the trace of the orthogonalized U$^{ij}$ tensor.

In still yet an even further embodiment, the THF-2 form of the compound of Example 1 is substantially pure.

In still yet another embodiment, the THF-2 form of the compound of Example 1 contains at least about 90 wt. %, preferably at least about 95 wt. %, and more preferably at least about 99 wt. %, based on weight of the fourth crystalline form, Form THF-2.

In yet another embodiment, a substantially pure Form THF-2 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially crystalline Form THF-2 has substantially pure phase homogeneity with less than about 1% of the total peak area of the experimentally measured PXRD pattern arising from peaks that are absent from the simulated PXRD pattern.

In another embodiment, the fourth crystalline form of the compound of Example 1 consists essentially of Form THF-2. The fourth crystalline form of this embodiment may comprise at least about 90 wt. %, preferably at least about 95 wt. %, and more preferably at least about 99 wt. %, based on the weight of the fourth crystalline form, Form THF-2.

Crystalline Form of the Compound of Example 2

In one embodiment, the compound of Example 2

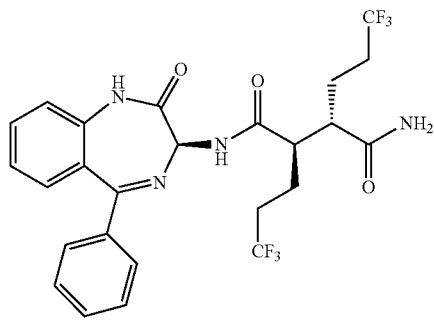 [SMILES: NC(=O)[C@@H](CCC(F)(F)F)[C@@H](CCC(F)(F)F)C(=O)N[C@H]1N=C(c2ccccc2)c2ccccc2NC1=O]

is provided as a crystalline material comprising a crystalline form. An example of a suitable crystalline form of the compound of Example 2 is Form M2-1. The M2-1 Form comprises about two methanol molecules for each molecule of Example 2.

In one embodiment, the M2-1 Form of compound of Example 2 is characterized by unit cell parameters approximately equal to the following:

Cell dimensions:
a=8.44 Å
b=21.02 Å
c=17.52 Å
α=90.0°
β=90.88°
γ=90.0°
Space group: P2$_1$
Molecules of Example 2/asymmetric unit: 2
Volume/Number of molecules in the unit cell=777 Å$^3$
Density (calculated)=1.297 g/cm$^3$, wherein the unit cell parameters of Form M-1 are measured at a temperature of about −100° C.

Figure 5:
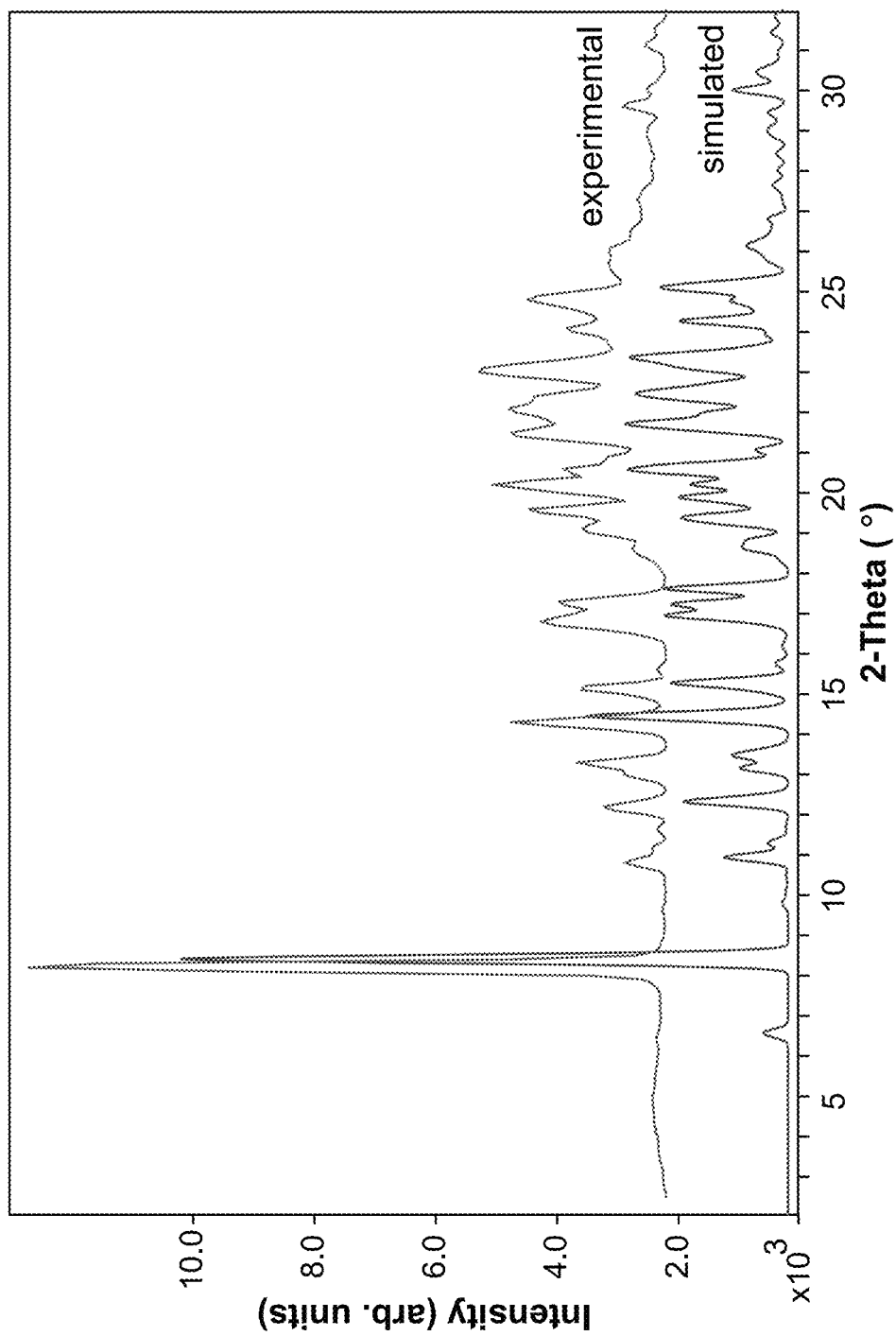
FIG. 5 shows the experimental (at approximately 25° C.) and the simulated (at approximately 25° C.) PXRD patterns (CuKα λ=1.5418 Å) of the M2-1 Form of the compound of Example 2.

In another embodiment, the M2-1 Form is characterized by a simulated powder x-ray diffraction (PXRD) pattern substantially in accordance with the pattern shown in FIG. 5 and/or by an observed PXRD pattern substantially in accordance with the pattern shown in FIG. 5.

In yet another embodiment, the M2-1 Form of the compound of Example 2 is characterized by a PXRD pattern (CuKα λ=1.5418 Å at a temperature of about 25° C.) comprising four or more, preferably five or more, 2θ values selected from: 8.2±0.2, 12.2±0.2, 14.2±0.2, 15.1±0.2, 16.8±0.2, 17.3±0.2, and 23.0±0.2, wherein the PXRD pattern of Form M2-1 is measured at a temperature of about 20° C.

In yet an even further embodiment, the M2-1 Form of Example 2 is characterized by fractional atomic coordinates substantially as listed in Table 5.

TABLE 5

Fractional Atomic Coordinates of Form M2-1 Calculated at a Temperature of about 25° C.; Atomic Coordinates (×10$^4$) and Equivalent Isotropic Displacement Parameters (Å$^2$ × 10$^3$) for Example 2, Form M2-1

|       | x        | y       | z        | U(eq)  |
|-------|----------|---------|----------|--------|
| F(1)  | 2613(2)  | −212(1) | 2456(1)  | 77(1)  |
| F(2)  | 4541(3)  | −625(1) | 3070(2)  | 96(1)  |
| F(3)  | 4934(3)  | −161(1) | 2004(1)  | 96(1)  |
| F(4)  | 7167(3)  | 3758(1) | 3848(1)  | 77(1)  |
| F(5)  | 6914(3)  | 3210(1) | 4862(1)  | 90(1)  |
| F(6)  | 9215(3)  | 3403(1) | 4441(1)  | 85(1)  |
| F(7)  | 7591(2)  | 3726(1) | 11734(2) | 119(1) |
| F(8)  | 9635(3)  | 4107(1) | 11204(1) | 86(1)  |
| F(9)  | 9848(3)  | 3673(1) | 12297(1) | 79(1)  |
| F(10) | 12277(3) | −275(1) | 10384(1) | 91(1)  |
| F(11) | 11834(6) | 315(1)  | 9441(2)  | 176(2) |
| F(12) | 14222(4) | 122(1)  | 9816(2)  | 133(1) |
| O(1)  | 1635(2)  | 931(1)  | 4421(1)  | 37(1)  |
| O(2)  | 5968(2)  | 825(1)  | 4908(1)  | 47(1)  |
| O(3)  | 8139(2)  | 1682(1) | 2398(1)  | 35(1)  |
| O(4)  | 6559(2)  | 2497(1) | 9963(1)  | 39(1)  |
| O(5)  | 10872(2) | 2663(1) | 9445(1)  | 39(1)  |
| O(6)  | 13114(2) | 1784(1) | 11956(1) | 34(1)  |
| N(1)  | 2751(2)  | 2232(1) | 5319(1)  | 34(1)  |
| N(2)  | 1067(2)  | 1032(1) | 5670(1)  | 33(1)  |
| N(3)  | 4363(2)  | 1622(1) | 4536(1)  | 30(1)  |
| N(4)  | 10420(2) | 1368(1) | 2964(1)  | 37(1)  |
| N(5)  | 7664(2)  | 1284(1) | 8920(1)  | 33(1)  |
| N(6)  | 5929(2)  | 2493(1) | 8710(1)  | 31(1)  |
| N(7)  | 9312(2)  | 1845(1) | 9778(1)  | 31(1)  |
| N(8)  | 15396(2) | 2076(1) | 11411(1) | 40(1)  |
| C(1)  | 1345(3)  | 1256(1) | 6422(1)  | 35(1)  |
| C(2)  | 1849(3)  | 1874(1) | 6578(1)  | 36(1)  |
| C(3)  | 2048(3)  | 2059(2) | 7348(2)  | 45(1)  |
| C(4)  | 1720(3)  | 1644(2) | 7931(2)  | 55(1)  |
| C(5)  | 1161(3)  | 1038(2) | 7766(2)  | 56(1)  |
| C(6)  | 981(3)   | 842(2)  | 7018(2)  | 44(1)  |
| C(7)  | 2098(3)  | 2347(1) | 5969(1)  | 35(1)  |
| C(8)  | 1531(3)  | 3012(1) | 6086(2)  | 40(1)  |
| C(9)  | 2312(4)  | 3514(2) | 5740(2)  | 51(1)  |
| C(10) | 1764(5)  | 4131(2) | 5823(2)  | 65(1)  |
| C(11) | 428(5)   | 4245(2) | 6243(3)  | 80(1)  |
| C(12) | −352(5)  | 3754(2) | 6580(3)  | 80(1)  |
| C(13) | 191(4)   | 3139(2) | 6513(2)  | 56(1)  |
| C(14) | 1961(3)  | 1152(1) | 5056(1)  | 30(1)  |
| C(15) | 3364(3)  | 1594(1) | 5200(1)  | 31(1)  |
| C(16) | 5555(3)  | 1219(1) | 4426(1)  | 30(1)  |
| C(17) | 6342(3)  | 1256(1) | 3652(1)  | 28(1)  |
| C(18) | 8095(3)  | 1450(1) | 3748(1)  | 31(1)  |
| C(19) | 8887(3)  | 1501(1) | 2979(1)  | 29(1)  |
| C(20) | 6151(3)  | 613(1)  | 3254(2)  | 36(1)  |
| C(21) | 4416(3)  | 482(1)  | 3060(2)  | 39(1)  |
| C(22) | 4138(4)  | −124(2) | 2655(2)  | 56(1)  |
| C(23) | 8335(3)  | 2081(1) | 4176(1)  | 34(1)  |
| C(24) | 7670(3)  | 2664(1) | 3763(2)  | 39(1)  |
| C(25) | 7738(4)  | 3248(2) | 4225(2)  | 50(1)  |
| C(26) | 6216(3)  | 2346(1) | 7935(1)  | 29(1)  |
| C(27) | 6745(3)  | 1743(1) | 7708(1)  | 29(1)  |
| C(28) | 6963(3)  | 1642(1) | 6922(1)  | 37(1)  |
| C(29) | 6629(3)  | 2113(2) | 6398(2)  | 46(1)  |
| C(30) | 6065(3)  | 2691(2) | 6633(2)  | 46(1)  |
| C(31) | 5856(3)  | 2812(1) | 7399(2)  | 39(1)  |
| C(32) | 6994(3)  | 1217(1) | 8261(1)  | 30(1)  |
| C(33) | 6421(3)  | 571(1)  | 8051(2)  | 35(1)  |
| C(34) | 7176(4)  | 43(1)   | 8360(2)  | 49(1)  |
| C(35) | 6628(4)  | −563(2) | 8178(2)  | 62(1)  |
| C(36) | 5318(4)  | −640(2) | 7705(2)  | 63(1)  |
| C(37) | 4561(4)  | −123(2) | 7405(2)  | 59(1)  |
| C(38) | 5104(3)  | 486(1)  | 7577(2)  | 45(1)  |
| C(39) | 6856(3)  | 2328(1) | 9310(1)  | 30(1)  |
| C(40) | 8266(3)  | 1907(1) | 9119(1)  | 30(1)  |
| C(41) | 10484(3) | 2259(1) | 9915(1)  | 30(1)  |
| C(42) | 11305(3) | 2212(1) | 10692(1) | 29(1)  |
| C(43) | 13053(3) | 2027(1) | 10608(1) | 28(1)  |
| C(44) | 13850(3) | 1958(1) | 11389(1) | 27(1)  |
| C(45) | 11115(3) | 2854(1) | 11089(1) | 33(1)  |
| C(46) | 9380(3)  | 2999(1) | 11248(2) | 44(1)  |
| C(47) | 9111(4)  | 3620(2) | 11616(2) | 59(1)  |
| C(48) | 13303(3) | 1408(1) | 10152(1) | 37(1)  |
| C(49) | 12699(4) | 817(1)  | 10535(2) | 46(1)  |
| C(50) | 12765(6) | 249(2)  | 10046(2) | 71(1)  |
| O(1S) | 3445(3)  | 3322(1) | 8972(1)  | 65(1)  |

TABLE 5-continued

Fractional Atomic Coordinates of Form M2-1 Calculated at a
Temperature of about 25° C.; Atomic Coordinates (×10⁴)
and Equivalent Isotropic Displacement Parameters (Å² × 10³)
for Example 2, Form M2-1

| | x | y | z | U(eq) |
|---|---|---|---|---|
| O(2S) | 3658(2) | 2451(1) | 3295(1) | 43(1) |
| O(3S) | 8681(2) | 1043(1) | 1039(1) | 51(1) |
| C(4S) | 2039(4) | 4719(2) | 3916(2) | 64(1) |
| C(1S) | 3853(6) | 3821(2) | 9485(3) | 123(2) |
| C(2S) | 2594(4) | 2953(2) | 3435(2) | 59(1) |
| C(3S) | 7938(7) | 447(2) | 954(3) | 107(2) |
| O(4S) | 1606(03) | 5269(1) | 4324(2) | 63(1) |

U(eq) is defined as one third of the trace of the orthogonalized $U^{ij}$ tensor.

In still yet an even further embodiment, the M2-1 form of the compound of Example 2 is substantially pure.

In still yet another embodiment, the M2-1 form of the compound of Example 2 contains at least about 90 wt. %, preferably at least about 95 wt. %, and more preferably at least about 99 wt. %, based on weight of the crystalline form, Form M2-1.

In yet another embodiment, a substantially pure crystalline form of Form M2-1 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure crystalline form of M2-1 has substantially pure phase homogeneity with less than about 1% of the total peak area of the experimentally measured PXRD pattern arising from peaks that are absent from the simulated PXRD pattern.

In another embodiment, the crystalline form of the compound of Example 2 consists essentially of Form M2-1. The crystalline form of this embodiment may comprise at least about 90 wt. %, preferably at least about 95 wt. %, and more preferably at least about 99 wt. %, based on the weight of the crystalline form, Form M2-1.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising the compound of Formula (I) or prodrug thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropylmethylcellulose and hydroxypropylcellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethylcellulose, sodium alginate, alginic acid, polyvinylpyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I), or a prodrug thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I) or a prodrug thereof. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment. The method of this embodiment includes the administration of the compound having the structure:

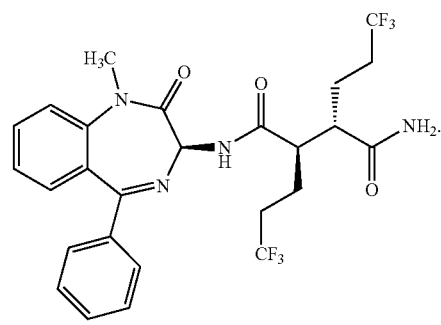 [SMILES: CN1C(=O)[C@@H](NC(=O)[C@H](CCC(F)(F)F)[C@H](CCC(F)(F)F)C(N)=O)N=C(c2ccccc2)c2ccccc21]

The method of this embodiment also includes the administration of the compound having the structure:

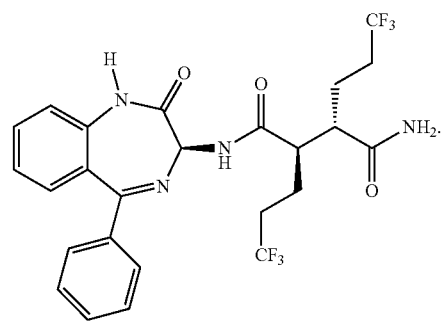 [SMILES: NC(=O)[C@@H](CCC(F)(F)F)[C@@H](CCC(F)(F)F)C(=O)N[C@H]1N=C(c2ccccc2)c2ccccc2NC1=O]

Routes of administration in the present embodiment include parenteral administration and oral administration.

In one embodiment, a method is provided for treating cancer comprising administering to a mammal in need thereof a compound of Formula (I) or a prodrug thereof, wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a prodrug thereof, wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a prodrug thereof, wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a prodrug thereof, wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a prodrug thereof, wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof a compound of Formula (I) or a prodrug thereof, wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of a compound of Formula (I) or a prodrug thereof, in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment provides a compound of Formula (I) or a prodrug thereof, for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient a compound of Formula (I) or a prodrug thereof. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof a compound of Formula (I) or a prodrug thereof; and administering one or more additional anti-cancer agents.

The phrase "additional anti-cancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of a compound of Formula (I) or prodrug thereof in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof a compound of Formula (I) or a prodrug thereof; administering dasatinib; and optionally, one or more additional anti-cancer agents.

In one embodiment, a method is provided for treating cancer comprising administering to a mammal in need thereof a compound of Formula (I) or a prodrug thereof; administering paclitaxel; and optionally, one or more additional anti-cancer agents.

In one embodiment, a method is provided for treating cancer comprising administering to a mammal in need thereof a compound of Formula (I) or a prodrug thereof; administering Tamoxifen; and optionally, one or more additional anti-cancer agents.

In one embodiment, a method is provided for treating cancer comprising administering to a mammal in need thereof a compound of Formula (I) or a prodrug thereof; administering a glucocorticoid; and optionally, one or more additional anti-cancer agents. An example of a suitable glucocorticoid is dexamethasone.

In one embodiment, a method is provided for treating cancer comprising administering to a mammal in need thereof a compound of Formula (I) or a prodrug thereof; administering carboplatin; and optionally, one or more additional anti-cancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising a compound of Formula (I) or prodrug thereof; one or more additional agents selected from a kinase inhibitory agent (small molecule, polypeptide, and antibody), an immunosuppressant, an anti-cancer agent, an anti-viral agent, anti-inflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the compound of Formula (I) is administered continuously to a patient in need thereof, one or more times daily. For example, a therapeutically effective amount of the compound of Formula (I) is administered to a patient in need thereof, one or more times daily for continuous days.

In one embodiment, the compound of Formula (I) is administered intermittently to a patient in need thereof, one or more times daily. For example, a therapeutically effective amount of the compound of Formula (I) is administered to a patient in need thereof, one or more times daily according to an intermittent schedule.

In one embodiment, the compound of Formula (I) is administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, the compound of Formula (I) is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, the compound of Formula (I) is administered on one day, followed by 6 days of rest, and repeated on a weekly schedule.

In one embodiment, the compound of Formula (I) is administered on two consecutive days, followed by 5 days of rest, and repeated on a weekly schedule.

In one embodiment, the compound of Formula (I) is administered on three consecutive days followed by four days of rest, and repeated on a weekly schedule.

In one embodiment, the compound of Formula (I) is administered on one day, followed by 10 to 13 days of rest.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 5.

Scheme 1

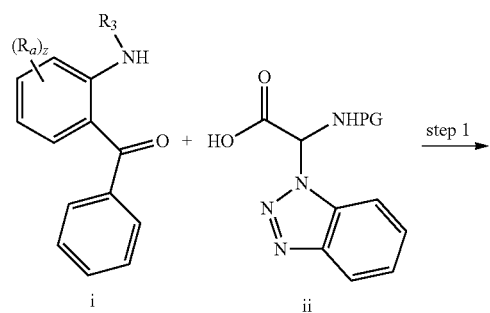

-continued

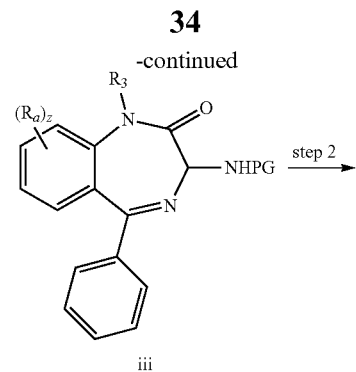

iii

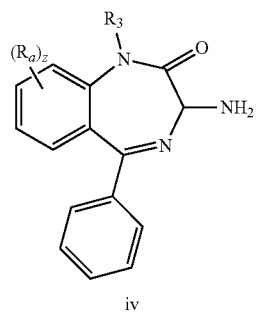

iv

The preparation of benzodiazepinone (iv) may be accomplished in multitude of methods known to one skilled in the art. For example, as shown in Scheme 1, an appropriately substituted 2-aminobenzophenone (i) (for example, from Walsh, D. A., *Synthesis*, 677 (1980); and references cited therein, or other methods known to one skilled in the art) may be coupled to the protected glycine derivative (ii) (PG=protecting group, for example PG=CBz, see Katritzky, A. R., *J. Org. Chem.*, 55:2206-2214 (1990)), treated with a reagent such as ammonia and subjected to cyclization to afford the benzodiazepinone (iii), according to the procedure outlined in the literature (for example Sherrill, R. G. et al., *J. Org. Chem.*, 60:730 (1995); or other routes known to one skilled in the art). The resulting racemic mixture may be separated (using procedures known to one skilled in the art) to get the individual enantiomers, or used as a racemate. Also, if $R_3$=H, (iii) may be, for example, treated with a reagent such as MeI and a base such as $K_2CO_3$ in a solvent such as DMF to prepare $R_3$=Me.

Step 2: The deprotection of (iii) may be accomplished in several ways known to one skilled in the art. For example, with PG=CBz, Compound (iii) may be treated with a reagent such as HBr in a solvent such as AcOH. Compound (iv) may be used as a racemate. Alternatively, compound (iv) may be subjected to enantiomeric resolution using standard methods (e.g., chiral preparative chromatography).

Scheme 2
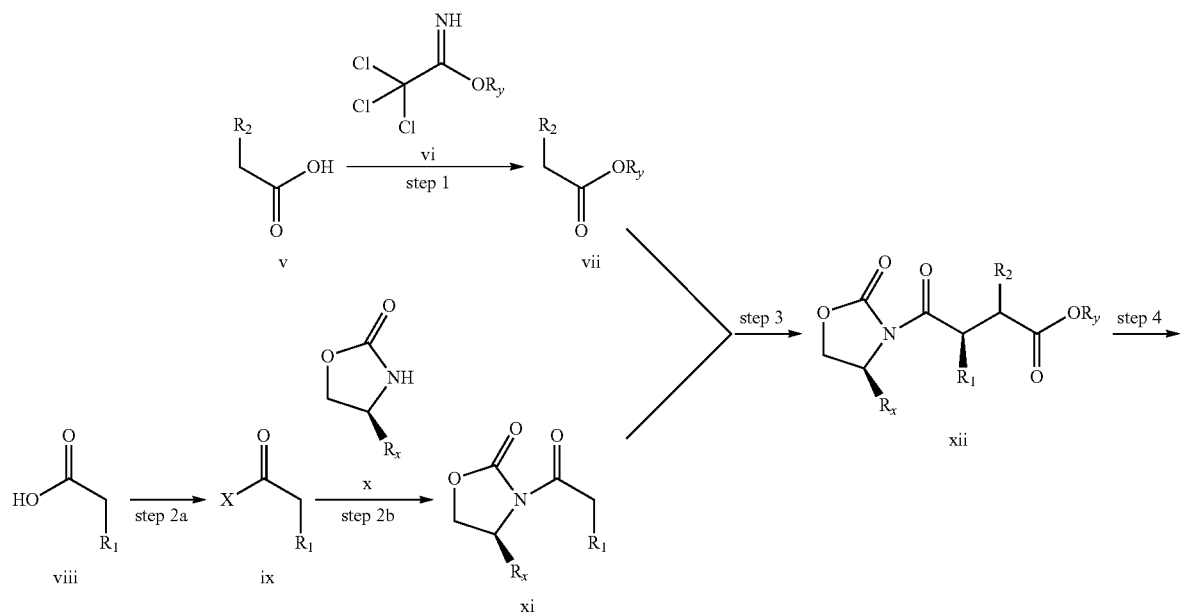
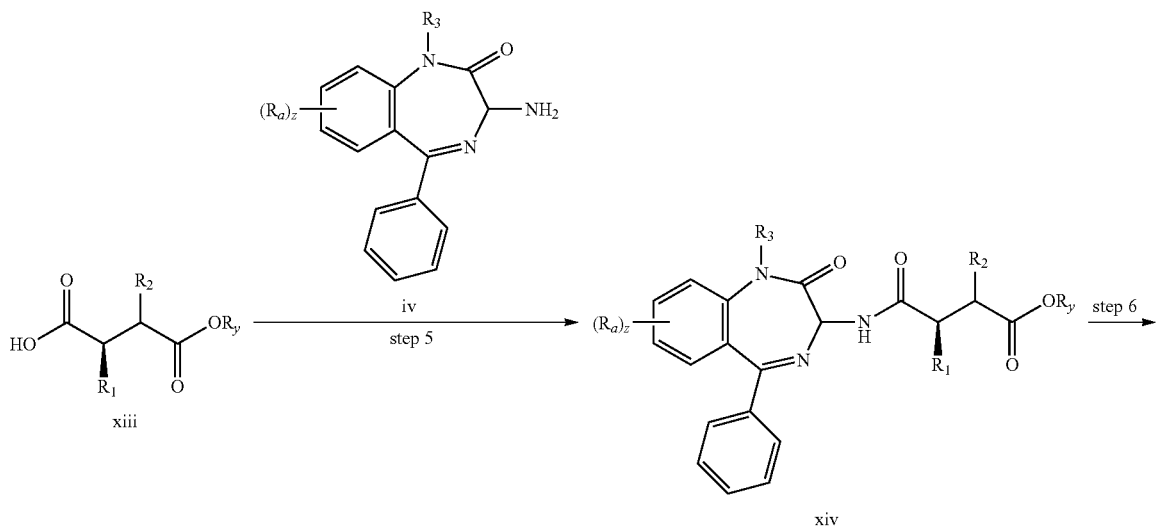
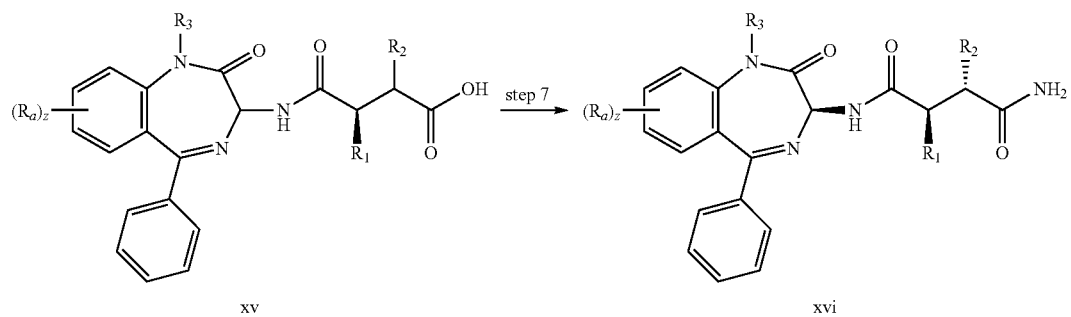

Step 1: The first step of Scheme 2 is accomplished by converting compound (v) to the ester (vii), employing one of the multiple ways known to one skilled in the art, such as treatment with a substituted acetimidate such as compound (vi) in the presence of a reagent such as boron trifluoride etherate at an appropriate temperature in a solvent such as THF.

Step 2: Acid (viii) can be converted to compound (ix) in multiple ways known to one skilled in the art. For example, treatment of acid (viii) with a reagent such as oxalyl chloride in a solvent such as DCM gives the acid chloride (ix). Compound (ix) can be treated with an oxazolidinone (x) under standard conditions to give compound (xi) (Evans, D. A. et al., *J. Am. Chem Soc.*, 112:4011 (1990)).

Step 3: Compound (xi) can be converted to compound (xii) in multiple ways (Baran, P. et al., *J. Am. Chem. Soc.*, 130(34): 11546 (2008)). For example, compound (vii) is treated with a base such as LDA in a solvent such as toluene, at low temperature such as −78° C. under an inert atmosphere such as $N_2$. The resulting mixture is added to a solution of compound (xi) treated with lithium chloride and a base such as LDA in a solvent such as toluene under an inert atmosphere such as $N_2$. To the resulting mixture of the enolates of compounds (vii) and (xi) is added a compound, such as bis(2-ethylhexanoyloxy)copper, at a low temperature such as −78° C. under an inert atmosphere such as $N_2$ and warmed to room temperature to provide compound (xii).

Step 4: Conversion of compound (xii) to (xiii) may be accomplished by treating it with reagents such as hydrogen peroxide and lithium hydroxide at an appropriate temperature, using a mixture of solvents such as THF/water. If necessary, the diastereoisomers may be separated at this point via silica gel chromatography or preparative HPLC. Alternately, the mixture may be subjected to epimerization conditions, for example by treatment with LDA and diethylaluminum chloride followed by quenching with methanol or acetic acid to enrich the desired diastereoisomer.

Step 5: Compound (xiii) may be coupled with benzodiazepinone (iv) in the presence of a coupling reagent such as TBTU and a base such as TEA, in a solvent such as DMF to provide compound (xiv).

Step 6: Treatment of compound (xiv) with an acid such as TFA at an appropriate temperature such as 0° C., in a solvent such as DCM provides compound (xv).

Step 7: Conversion of compound (xv) to compound (xvi) may be accomplished via coupling of compound (xv) with an appropriate amine source such as ammonium chloride, a carbodiimide such as EDC, HOBT and a base such as TEA in a solvent such as DMF. If necessary the diastereoisomeric mixture can be separated using an appropriate separation technique, such as chiral preparative chromatography.

Scheme 3

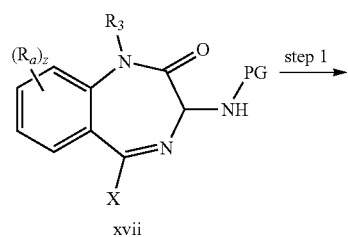

xvii

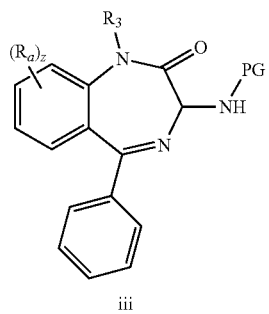

iii

Step 1: The preparation of benzodiazepinone (iii) may also be accomplished by cross coupling of benzodiazepinone (xvii) containing a halogen atom such as chlorine (X═Cl) and a protecting group (PG) such as Boc, with an appropriate coupling partner such as a boronic acid under conditions known to one skilled in the art. For example, the coupling of the halogen containing moiety with a boronic acid occurs in the presence of a catalyst such as tetrakis(triphenylphosphine)palladium(0), a base such as sodium carbonate and a solvent such as DME under an inert atmosphere such as $N_2$.

Scheme 4

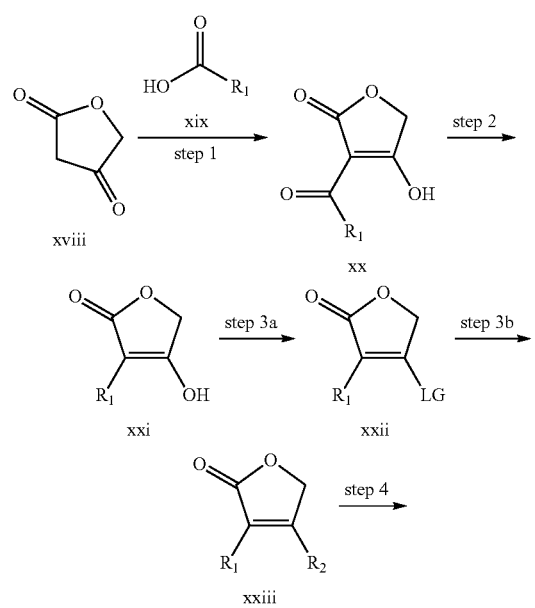

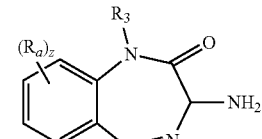

xxiii

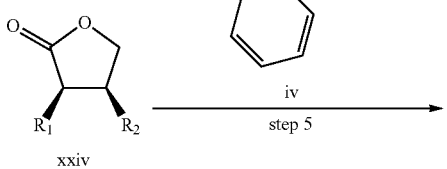

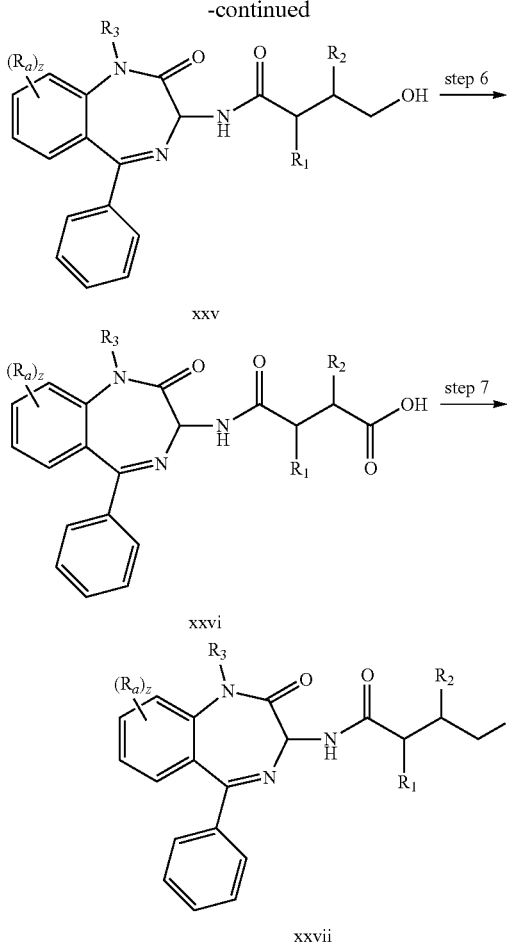

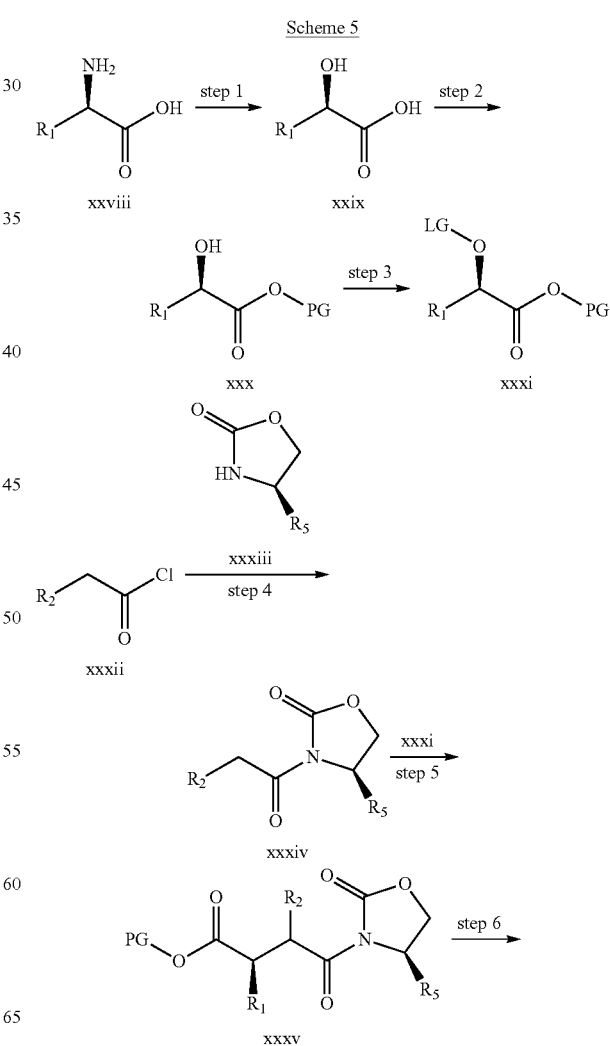

Step 5: Compound (xxv) may be obtained by the coupling of Compound (xxiv) with Compound (iv). For example, the transformation may be accomplished with the use of a reagent such as AlMe$_3$ in a solvent such as DCM under an inert atmosphere such as N$_2$. At this instance the mixture of diastereoisomers obtained may be used as a mixture or may be separated by an appropriate method such as chiral chromatography.

Step 6: Compound (xxv) is oxidized using an oxidizing agent such as Jones reagent, in a solvent such as acetone to give Compound (xxvi). If the compound is a diastereoisomeric mixture then it may be used as a mixture or may be separated using an appropriate method such as chiral chromatography.

Step 7: Conversion of Compound (xxvi) to Compound (xxvii) may be accomplished via standard procedures known to one skilled in the art. For example, coupling of Compound (xxvi) with an appropriate amine source such as ammonium chloride, a carbodiimide such as EDC, HOBT and a base such as TEA in a solvent such as DMF provides Compound (xxvii). At this instance the compound may be enantiopure or if necessary the diastereoisomeric mixture can be separated using an appropriate separation technique, such as chiral chromatography.

Step 1: The first step of Scheme 4 involves the treatment of Compound (xvii) with carboxylic acid (xix) in the presence of a carbodiimide such as DCC, a base such as TEA, and a catalyst such as DMAP in a solvent such as DCM provides Compound (xx).

Step 2: Conversion of Compound (xx) to Compound (xxi) may be accomplished by treatment with a reagent such as sodium cyanoborohydride in the presence of an acid such as HCl under atmospheric conditions that may be inert, for example under N$_2$.

Step 3: Conversion of Compound (xxi) to Compound (xxiii) may proceed via Compound (xxii) bearing an appropriate leaving group (LG). For example, treatment of Compound (xxi) with a base such as 2,6-lutidine and a reagent such as trifluoromethanesulfonic anhydride in a solvent such as DCM at an appropriate temperature such as −78° C., provides the triflate of Compound (xxii). Compound (xxii) may now be subjected to cross coupling reaction conditions to provide Compound (xxiii). For example, treatment of Compound (xxii) with an appropriately substituted coupling partner, for example a boronic acid, in the presence of a catalyst such as tetrakis(triphenylphosphine)palladium(0), a base such as potassium phosphate in a solvent such as dioxane under atmospheric conditions that may be inert, for example under N$_2$, provides Compound (xxiii).

Step 4: Conversion of Compound (xxiii) to Compound (xxiv) may be accomplished via standard procedures known to one skilled in the art. For example, treatment of Compound (xxiii) in the presence of a catalyst such as Pd/C in a solvent such as methanol gives Compound (xxiv).

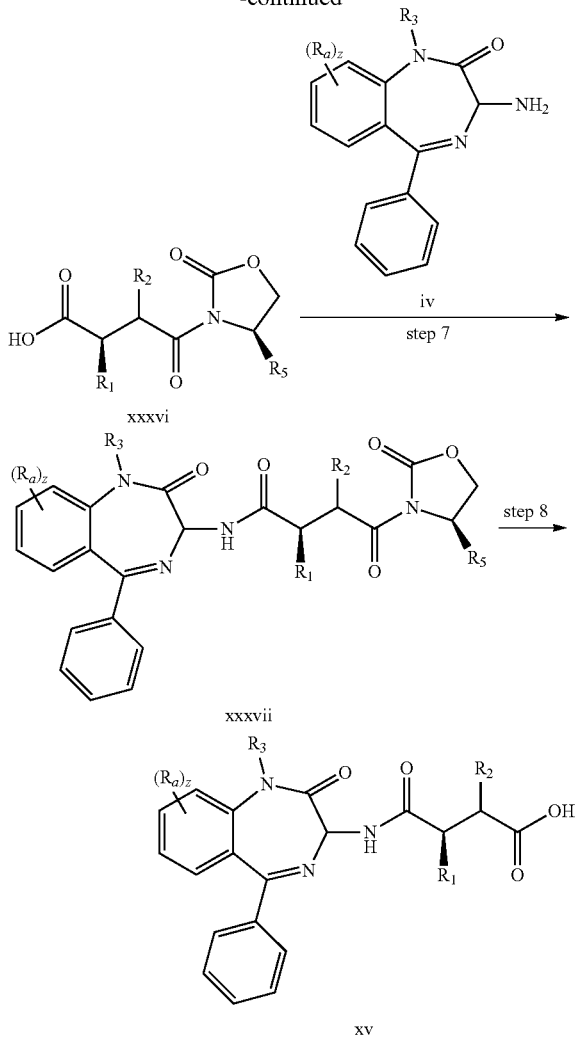

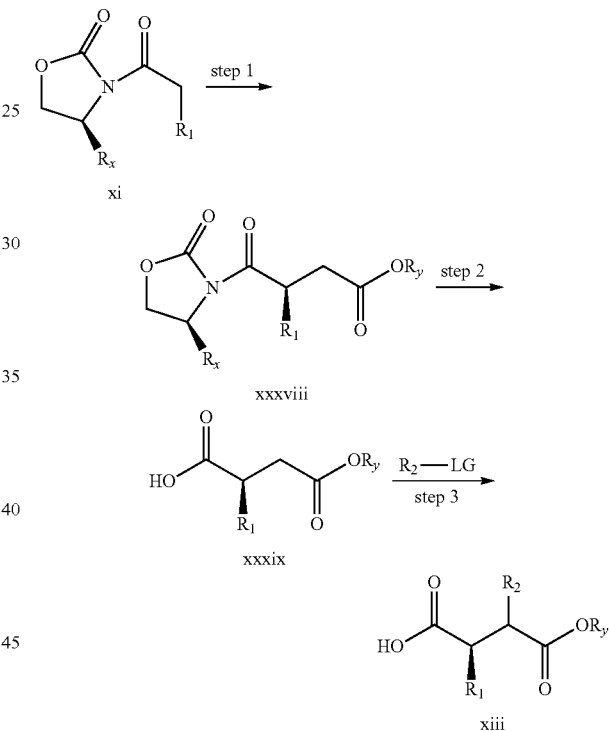

Step 1: The first step of Scheme 5 is accomplished by treating Compound (xxviii) with a reagent such as sodium nitrite in an acid such as $H_2SO_4$ and a solvent such as water to provide Compound xxix.

Step 2: The acid (xxix) is converted to compound (xxx) (PG=protecting group). For example, the acid (xxix) is treated with an alcohol such as benzyl alcohol in a solvent such as toluene and an acid such as $H_2SO_4$ to provide Compound xxx.

Step 3: Compound (xxxi) bearing a suitable leaving group may be prepared by treatment of Compound (xxx) with a base such as 2,6-lutidine and a reagent such as trifluoromethanesulfonic anhydride in a solvent such as DCM at an appropriate temperature.

Step 4: Compound (xxxii) can be converted to Compound (xxxiv) in multiple ways known to one skilled in the art. For example, treatment of acid chloride (xxxii), either prepared from the corresponding carboxylic acid with a reagent such as oxalyl chloride in a solvent such as DCM, or obtained commercially, can be treated with an oxazolidinone (xxxiii) under standard conditions to give Compound (xxxiv) (Evans, D. A. et al., J. Am. Chem. Soc., 112:4011 (1990)).

Step 5: The preparation of Compound (xxxv) may be effected by treating Compound (xxxiv) with a base such as LiHMDS in a solvent such as THF at an appropriate temperature such as −78° C. and to the resulting mixture is added Compound (xxxi) in a solvent such as THF.

Step 6: The protecting group of Compound (xxxv) may be removed via many methods known to one skilled in the art. For example, a benzyl group may be removed by subjecting it to hydrogenation conditions using a palladium catalyst such as Pearlman's Catalyst in a solvent such as methanol to provide Compound (xxxvi).

Step 7: Compound (iv) is coupled with Compound (xxxvi) in the presence of a coupling reagent such as TBTU and a base such as TEA in a solvent such as DMF to provide Compound (xxxvii). If necessary, the diastereoisomers may be separated using an appropriate method such as chiral preparative chromatography.

Step 8: The hydrolysis of Compound (xxxvii) may be accomplished by treating it with hydrogen peroxide and lithium hydroxide at an appropriate temperature using a mixture of solvents such as THF/water to give Compound (xv). If necessary, the diastereoisomers may be separated using an appropriate method such as chiral preparative chromatography.

Scheme 6

Compound (xiii) in Scheme 2 may also be prepared from compound (xi) by synthetic sequence outlined in Scheme 6.

Step 1: The first step of Scheme 6 is accomplished by treating Compound (xi) with a base such as sodium bis(trimethylsilyl)amide in a solvent such as THF at low temperature such as −78° C. under an inert atmosphere. To the resulting enolate of (xi) is treated with a reagent such as tert-butyl bromoacetate to provide compound (xxxviii).

Step 2: Conversion of compound (xxxviii) to (xxxix) may be accomplished by treating compound (xxxviii) with reagents such as hydrogen peroxide and lithium hydroxide at an appropriate temperature using a mixture of solvents such as THF/water.

Step 3: Compound (xxxix) can be converted to compound (xiii) by generating the enolate of (xxxix) with a base such as LDA in a solvent such as THF at low temperature such as −78° C. under an inert atmosphere and further treatment with a reagent ($R_2$-LG) bearing an appropriate leaving group (e.g., LG=triflate).

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

AcOH acetic acid
ACN acetonitrile
AlMe₃ trimethyl aluminum
Boc tert-butyloxycarbonyl
DCC 1,3-dicyclohexylcarbodiimide
DCM dichloromethane
DEA diethylamine
DMAP dimethylaminopyridine
DME dimethyl ether
DMF dimethylformamide
DMSO dimethyl sulfoxide
EDC 1-(3-dimethylaminopropyl)-3-ethylcarbodiimide hydrochloride
EDCI 1-(3-dimethylaminopropyl)-3-ethylcarbodiimide
Et₂AlCl diethyl aluminum chloride
EtOAc ethyl acetate
H₂SO₄ sulfuric acid
HCl hydrochloric acid
HOBT hydroxybenzotriazole
HPLC High Performance Liquid Chromatography
hr hour(s)
IPA isopropyl alcohol
LCMS Liquid Chromatography-Mass Spectroscopy
LDA lithium diisopropylamide
LiHMDS lithium bis(trimethylsilyl)amide
Me methyl
MeOH methanol
min minute(s)
MTBE methyl tert-butyl ether
N₂ nitrogen
NaHMDS sodium bis(trimethylsilyl)amide
Pd/C palladium on carbon
Ph phenyl
RT retention time
sat saturated
TBTU O-(1H-benzotriazol-1-yl)-N,N,N',N'-tetramethyluronium tetrafluoroborate
TEA triethylamine
Tf₂κ trifluoromethylsulfonic anhydride
TFA trifluoroacetic acid
THF tetrahydrofuran

Example 1

(2R,3S)—N-((3S)-1-Methyl-2-oxo-5-phenyl-2,3-dihydro-1H-1,4-benzodiazepin-3-yl)-2,3-bis(3,3,3-trifluoropropyl)succinamide

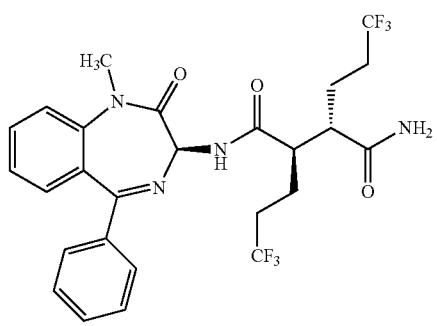

Preparation 1A: tert-Butyl 5,5,5-trifluoropentanoate

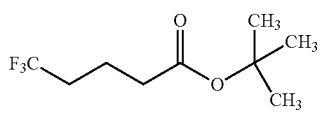

To a stirred solution of 5,5,5-trifluoropentanoic acid (5 g, 32.0 mmol) in THF (30 mL) and hexane (30 mL) at 0° C., was added tert-butyl 2,2,2-trichloroacetimidate (11.46 mL, 64.1 mmol). The mixture was stirred for 15 min at 0° C. Boron trifluoride etherate (0.406 mL, 3.20 mmol) was added and the reaction mixture was allowed to warm to room temperature overnight. To the clear reaction mixture was added solid NaHCO₃ (5 g) and stirred for 30 min. The mixture was filtered through MgSO₄ and washed with hexanes (200 mL). The solution was allowed to rest for 45 min, and the resulting solid material was removed by filtering on the same MgSO₄ filter again, washed with hexanes (100 mL) and concentrated under reduced pressure without heat. The volume was reduced to about 30 mL, filtered through a clean fritted funnel, washed with hexane (5 mL), and then concentrated under reduced pressure without heat. The resulting neat oil was filtered through a 0.45 μm nylon membrane filter disk to provide tert-butyl 5,5,5-trifluoropentanoate (6.6 g, 31.4 mmol 98% yield) as a colorless oil: ¹H NMR (400 MHz, CDCl₃) δ ppm 1.38 (s, 9H) 1.74-1.83 (m, 2H) 2.00-2.13 (m, 2H) 2.24 (t, J=7.28 Hz, 2H).

Preparation 1B: (4S)-4-(Propan-2-yl)-3-(5,5,5-trifluoropentanoyl)-1,3-oxazolidin-2-one

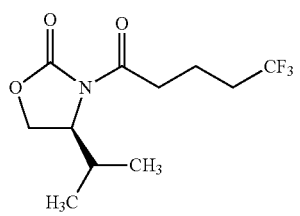

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min and the solution was stirred until all bubbling subsided. The reaction mixture was concentrated under reduced pressure to give pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (2.5M in hexane) (13.0 mL, 32.5 mmol) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated NH$_4$Cl, and then extracted with EtOAc (2×). The combined organics were washed with brine, dried (Na$_2$SO$_4$), filtered and concentrated under reduced pressure. The crude material was purified by flash chromatography (Teledyne ISCO CombiFlash Rf, 5% to 60% solvent A/B=hexanes/EtOAc, REDISEP® SiO$_2$ 120 g). Concentration of appropriate fractions provided Preparation 1B (7.39 g, 86%) as a colorless oil: $^1$H NMR (400 MHz, CDCl$_3$) δ ppm 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Preparation 1C: (2S,3R)-tert-Butyl 6,6,6-trifluoro-3-((S)-4-isopropyl-2-oxooxazolidine-3-carbonyl)-2-(3,3,3-trifluoropropyl)hexanoate, and Preparation 1D: (2R,3R)-tert-Butyl 6,6,6-trifluoro-3-((S)-4-isopropyl-2-oxooxazolidine-3-carbonyl)-2-(3,3,3-trifluoropropyl)hexanoate

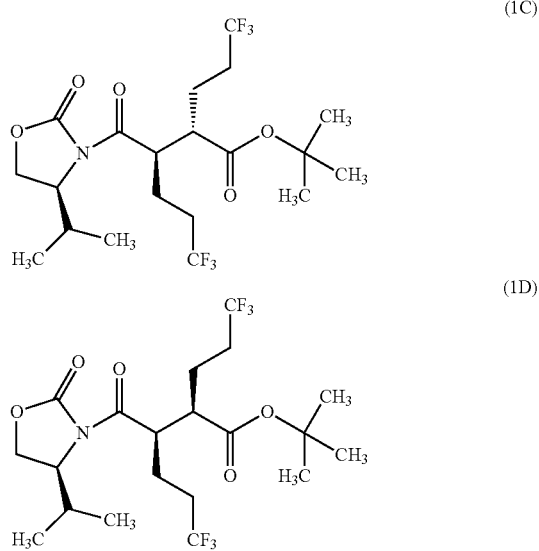

To a cold (−78° C.), stirred solution of diisopropylamine (5.3 mL, 37.2 mmol) in THF (59 mL) under nitrogen atmosphere was added n-BuLi (2.5M in hexane) (14.7 mL, 36.8 mmol), then warmed to 0° C. to give a 0.5M solution of LDA. A separate vessel was charged with Preparation 1B (2.45 g, 9.17 mmol), the material was azeotroped twice with benzene (the RotoVap air inlet was fitted with nitrogen inlet to completely exclude humidity) then toluene (15.3 mL) was added. This solution was added to a flask containing dry lithium chloride (1.96 g, 46.2 mmol). To the resultant mixture, cooled to −78° C., was added LDA solution (21.0 mL, 10.5 mmol) and stirred at −78° C. for 10 min, warmed to 0° C. for 10 min then recooled to −78° C. To a separate reaction vessel containing Preparation 1A (3.41 g, 16.07 mmol), also azeotroped twice with benzene, was added toluene (15.3 mL), cooled to −78° C. and LDA (37.0 mL, 18.5 mmol) was added, the resulting solution was stirred at −78° C. for 25 min. At this time the enolate derived from the ester was transferred via cannula into the solution of the oxazolidinone enolate, stirred at −78° C. for an additional 5 min at which time the septum was removed and solid powdered bis(2-ethylhexanoyloxy)copper (9.02 g, 25.8 mmol) was rapidly added to the reaction vessel and the septum replaced. The vessel was immediately removed from the cold bath and immersed into a warm water bath (40° C.) with rapid swirling with a concomitant color change from the initial turquoise to brown. The reaction mixture was stirred for 20 min, was poured into 5% aqueous NH$_4$OH (360 mL) and extracted with EtOAc (2×). The combined organics were washed with brine, dried (Na$_2$SO$_4$), filtered and concentrated under reduced pressure. The residue was purified by flash chromatography (Teledyne ISCO CombiFlash Rf, 0% to 60% solvent A/B=hexanes/EtOAc, REDISEP® SiO$_2$ 120 g). Concentration of appropriate fractions provided Preparation 1C (2.87 g, 66%) as pale yellow viscous oil. $^1$H NMR showed the product was a 1.6:1 mixture of diastereoisomers 1C:1D as determined by the integration of the multiplets at 2.74 & 2.84 ppm: $^1$H NMR (400 MHz, CDCl$_3$) δ ppm 4.43-4.54 (2H, m), 4.23-4.35 (5H, m), 4.01 (1H, ddd, J=9.54, 6.27, 3.51 Hz), 2.84 (1H, ddd, J=9.41, 7.28, 3.64 Hz), 2.74 (1H, ddd, J=10.29, 6.27, 4.02 Hz), 2.37-2.48 (2H, m, J=10.38, 6.98, 6.98, 3.51, 3.51 Hz), 2.20-2.37 (3H, m), 1.92-2.20 (8H, m), 1.64-1.91 (5H, m), 1.47 (18H, s), 0.88-0.98 (12H, m).

Preparation 1E: (2R,3S)-3-(tert-Butoxycarbonyl)-6,6,6-trifluoro-2-(3,3,3-trifluoropropyl)hexanoic acid, and Preparation 1F: (2R,3R)-3-(tert-Butoxycarbonyl)-6,6,6-trifluoro-2-(3,3,3-trifluoropropyl)hexanoic acid

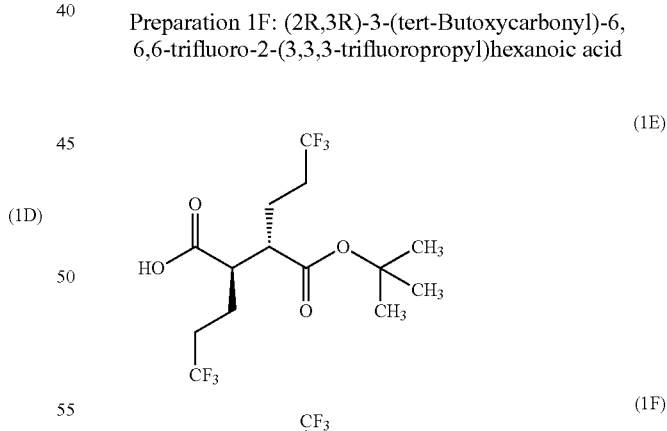

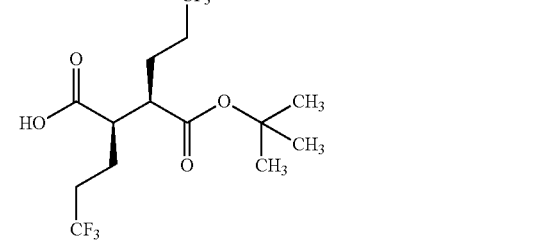

To a cool (0° C.), stirred solution of Preparation 1C and 1D (4.54 g, 9.51 mmol) in THF (140 mL) and water (42 mL) was sequentially added hydrogen peroxide (30% in water) (10.3 g, 91 mmol) and LiOH (685.3 mg, 28.6 mmol) and the mixture was stirred for 1 hr. At this time the reaction vessel was removed from the cold bath and then stirred for 1.5 hr. The reaction was judged complete by HPLC. To the reaction mixture was added saturated NaHCO$_3$ (45 mL) and saturated Na$_2$SO$_3$ (15 mL), and then partially concentrated under reduced pressure. The resulting crude solution was extracted with DCM (3×). The aqueous phase was acidified to pH~1-2 with 1N HCl, extracted with DCM (3×) and EtOAc (1×). The combined organics were washed with brine, dried (Na$_2$SO$_4$), filtered and concentrated under reduced pressure to provide a mixture of Preparation 1E and 1F (3.00 g, 86%) as colorless oil: $^1$H NMR (400 MHz, CDCl$_3$) δ ppm 2.76-2.84 (1H, m, diastereoisomer 2), 2.64-2.76 (3H, m), 2.04-2.35 (8H, m), 1.88-2.00 (4H, m), 1.71-1.83 (4H, m), 1.48 (9H, s, diastereoisomer 1), 1.46 (9H, s, diastereoisomer 2); $^1$H NMR showed a 1.7:1 mixture of 1E:1F by integration of the peaks for the t-butyl groups.

Preparation 1E: (2R,3S)-3-(tert-Butoxycarbonyl)-6,6,6-trifluoro-2-(3,3,3-trifluoropropyl)hexanoic acid, and Preparation 1F: (2R,3R)-3-(tert-Butoxycarbonyl)-6,6,6-trifluoro-2-(3,3,3-trifluoropropyl)hexanoic acid

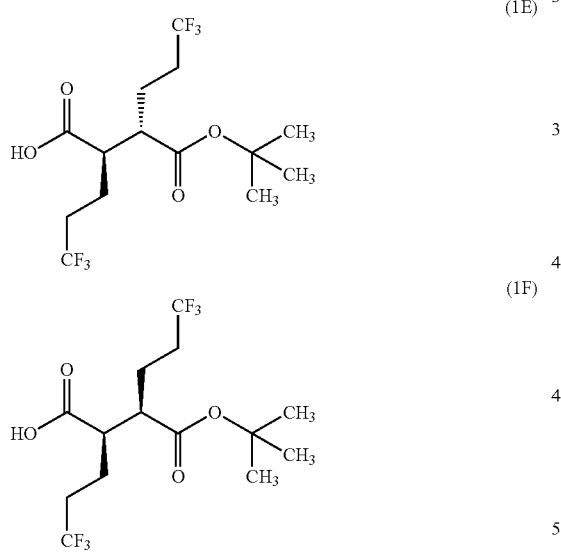

To a cold (−78° C.), stirred solution of diisopropylamine (1.7 mL, 11.93 mmol) in THF (19 mL) under nitrogen atmosphere was added n-BuLi (2.5M in hexanes) (4.8 mL, 12.00 mmol). The mixture was stirred for 5 min and then warmed to 0° C. In a separate vessel, to a cold (−78° C.) stirred solution of the mixture of Preparation 1E and 1F (1.99 g, 5.43 mmol) in THF (18 mL) was added the LDA solution prepared above via cannula slowly over 25 min. The mixture was stirred for 15 min, then warmed to room temperature (placed in a 24° C. water bath) for 15 min, and then again cooled to −78° C. for 15 min. To the reaction mixture was added Et$_2$AlCl (1M in hexane) (11.4 mL, 11.40 mmol) via syringe, stirred for 10 min, warmed to room temperature for 15 min and then cooled back to −78° C. for 15 min. Methanol (25 mL) was rapidly added, swirled vigorously while warming to room temperature, then concentrated to ~1/4 original volume. The mixture was dissolved in EtOAc and washed with 1N HCl (50 mL) and ice (75 g). The aqueous phase was separated, extracted with EtOAc (2×). The combined organics were washed with a mixture of KF (2.85 g in 75 mL water) and 1N HCl (13 mL) [resulting solution pH 3-4], then with brine, dried (Na$_2$SO$_4$), filtered and concentrated under reduced pressure to give a 9:1 (1E:1F) enriched diastereoisomeric mixture (as determined by $^1$H NMR) of Preparation 1E and Preparation 1F (2.13 g, >99%) as a pale yellow viscous oil: $^1$H NMR (400 MHz, CDCl$_3$) δ ppm 2.64-2.76 (2H, m), 2.04-2.35 (4H, m), 1.88-2.00 (2H, m), 1.71-1.83 (2H, m), 1.48 (9H, s).

Preparation 1G: (3S)-3-Amino-1-methyl-5-phenyl-1,3-dihydro-2H-1,4-benzodiazepin-2-one, and Preparation 1H: (3R)-3-Amino-1-methyl-5-phenyl-1,3-dihydro-2H-1,4-benzodiazepin-2-one

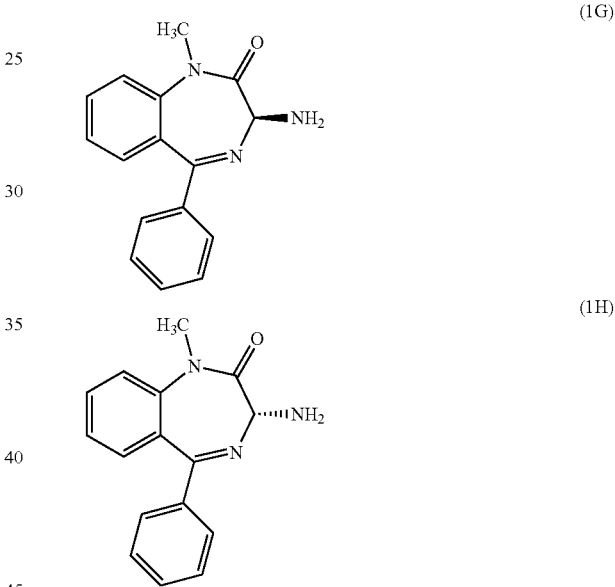

Racemic 3-amino-1-methyl-5-phenyl-1,3-dihydro-2H-1,4-benzodiazepin-2-one (Rittle, K. E. et al., *Tetrahedron Letters*, 28(5):521-522 (1987)) was prepared according to the literature procedure. The enantiomers were separated under chiral-SFC conditions using the following method: CHIRALPAK® AS-H 5×25; Mobile phase: 30% MeOH+0.1% DEA in CO$_2$; Flow rate: 280 mL/min; Pressure: 100 bar; Temperature: 35° C.

Obtained the S-enantiomer (Preparation 1G): HPLC: RT=1.75 min (30% MeOH+0.1% DEA in CO$_2$ on CHIRALPAK® AS-H 4.6×250 mm, 3 mL/min, 35° C., 100 bar, 230 nm, 10 µl injection); $^1$H NMR (400 MHz, CDCl$_3$) δ ppm 7.58-7.63 (2H, m), 7.55 (1H, ddd, J=8.50, 7.11, 1.76 Hz), 7.40-7.47 (1H, m), 7.34-7.40 (3H, m), 7.31 (1H, dd, J=7.81, 1.51 Hz), 7.14-7.22 (1H, m), 4.46 (1H, s), 3.44 (3H, s), 3.42 (2H, s); [α]$_D$=−155° (c=1.9, MeOH) (Lit. Rittle, K. E. et al., *Tetrahedron Letters*, 28(5):521-522 (1987): [α]$_D$=−236°).

Also obtained the R-enantiomer (Preparation 1H): HPLC: RT=1.71 min; [α]$_D$=+165° (c=2.1, MeOH) (Lit [α]$_D$=+227°).

Alternate Procedure to Make Preparation 1G

Preparation 1G.CSA salt: (3S)-3-Amino-1-methyl-5-phenyl-1,3-dihydro-2H-1,4-benzodiazepin-2-one, (1S)-(+)-10-camphorsulfonic acid salt

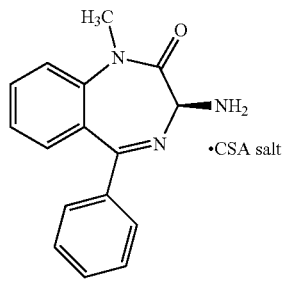

(1G·CSA)

Preparation 1G.CSA was prepared from racemic 3-amino-1-methyl-5-phenyl-1,3-dihydro-2H-1,4-benzodiazepin-2-one (9.98 g, 37.6 mmol) (prepared according to the literature as shown above) according to the literature procedure (Reider, P. J. et al., *J. Org. Chem.*, 52:955-957 (1987)). Preparation 1G.CSA (16.91 g, 99%) was obtained as a colorless solid: Optical Rotation: $[\alpha]_D=-26.99°$ (c=1, H$_2$O) (Lit. $[\alpha]_D=-27.8°$ (c=1, H$_2$O))

Preparation 1I: tert-Butyl (2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoate, and Preparation 1J: tert-Butyl (2R,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoate

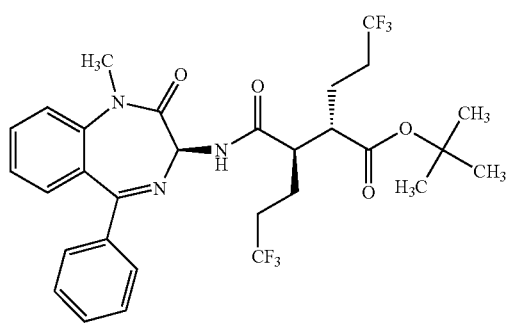

(1I)

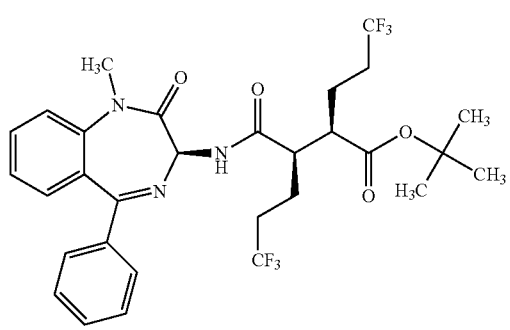

(1J)

To a stirred solution of Preparation 1G (1.45 g, 5.47 mmol) and a 9:1 mixture of Preparation 1E and 1F (1.989 g, 5.43 mmol) in DMF (19 mL) was added O-benzotriazol-1-yl-N, N,N',N'-tetra-methyluronium tetrafluoroborate (1.79 g, 5.57 mmol) and triethylamine (3.0 mL, 21.52 mmol) and stirred overnight. The reaction was judged complete by LCMS. The reaction mixture was poured into water (125 mL) and the precipitated solid was collected by filtration, washed with water and air dried to provide an 8:1 mixture of Preparation 1I and Preparation 1J (2.95 g, 89%) as a cream solid: MS (ES): m/z=614 [M+H]$^+$; $^1$H NMR (400 MHz, CDCl$_3$) δ ppm 7.55-7.65 (3H, m), 7.44-7.52 (2H, m), 7.35-7.45 (4H, m), 5.52 (1H, d, J=8.03 Hz), 3.48 (3H, s), 2.63 (2H, ddd, J=9.35, 3.95, 3.76 Hz), 2.14-2.25 (4H, m), 1.90-2.03 (3H, m), 1.69-1.82 (1H, m), 1.51 (9H, s).

Preparation 1K: (2S,3R)-6,6,6-Trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoic acid, and Preparation 1L: (2R,3R)-6,6,6-Trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoic acid

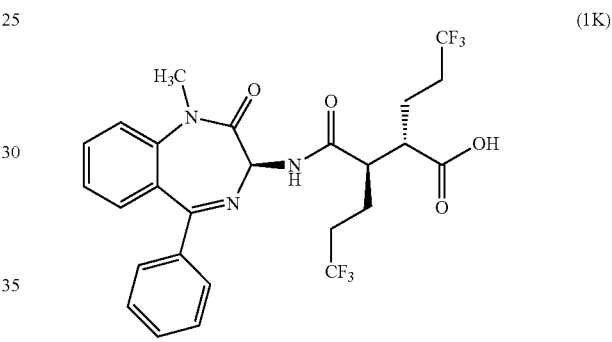

(1K)

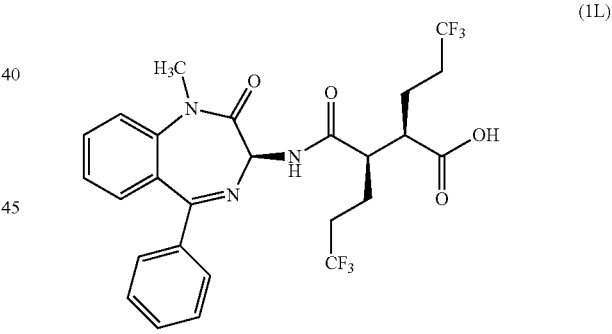

(1L)

To a cool (0° C.), stirred solution of the above mixture of Preparation 1I and Preparation 1J (2.95 g, 4.81 mmol) in DCM (20 mL) was added TFA (20 mL, 260 mmol). The reaction mixture was stirred for 1 hr, then allowed to warm to room temperature and stirred for 2.5 hr. The reaction was judged complete by LCMS. The reaction mixture was diluted with toluene (50 mL) and concentrated under reduced pressure. The residue mixture was redissolved in toluene (50 mL) and concentrated under reduced pressure then dried under high vacuum. The crude product was dissolved in DCM, SiO$_2$ (15 g) was added, concentrated, then was purified by flash chromatography (Teledyne ISCO CombiFlash Rf, 0% to 45% solvent A/B=DCM/EtOAc, REDISEP® SiO$_2$ 80 g). Concentration of appropriate fractions provided a mixture of Preparation 1K and Preparation 1L (2.00 g, 75%) as a cream solid: HPLC: RT=2.770 min (CHROMOLITH® SpeedROD 4.6× 50 mm (4 min grad) eluting with 10-90% aqueous MeOH over 4 minutes containing 0.1% TFA, 4 mL/min, monitoring at 254 nm); MS (ES): m/z=558 [M+H]+; 1H NMR (400 MHz, CDCl3) δ ppm 8.32 (1H, d, J=8.03 Hz), 7.65-7.71 (1H, m), 7.50-7.60 (3H, m), 7.41-7.49 (2H, m), 7.39 (1H, dd, J=7.91, 1.63 Hz), 7.23-7.35 (2H, m), 5.59 (1H, d, J=8.03 Hz), 3.51 (3H, s), 2.81 (1H, ddd, J=10.54, 6.90, 3.64 Hz), 2.67-2.76 (1H, m), 2.22-2.33 (3H, m), 1.99-2.12 (3H, m), 1.85-1.94 (1H, m), 1.79 (1H, ddd, J=13.87, 7.84, 3.64 Hz).

Example 1

To a stirred solution of an 8:1 mixture of Preparation 1K and Preparation 1L (3.46 g, 6.21 mmol) in DMF (25 mL) under nitrogen atmosphere was added ammonium chloride (3.32 g, 62.1 mmol), EDC (3.55 g, 18.52 mmol), HOBT (2.85 g, 18.61 mmol), and triethyl amine (16 mL, 115 mmol) and stirred overnight. The reaction was judged complete by LCMS. The reaction mixture was poured into water (200 mL) with vigorous swirling and then allowed to sit. The solid was collected by filtration, washed with water, allowed to dry to afford 3.6 g colorless solid. The solid was purified by preparative SFC chromatography (Lux-Cellulose-2 (3×25 cm), 8% methanol in CO2, 140 ml/min @220 nm and 35° C.; Sample: 3.6 g in 50 cc methanol, conc.=70 mg/ml, Stack injection: 0.5 cc/9.2 min). Fractions containing product were concentrated, dried overnight under vacuum. Obtained Example 1 (2.74 g, 79%) as a colorless solid (Crystal Form N-1): HPLC: RT=9.601 min (H2O/CH3CN with TFA, Sunfire C18 3.5 um, 4.6×150 mm, 4.6×150 mm, gradient=15 min, wavelength=220 and 254 nm). MS (ES): m/z=557 [M+H]+; 1H NMR (400 MHz, DMSO-d6) δ ppm 9.54 (1H, d, J=7.28 Hz), 7.71-7.80 (1H, m), 7.68 (2H, d, J=8.78 Hz), 7.50-7.62 (3H, m), 7.45 (2H, t, J=7.28 Hz), 7.29-7.40 (2H, m), 7.15 (1H, br. s.), 5.30 (1H, d, J=7.28 Hz), 3.39 (3H, s), 2.74-2.86 (1H, m), 2.02-2.32 (3H, m), 1.45-1.79 (4H, m); [α]$_D$=−107.0° (5.73 mg/mL, DMSO).

Crystal Form A-2 was prepared by adding approximately 1 mg of Example 1 to approximately 0.7 mL of acetone/acetonitrile/water solution (2:2:1). A mixture of colorless needles and thin blades crystals were obtained after one day of slow evaporation of the solution at room temperature. The thin blade crystals were separated to provide crystal Form A-2.

Crystal Form EA-3 was prepared by adding approximately 1 mg of Example 1 to approximately 0.7 mL of ethyl acetate/heptane solution (1:1). Colorless blade crystals were obtained after three days of slow evaporation of the solution at room temperature.

Crystal Form THF-2 was obtained by adding approximately 5 mg of Example 1 to approximately 0.7 mL of THF/water solution (4:1). Colorless blade-like crystals were obtained after one day of solvent evaporation at room temperature.

Alternate Procedure to Make Example 1

Preparation 1M: 3,3,3-Trifluoropropyl trifluoromethanesulfonate (1M)

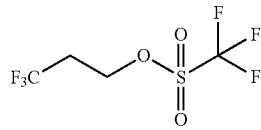

To a cold (−25° C.), stirred solution of 2,6-lutidine (18.38 mL, 158 mmol) in CH2Cl2 (120 mL) was added Tf2O (24.88 mL, 147 mmol) over 3 min, and stirred for 5 min. To the reaction mixture was added 3,3,3-trifluoropropan-1-ol (12 g, 105 mmol) over an interval of 3 min. After 2 hr, the reaction mixture was warmed to room temperature and stirred for 1 hr. The reaction mixture was concentrated to half volume, then purified by loading directly on silica gel column (330 g ISCO) and eluted with CH2Cl2. Obtained Preparation 1M (13.74 g, 53%) as a colorless oil. 1H NMR (400 MHz, CDCl3) δ ppm 4.71 (2H, t, J=6.15 Hz), 2.49-2.86 (2H, m).

Preparation 1N: (4S)-4-Benzyl-3-(5,5,5-trifluoropentanoyl)-1,3-oxazolidin-2-one (1N)

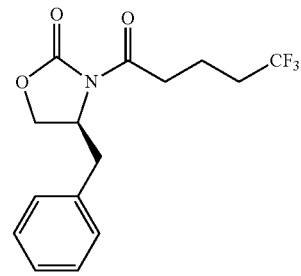

Preparation 1N was prepared from 5,5,5-trifluoropentanoic acid (3.35 g, 21.46 mmol) and (4S)-4-benzyl-1,3-oxazolidin-2-one (3.80 g, 21.46 mmol) by the general methods shown for Preparation 1B. Preparation 1N (5.67 g, 84%) was obtained as a colorless viscous oil: 1H NMR (400 MHz, CDCl3) δ ppm 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Preparation 1O: tert-Butyl (3R)-3-(4S)-4-benzyl-2-oxo-1,3-oxazolidin-3-yl)carbonyl)-6,6,6-trifluorohexanoate (1O)

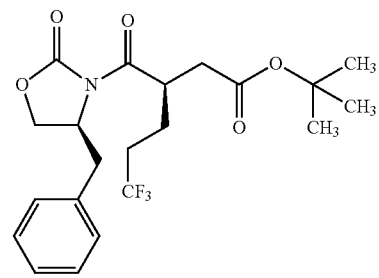

To a cold (−78° C.), stirred solution of Preparation 1N (3.03 g, 9.61 mmol) in THF (20 mL) was added NaHMDS (1.0M in THF) (10.6 mL, 10.60 mmol) under nitrogen atmosphere. After 2 hours, tert-butyl 2-bromoacetate (5.62 g, 28.8 mmol) was added neat via syringe at −78° C. and stirring was maintained at the same temperature. After 6 hours, the reaction mixture was warmed to room temperature. The reaction mixture was partitioned between saturated NH4Cl and EtOAc. The organic phase was separated, and the aqueous was extracted with EtOAc (3×). The combined organics were washed with brine, dried (Na2SO4), filtered and concentrated under reduced pressure. The residue was purified by flash chromatography (Teledyne ISCO CombiFlash Rf, 5% to 100% solvent A/B=hexanes/EtOAc, REDISEP® SiO2 120 g). Concentration of appropriate fractions provided Preparation 1O (2.79 g, 67.6%) as a colorless viscous oil: $^1$H NMR (400 MHz, CDCl$_3$) δ ppm 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Preparation 1P: (2R)-2-(2-tert-Butoxy-2-oxoethyl)-5,5,5-trifluoropentanoic acid

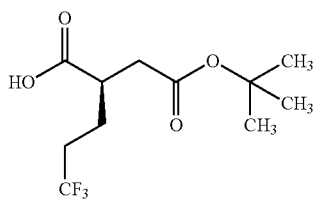

(1P)

Preparation 1P was prepared from Preparation 1O (2.79 g, 6.50 mmol) by the general methods shown for Preparation 1E. Preparation 1P (1.45 g, 83%) was obtained as a colorless oil: $^1$H NMR (400 MHz, CDCl$_3$) δ ppm 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Preparation 1E: (2R,3S)-3-(tert-Butoxycarbonyl)-6,6,6-trifluoro-2-(3,3,3-trifluoropropyl)hexanoic acid, and Preparation 1F: (2R,3R)-3-(tert-Butoxycarbonyl)-6,6,6-trifluoro-2-(3,3,3-trifluoropropyl)hexanoic acid

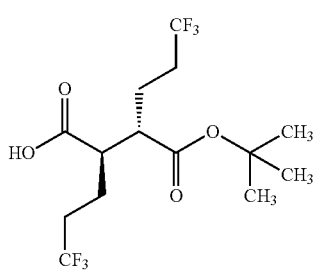

(1E)

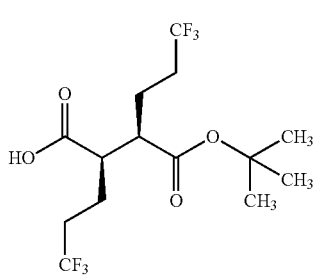

(1F)

To a cold (−78° C.), stirred solution of Preparation 1P (5.44 g, 20.13 mmol) in THF (60 mL) was slowly added LDA (24.60 mL, 44.3 mmol) over 7 min. After stirring for 2 hr, Preparation 1M (6.44 g, 26.2 mmol) was added to the reaction mixture over 3 min. After 45 min, the reaction mixture was warmed to −25° C. bath (ice/MeOH/dry ice) for 1 hr, and then warmed to 0° C. After 45 min, Preparation 1M (1 g) was added and the reaction mixture was stirred for 20 min. The reaction was quenched with water and 1N NaOH and was extracted with CH$_2$Cl$_2$. The organic layer was again extracted with 1N NaOH (2×) and the aqueous layers were combined. The aqueous layer was cooled in ice/water bath and then acidified with concentrated HCl to pH 2. Next, the aqueous layer was extracted with EtOAc. The combined organics were washed with brine, dried over anhydrous sodium sulphate, and concentrated under reduced pressure. The residue was dried under high vacuum to provide a 1:5 (1E:1F) mixture (as determined by $^1$H NMR) of Preparation 1E and Preparation 1F (5.925 g, 80%) as a pale yellow solid. $^1$H NMR (500 MHz, CDCl$_3$) δ ppm 2.81 (1H, ddd, J=10.17, 6.32, 3.85 Hz), 2.63-2.76 (1H, m), 2.02-2.33 (4H, m), 1.86-1.99 (2H, m), 1.68-1.85 (2H, m), 1.47 (9H, s).

Preparation 1E: (2R,3S)-3-(tert-Butoxycarbonyl)-6,6,6-trifluoro-2-(3,3,3-trifluoropropyl)hexanoic acid, and Preparation 1F: (2R,3R)-3-(tert-Butoxycarbonyl)-6,6,6-trifluoro-2-(3,3,3-trifluoropropyl)hexanoic acid

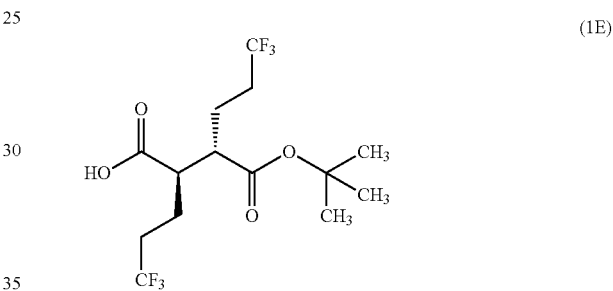

(1E)

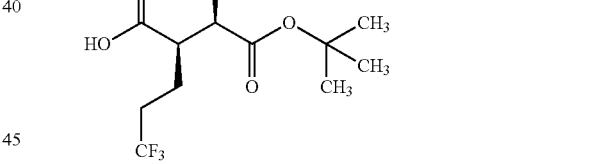

(1F)

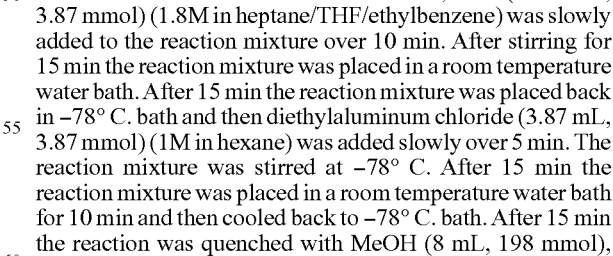

A mixture of Preparation 1E and Preparation 1F (64 mg, 1.758 mmol) was taken in THF (6 mL) to give a colorless solution which was cooled to −78° C. Then, LDA (2.149 mL, 3.87 mmol) (1.8M in heptane/THF/ethylbenzene) was slowly added to the reaction mixture over 10 min. After stirring for 15 min the reaction mixture was placed in a room temperature water bath. After 15 min the reaction mixture was placed back in −78° C. bath and then diethylaluminum chloride (3.87 mL, 3.87 mmol) (1M in hexane) was added slowly over 5 min. The reaction mixture was stirred at −78° C. After 15 min the reaction mixture was placed in a room temperature water bath for 10 min and then cooled back to −78° C. bath. After 15 min the reaction was quenched with MeOH (8 mL, 198 mmol), removed from the −78° C. bath and concentrated. To the reaction mixture was added ice and HCl (16 mL, 16.00 mmol), followed by extraction with EtOAc (2×). The organic layer was washed with potassium fluoride (920 mg, 15.84 mmol) (in 25 mL H$_2$O) and HCl (4.5 mL, 4.50 mmol). The organics were dried over anhydrous magnesium sulphate and concentrated under reduced pressure to provide a 9:1 (1E:1F) enriched mixture of Preparation 1E and Preparation 1F (540 mg, 1.583 mmol, 90% yield) as light yellow/orange solid. ¹H NMR (400 MHz, CDCl₃) δ ppm 2.64-2.76 (2H, m), 2.04-2.35 (4H, m), 1.88-2.00 (2H, m), 1.71-1.83 (2H, m), 1.48 (9H, s). It was converted to Example 1 by the sequence of reactions as outlined above.

Alternate Procedure to Make Preparation 1E

Preparation 1Q: (2R,3S)-1-Benzyl 4-tert-butyl 2,3-bis(3,3,3-trifluoropropyl)succinate

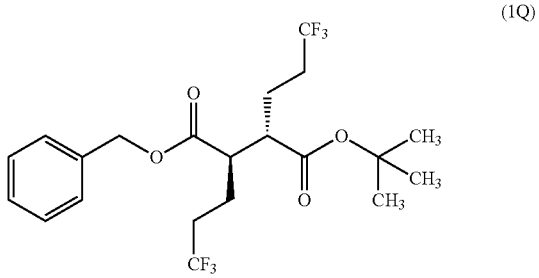 [SMILES: CC(C)(C)OC(=O)[C@@H](CCC(F)(F)F)[C@@H](CCC(F)(F)F)C(=O)OCc1ccccc1]

(1Q)

A clean and dry 5 L four neck round bottom flask equipped with mechanical stirring, thermometer socket and nitrogen bubbler at room temperature was charged with N,N-dimethyl formamide (2.07 L), a 1.2:1 mixture of Preparation 1E and Preparation 1F (207 g, 0.5651 moles), potassium carbonate (117.1 g, 0.8476 moles) followed by benzyl bromide (116 g, 0.6781 moles) over 15-20 min. The reaction mixture was stirred for 2-3 hr. After completion of the reaction, the reaction mixture was concentrated to dryness at 50-55° C. under vacuum. Ethyl acetate (3.1 L, 30 Vol.) was charged into the concentrated reaction mass and then washed with water (2.07 L), brine (0.6 L) then dried over anhydrous sodium sulfate (207 g), filtered and concentrated to dryness at 40-45° C. under vacuum. The residue was dissolved in dichloromethane (1.035 L, 5 vol.) and then absorbed onto silica gel (60-120) (607 g, 3.0 w/w), then was purified with column chromatography using petroleum ether and ethyl acetate as solvents. After pooling several batches, Preparation 1Q (235 g) was obtained. HPLC purity: 99.77%, Preparation 1E: (2R,3S)-3-(tert-Butoxycarbonyl)-6,6,6-trifluoro-2-(3,3,3-trifluoropropyl)hexanoic acid

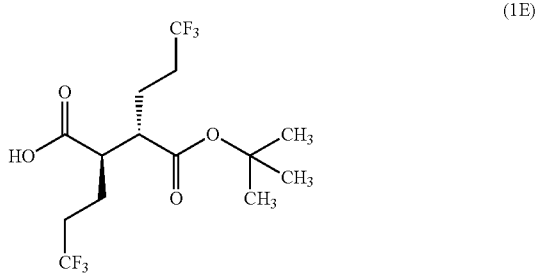 [SMILES: CC(C)(C)OC(=O)[C@@H](CCC(F)(F)F)[C@@H](CCC(F)(F)F)C(=O)O]

(1E)

A clean and dry 2 L autoclave was charged with methanol (540 mL) and was purged with nitrogen for 5-10 minutes. To the autoclave was added 10% palladium on carbon (12 g, 20%), purged with nitrogen once again for 5-10 min then was charged with Preparation 1Q (60 g, 0.1315 moles), the autoclave was flushed with methanol (60 mL) and stirred for 4-6 hr at 20-25° C. under 5 Kg hydrogen pressure. After completion of the reaction, the reaction mass was filtered through CELITE®, washed with methanol (180 mL), dried with anhydrous sodium sulfate (60 g), filtered and concentrated to dryness at 45-50° C. under vacuum. Obtained Preparation 1E (45.8 g, 95%) as a colorless solid: HPLC purity: 98.9%.

Alternate Procedure to Make Preparation 1E

Preparation 1E: (2R,3S)-3-(tert-Butoxycarbonyl)-6,6,6-trifluoro-2-(3,3,3-trifluoropropyl)hexanoic acid

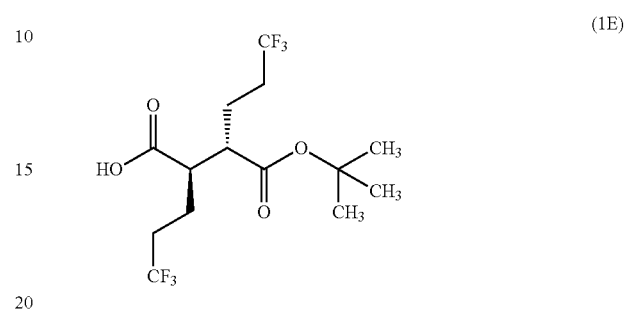

(1E)

Preparation 1E was prepared in a procedure identical as above from a mixture of Preparations 1E and 1F (200 g, 0.5460 moles) using LDA (1.8 M solution in THF, ethyl benzene and heptane) (698 mL, 2.3 equiv.) and diethyl aluminum chloride (1.0 M solution in hexane) (1256 mL, 2.3 equiv) in THF (2.0 L). After workup as explained above, the resulting residue was treated as follows: The crude material was added to a 2 L four neck round bottom flask, followed by the addition of MTBE (1.0 L) charged below 30° C. The resulting mixture was stirred for 5-10 minutes to obtain a clear solution. Hexanes (600 mL) was charged to the reaction mixture at a temperature below 30° C. The reaction mixture was stirred for 10 min. Next, tert-butylamine (43.8 g, 1.1 eq) was charged slowly over a period of 15 minutes below 30° C. This addition was observed to be exothermic. The reaction mixture was stirred for 2 hrs below 30° C. and filtered. The solid material was washed with 5:3 MTBE:hexane (200 mL), the filtrate was concentrated and transferred to an amber color bottle. The filtered solid was dissolved in dichloromethane (2.0 L), washed with 1N HCl (2.0), the organic layer was washed with brine (1.0 L×2), then was concentrated under reduced pressure below 45° C. This material was found to be 91.12% pure. The material was repurified by the above t-butylamine crystallization purification procedure. Obtained Preparation 1E (78 g, 39%): HPLC purity: 99.54%.

Alternate Procedure to Make Example 1

Preparation 1I: tert-Butyl (2S,3R)-6,6,6-trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoate

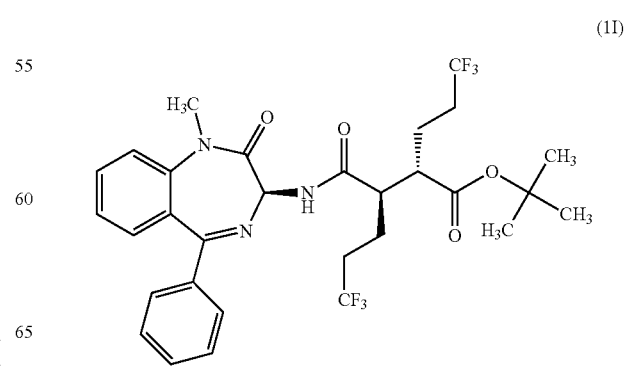

(1I)

A clean and dry 2 L four neck round bottom flask equipped with mechanical stirring, thermometer socket and nitrogen bubbler was charged with N,N-dimethylformamide (457 mL), Preparation 1E (45.7 g, 0.1248 moles) and Preparation 1G.CSA (62.08 g, 0.1248 moles) under nitrogen atmosphere at 20-25° C. The reaction mixture was stirred for 15-20 minutes to make clear solution at 20-25° C. To the reaction mixture was added TBTU (48.16 g, 0.1498 moles) at 20-25° C. followed by triethylamine (50.51 g, 0.4992 moles) over 15-20 minutes at 20-25° C. The reaction mixture was stirred for 60-120 minutes at 20-25° C. under nitrogen atmosphere. After completion of the reaction, the reaction was quenched into water (1.37 L, 30 Vol.) at 20-25° C. under stirring. The reaction mixture was stirred for 30 minutes at 20-25° C. The reaction mixture was filtered and washed with water (228 mL). The resulting solid material was dissolved in ethyl acetate (457 mL), washed with water (2×137 mL), brine (137 mL), and then dried with anhydrous sodium sulfate (45.7 g). Activated charcoal (9.14 g, 20%) was charged into the reaction mixture and stirred for 30 minutes. The mixture was filtered through CELITE® bed and 1 micron filter cloth, washed charcoal bed with ethyl acetate (137 mL), concentrated to 1.0 Vol. stage and then petroleum ether (457 mL, 10 Vol.) was charged and stirred for 30 minutes at 20-25° C. The solid was collected by filtration, washed with petroleum ether (137 mL) and then dried under vacuum at 40-45° C. for 8 hr until loss on drying was less than 3.0%. Obtained Preparation 1I (65.2 g, 85%): HPLC purity: 98.26%.

Preparation 1K: (2S,3R)-6,6,6-Trifluoro-3-(((3S)-1-methyl-2-oxo-5-phenyl-2,3-dihydro-1H-1,4-benzodiazepin-3-yl)carbamoyl)-2-(3,3,3-trifluoropropyl)hexanoic acid

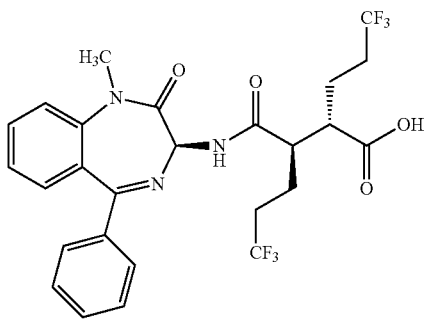

(1K)

A clean and dry 3 L four neck round bottom flask equipped with mechanical stirring, thermometer socket and nitrogen bubbler was charged with dichloromethane (980 mL) under nitrogen atmosphere followed by Preparation 1I (140 g, 0.2282 moles) at 20-25° C. The reaction mixture was cooled to 0-5° C. and trifluoroacetic acid (980 mL) was charged slowly for 30-40 minutes. The resulting mixture was stirred for 2 hr at 0-5° C. under nitrogen atmosphere. The reaction temperature was raised to 20 to 25° C., and the reaction mixture was stirred for 1-2 hr at 20 to 25° C. After completion of the reaction, the reaction mixture was concentrated to dryness at 50 to 55° C. under vacuum. Toluene (3×700 mL,) was charged into the concentrated reaction mass, and then distilled off at 50 to 55° C. under vacuum. After complete concentration from toluene, ethyl acetate (280 mL) was charged into the reaction mass at 20 to 25° C., stirred for 60 minutes, then the solid was collected by filtration, washed with ethyl acetate (140 mL), dried under vacuum at 50 to 55° C. for 12 hr until loss on drying was less than 2.0%. Obtained Preparation 1K (106 g, 84%): HPLC purity: 98.43%.

Example 1

A reaction vessel was charged with Preparation 1K (30 g, 53.81 mmol), HOBt (8.7 g, 64.38 mmol), and THF (150 mL) at room temperature. To the homogeneous solution was added EDCI (12.4 g, 64.68 mmol), stirred for 15 min, then cooled to 8° C. To the reaction mixture was added ammonia (2M in IPA) (81 mL, 162 mmol) over 5 min so as to maintain a temperature below 10° C. The resulting heavy slurry was stirred for 10 min, warmed to room temperature over 30 min, then stirred for 4 hr. At the completion of the reaction, water (230 mL) was slowly added over 15 min to maintain a temperature below 20° C., and then stirred for 2 hr. The solid was collected by filtration, washed with water (3×60 mL), then dried under vacuum 48 hr at 55° C. The above crude product was charged into a 1 L 3-necked round flask. IPA (200 mL) was added, then heated to 80° C. resulting in a homogeneous solution. Water (170 mL) was slowly added (15 min) to maintain an internal temperature>75° C. The resulting slurry was stirred and cooled to room temperature for 2 hr. The solid was collected by filtration, washed with water (2×50 mL), then dried under vacuum (55° C. for 24 h, and 30° C. for 48 h). Obtained Example 1 (23.4 g, 78% yield): HPLC purity: 99.43%.

Example 2

(2R,3S)—N-((3S)-2-Oxo-5-phenyl-2,3-dihydro-1H-1,4-benzodiazepin-3-yl)-2,3-bis(3,3,3-trifluoropropyl)succinamide

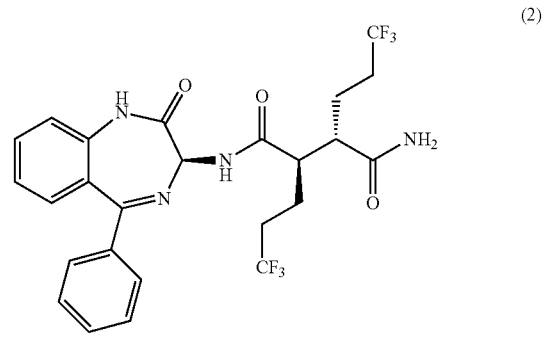 [SMILES: NC(=O)[C@@H](CCC(F)(F)F)[C@@H](CCC(F)(F)F)C(=O)N[C@H]1N=C(c2ccccc2)c2ccccc2NC1=O]

(2)

Preparation 2A: (3S)-3-Amino-5-phenyl-1,3-dihydro-2H-1,4-benzodiazepin-2-one, and Preparation 2B: (3R)-3-Amino-5-phenyl-1,3-dihydro-2H-1,4-benzodiazepin-2-one

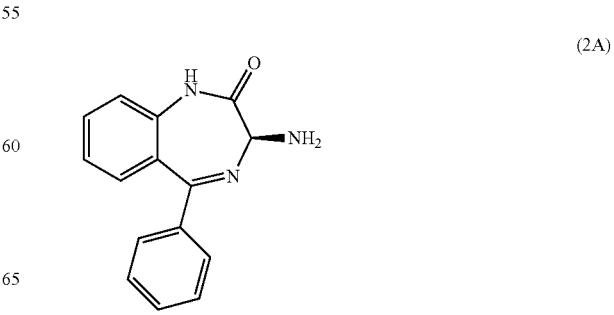

(2A)

-continued

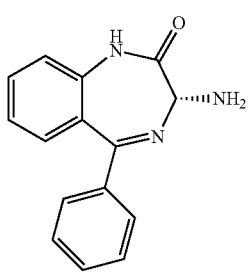
(2B)

Racemic 3-amino-5-phenyl-1,3-dihydro-2H-1,4-benzodiazepin-2-one (*J. Med. Chem.*, 49:2311-2319 (2006), compound#5) was prepared according to the literature procedure. The enantiomers were separated on Berger SFC MGIII Column: Lux 25×3 cm, 5 cm; Mobile phase: 30% MeOH+0.1% DEA in $CO_2$; Flow rate: 150 mL/min; Temperature: 40° C.; Detector wavelength: 250 nM. Obtained the S-enantiomer Preparation 2A as a white solid: $^1$H NMR (400 MHz, DMSO-$d_6$) δ ppm 10.67 (1H, br. s.), 7.58 (1H, td, J=7.65, 1.76 Hz), 7.37-7.53 (5H, m), 7.23-7.30 (2H, m), 7.14-7.22 (1H, m), 4.23 (1H, s), 2.60 (2H, br. s.); HPLC: RT=3.0625 min (30% MeOH+0.1% DEA in $CO_2$ on OD-H Column, 3 mL/min, 35° C., 96 bar, 230 nm, 10 µl inj); $[α]_D$=−208.3° (5.05 mg/mL, MeOH). Also obtained the R-enantiomer Preparation 2B as an off white solid: HPLC: RT=3.970 min; $[α]_D$=182.1° (2.01 mg/mL, MeOH).

Preparation 2C: tert-Butyl (2S,3R)-6,6,6-trifluoro-3-(((3S)-2-oxo-5-phenyl-2,3-dihydro-1H-1,4-benzodiazepin-3-yl)carbamoyl)-2-(3,3,3-trifluoropropyl)hexanoate, and Preparation 2D: tert-Butyl (2R,3R)-6,6,6-trifluoro-3-(((3S)-2-oxo-5-phenyl-2,3-dihydro-1H-1,4-benzodiazepin-3-yl)carbamoyl)-2-(3,3,3-trifluoropropyl)hexanoate

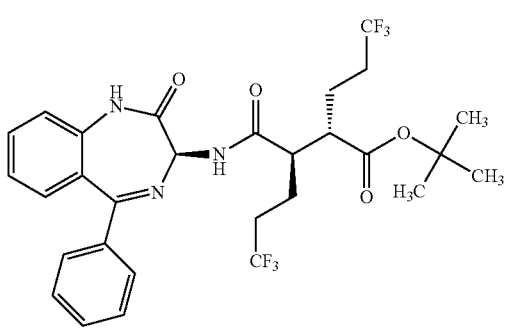
(2C)

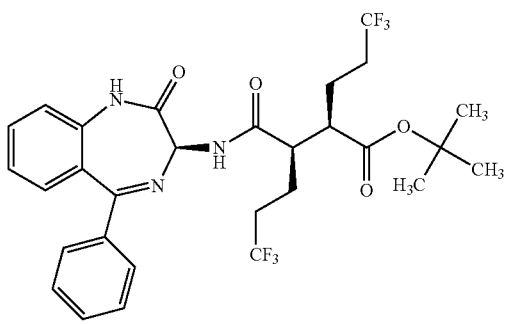
(2D)

Preparation 2C was prepared from Preparation 2A (564 mg, 2.244 mmol) and a mixture of Preparation 1E and Preparation 1F (822 mg, 2.244 mmol) according to the general procedure shown for Preparation 1I. Obtained Preparation 2C and Preparation 2D (1.31 g, 97%): HPLC: RT=3.443 min (CHROMOLITH® ODS 4.6×50 mm (4 min grad) eluting with 10-90% aqueous MeOH over 4 minutes containing 0. % TFA, 4 mL/min, monitoring at 220 nm); MS (ES): m/z=600.3 $[M+H]^+$.

Preparation 2E: (2S,3R)-6,6,6-Trifluoro-3-(((3S)-2-oxo-5-phenyl-2,3-dihydro-1H-1,4-benzodiazepin-3-yl)carbamoyl)-2-(3,3,3-trifluoropropyl)hexanoic acid, and Preparation 2F: (2R,3R)-6,6,6-Trifluoro-3-(((3S)-2-oxo-5-phenyl-2,3-dihydro-1H-1,4-benzodiazepin-3-yl)carbamoyl)-2-(3,3,3-trifluoropropyl)hexanoic acid

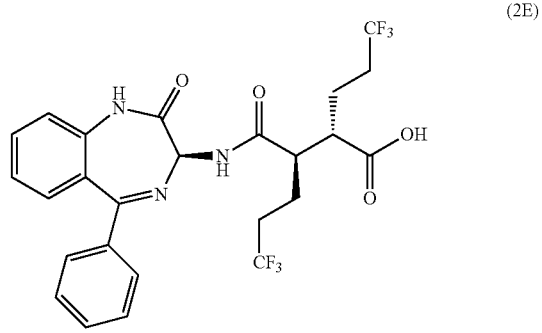
(2E)

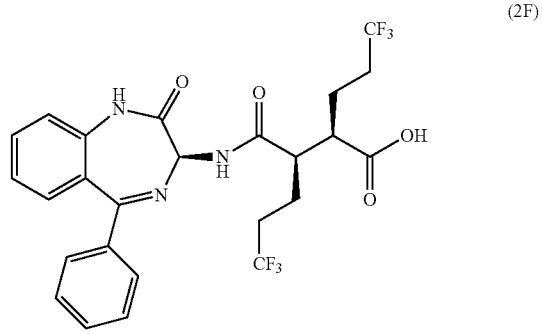
(2F)

A mixture of Preparation 2E and Preparation 2F was prepared from a mixture of Preparation 2C and Preparation 2D (1.31 g, 2.185 mmol) by the general methods shown for Preparation 1K. Obtained a mixture of Preparation 2E and Preparation 2F (1.18 g, 99%): HPLC: RT=2.885 min (CHROMOLITH® ODS 4.6×50 mm (4 min grad) eluting with 10-90% aqueous MeOH over 4 minutes containing 0. % TFA, 4 mL/min, monitoring at 220 nm). MS (ES): m/z=544.2 $[M+H]^+$.

Example 2

Example 2 was prepared from a mixture of Preparation 2E and Preparation 2F (354 mg, 0.651 mmol) by the general methods shown for Example 1. After separation of the diastereoisomers, Example 2 was obtained (188 mg, 52%) as a white solid: HPLC: RT=9.063 min ($H_2O$/$CH_3CN$ with TFA, Sunfire C18 3.5 um, 4.6×150 mm, 4.6×150 mm, gradient=15 min, wavelength=220 and 254 nm); MS (ES): m/z=543 $[M+H]^+$; $^1$H NMR (400 MHz, DMSO-$d_6$) δ ppm 10.87 (1H, br. s.), 9.50-9.55 (1H, m), 7.62-7.69 (2H, m), 7.40-7.57 (5H, m), 7.29-7.36 (2H, m), 7.22-7.28 (1H, m), 7.16 (1H, br. s.), 5.25 (1H, d), 3.30-3.32 (1H, m), 2.75-2.86 (1H, m), 2.44-2.48

(1H, m), 2.06-2.34 (3H, m), 1.51-1.77 (4H, m); [α]$_D$=−114.4° (8.04 mg/mL, DMSO).

Crystal Form M2-1 was prepared by adding approximately 1 mg of Example 2 to approximately 0.7 mL of MeOH/fluorobenzene solution (3:1). Colorless plate-like crystals were obtained after 2 days of solvent evaporation at room temperature.

Example 3

(2R,3S)—N-((3S)-1-Methyl-2-oxo-5-phenyl-2,3-dihydro-1H-1,4-benzodiazepin-3-yl)-2-(2,2,2-trifluoroethyl)-3-(3,3,3-trifluoropropyl)succinamide

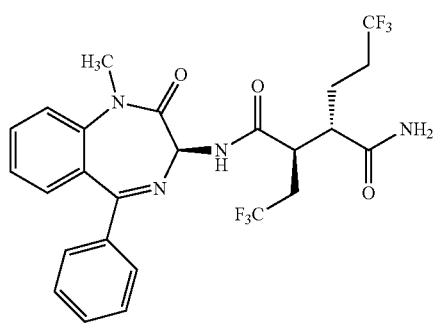

(3)

Preparation 3A: (4S)-4-(Propan-2-yl)-3-(4,4,4-trifluorobutanoyl)-1,3-oxazolidin-2-one

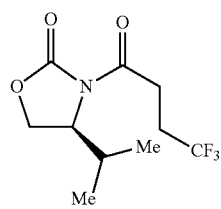

(3A)

Preparation 3A was prepared from (4S)-4-(propan-2-yl)-1,3-oxazolidin-2-one (4.66 g, 36.1 mmol) and 4,4,4-trifluorobutanoic acid (5.02 g, 35.3 mmol) by the general methods shown for Preparation 1B. Preparation 3A was obtained as a colorless oil (3.64 g, 40%). $^1$H NMR (400 MHz, CDCl$_3$) δ ppm 4.44 (1H, ddd, J=8.41, 3.51, 3.39 Hz), 4.31 (1H, t, J=8.66 Hz), 4.25 (1H, dd, J=9.03, 3.26 Hz), 3.13-3.32 (2H, m), 2.47-2.59 (2H, m), 2.38 (1H, dddd, J=13.96, 7.01, 3.89 Hz), 0.93 (3H, d, J=7.28 Hz), 0.88 (3H, d, J=6.78 Hz).

Preparation 3B: tert-Butyl (3R)-5,5,5-trifluoro-3-(((4S)-2-oxo-4-(propan-2-yl)-1,3-oxazolidin-3-yl)carbonyl)-2-(3,3,3-trifluoropropyl)pentanoate

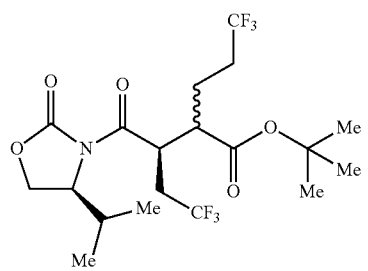

(3B)

Preparation 3B was prepared from Preparation 3A (1.04 g, 4.12 mmol) and tert-butyl 5,5,5-trifluoropentanoate (Preparation 1A) (1.55 g, 7.28 mmol) by the general methods shown for Preparation 1C. Preparation 3B (528.3 mg, 28%) was obtained as a pale yellow viscous oil: $^1$H NMR (400 MHz, CDCl$_3$) δ ppm 4.57 (1H, ddd, J=10.54, 5.02, 1.76 Hz), 4.41-4.50 (2H, m), 4.20-4.32 (4H, m), 2.77-2.88 (3H, m), 2.70 (1H, dt, J=9.79, 4.89 Hz), 2.38 (1H, dddd, J=10.38, 6.87, 3.64, 3.45 Hz), 2.23-2.34 (4H, m), 2.06-2.18 (2H, m), 1.93-2.05 (2H, m), 1.69-1.81 (4H, m), 1.46 (9H, s), 1.43 (9H, s), 0.85-0.97 (12H, m).

Preparation 3C: (2R)-3-(tert-Butoxycarbonyl)-6,6,6-trifluoro-2-(2,2,2-trifluoroethyl)hexanoic acid

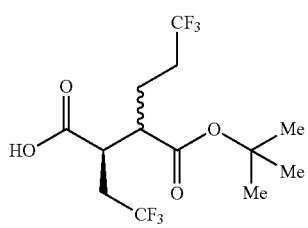

(3C)

Preparation 3C was prepared from Preparation 3B (528.3 mg, 1.140 mmol) by the general methods shown for Preparation 1D. Preparation 3C (306.7 mg, 76%) was obtained as a colorless waxy solid (306.7 mg, 76%). $^1$H NMR (400 MHz, CDCl$_3$) δ ppm 3.08 (1H, ddd, J=8.72, 4.20, 3.89 Hz), 3.00 (1H, ddd, J=9.66, 7.03, 2.89 Hz), 2.70-2.82 (4H, m), 2.36 (1H, ddd, J=15.25, 10.73, 3.64 Hz), 2.18-2.30 (2H, m), 2.12 (2H, dd, J=10.16, 5.65 Hz), 1.90-2.02 (2H, m), 1.70-1.81 (3H, m), 1.45-1.51 (18H, m).

Preparation 3D: (2R,3S)-3-(tert-Butoxycarbonyl)-6,6,6-trifluoro-2-(2,2,2-trifluoroethyl)hexanoic acid

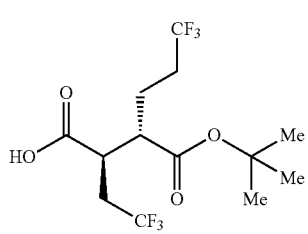

(3D)

Preparation 3D was prepared from Preparation 3C (306.7 mg, 0.871 mmol) by the general methods shown to enrich the mixture of Preparation 1E and Preparation 1F. Preparation 3D (297.0 mg, 97%) was obtained as a yellow waxy solid (297.0 mg, 97%). $^1$H NMR (400 MHz, CDCl$_3$) δ ppm 2.99 (1H, ddd, J=9.47, 6.96, 2.89 Hz), 2.69-2.82 (2H, m), 2.18-2.31 (2H, m), 2.06-2.18 (1H, m), 1.91-2.03 (1H, m), 1.68-1.80 (1H, m), 1.46-1.51 (9H, m).

Preparation 3E: tert-Butyl (2S,3R)-5,5,5-trifluoro-3-(((3S)-1-methyl-2-oxo-5-phenyl-2,3-dihydro-1H-1,4-benzodiazepin-3-yl)carbamoyl)-2-(3,3,3-trifluoropropyl)pentanoate

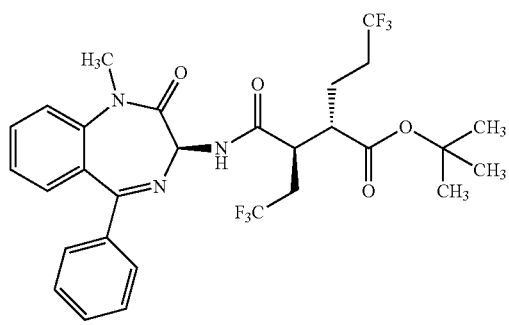

(3E)

Preparation 3E was prepared from Preparation 3D (297.0 mg, 0.843 mmol) and Preparation 1G (212.0 mg, 0.799 mmol) by the general methods shown for Preparation 1I. Preparation 3E (471.7 mg, 98%) was obtained as a tan solid (471.7 mg, 98%). MS (ES): m/z=600 [M+H]$^+$; $^1$H NMR (400 MHz, CDCl$_3$) δ ppm 7.75 (1H, d, J=7.78 Hz), 7.54-7.64 (3H, m), 7.43-7.51 (1H, m), 7.34-7.43 (4H, m), 7.22-7.31 (1H, m), 5.50 (1H, d, J=7.53 Hz), 3.48 (3H, s), 2.87-2.96 (1H, m), 2.73-2.83 (1H, m), 2.60 (1H, td, J=10.10, 3.89 Hz), 2.13-2.25 (3H, m), 1.86-2.05 (2H, m), 1.52 (9H, s).

Preparation 3F: (2S,3R)-5,5,5-Trifluoro-3-(((3S)-1-methyl-2-oxo-5-phenyl-2,3-dihydro-1H-1,4-benzodiazepin-3-yl)carbamoyl)-2-(3,3,3-trifluoropropyl)pentanoic acid

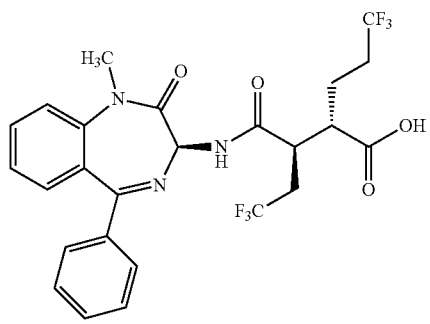

(3F)

Preparation 3F was prepared from Preparation 3E (466.1 mg, 0.777 mmol) by the general methods shown for Preparation 1H. Preparation 3F (451 mg, >99%) was obtained as a tan solid. MS (ES): m/z=544 [M+H]$^+$; $^1$H NMR (400 MHz, CDCl$_3$) δ ppm 8.29 (1H, d, J=7.53 Hz), 7.64 (1H, td, J=7.84, 1.63 Hz), 7.53-7.60 (2H, m), 7.49 (1H, t, J=7.40 Hz), 7.33-7.46 (4H, m), 7.22-7.33 (2H, m), 5.53 (1H, d, J=7.53 Hz), 3.49 (3H, s), 3.04-3.21 (2H, m), 2.69-2.81 (2H, m), 2.23-2.33 (2H, m), 2.07-2.19 (2H, m).

Example 3

Example 3 was prepared from Preparation 3F (446 mg, 0.821 mmol) by the general methods shown for Example 1. After separation of the diastereoisomers, Example 3 was obtained: HPLC: RT=3.17 min (H$_2$O/CH$_3$CN with TFA, Sunfire C18 3.5 um, 4.6×150 mm, 4.6×150 mm, gradient=15 min, wavelength=220 and 254 nm). MS (ES): m/z=543.3 [M+H]$^+$; $^1$H NMR (400 MHz, DMSO-d$_6$) δ ppm 9.72 (1H, d, J=8.53 Hz), 7.71-7.77 (1H, m), 7.66-7.71 (1H, m), 7.64 (1H, d, J=1.25 Hz), 7.48-7.57 (3H, m), 7.39-7.47 (2H, m), 7.30-7.39 (2H, m), 7.23 (1H, s), 5.36 (1H, d, J=8.53 Hz), 3.39 (3H, s), 3.12-3.23 (1H, m), 2.53-2.61 (1H, m), 2.43 (1H, td, J=10.10, 3.89 Hz), 2.16-2.28 (1H, m), 2.02-2.16 (1H, m), 1.82-1.96 (1H, m), 1.68-1.82 (1H, m).

Example 4

(2R,3S)—N-((3S)-1-Methyl-2-oxo-5-phenyl-2,3-dihydro-1H-1,4-benzodiazepin-3-yl)-3-(2,2,2-trifluoroethyl)-2-(3,3,3-trifluoropropyl)succinamide

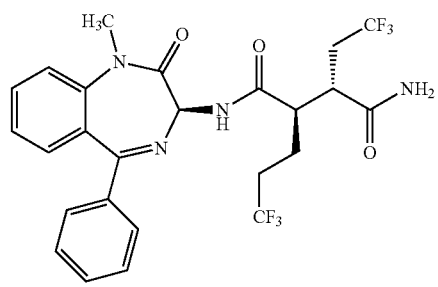

(4)

Preparation 4A: tert-Butyl 4,4,4-trifluorobutanoate

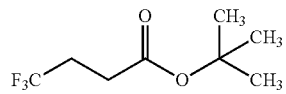

(4A)

Preparation 4A was prepared from 4,4,4-trifluorobutanoic acid (4.99 g, 35.1 mmol) using the general procedure shown for Preparation 1A. Preparation 4A (5.58 g, 80%) was obtained as a colorless oil. $^1$H NMR (400 MHz, CDCl$_3$) δ ppm 2.47-2.52 (2H, m), 2.37-2.45 (2H, m), 1.46 (9H, s).

Preparation 4B: tert-Butyl (3R)-6,6,6-trifluoro-3-(((4S)-2-oxo-4-(propan-2-yl)-1,3-oxazolidin-3-yl)carbonyl)-2-(2,2,2-trifluoroethyl)hexanoate

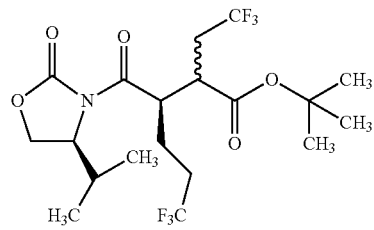

(4B)

Preparation 4B was prepared from Preparation 4A (1058.3 mg, 5.34 mmol) and Preparation 1B (809.2 mg, 3.03 mmol) according to the general procedure shown for Preparation 1C. Preparation 4B (690.1 mg, 49%) was obtained as a pale yellow viscous oil. $^1$H NMR (400 MHz, CDCl$_3$) δ ppm 4.45-4.52 (1H, m), 4.23-4.40 (1H, m), 4.05-4.12 (1H, m), 3.70 (1H, t, J=6.7 Hz), 3.05 (1H, ddd, J=9.9, 5.0, 2.3 Hz), 2.99 (1H, ddd, J=11.2, 5.8, 1.8 Hz), 2.58-2.91 (2H, m), 2.38-2.49 (1H, m), 2.27-2.36 (1H, m), 2.07-2.26 (1H, m), 1.96-2.04 (1H, m), 1.85-1.94 (1H, m), 1.72-1.82 (1H, m), 1.46 (3H, s), 0.88-0.98 (3H, m); HPLC: RT=3.36 min (MeOH/H$_2$O/0.1% TFA, CHROMOLITH® SpeedROD 4.6×50 mm, 4 min gradient, wavelength=220 nm).

Preparation 4C: (2R)-3-(tert-Butoxycarbonyl)-5,5,5-trifluoro-2-(3,3,3-trifluoropropyl)pentanoic acid

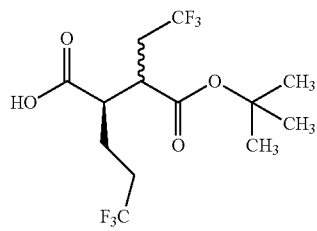

(4C)

Preparation 4C was prepared from Preparation 4B (690.1 mg, 1.489 mmol) according to the general procedure shown for Preparation 1E. Preparation 4C (335.9 mg, 64%) was obtained as a colorless oil. $^1$H NMR (400 MHz, CDCl$_3$) δ ppm 2.91-3.03 (1H, m), 2.63-2.88 (2H, m), 2.50 (1H, t, J=7.3 Hz), 2.07-2.43 (4H, m), 1.89-2.05 (2H, m), 1.73-1.88 (1H, m), 1.47 (5H, s), 1.47 (4H, s).

Preparation 4D: (2R,3S)-3-(tert-Butoxycarbonyl)-5,5,5-trifluoro-2-(3,3,3-trifluoropropyl)pentanoic acid

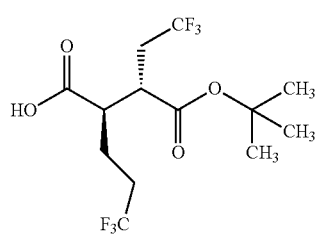

(4D)

Preparation 4D was prepared from Preparation 4C (335.9 mg, 0.954 mmol) according to the general procedure shown to enrich the mixture of Preparation 1E and Preparation 1F. Preparation 4D (277.8 mg, 83%) was obtained as a brown oil. $^1$H NMR (400 MHz, CDCl$_3$) δ ppm 2.90-3.03 (1H, m), 2.64-2.88 (2H, m), 2.50 (1H, t, J=7.3 Hz), 2.06-2.43 (3H, m), 1.89-2.03 (1H, m), 1.73-1.88 (1H, m), 1.47 (9H, s).

Preparation 4E: tert-Butyl (2S,3R)-6,6,6-trifluoro-3-(((3S)-1-methyl-2-oxo-5-phenyl-2,3-dihydro-1H-1,4-benzodiazepin-3-yl)carbamoyl)-2-(2,2,2-trifluoroethyl)hexanoate

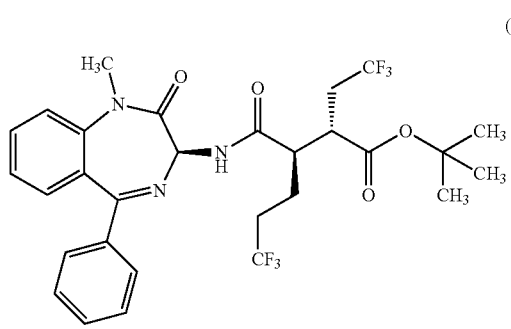

(4E)

Preparation 4E was prepared from Preparation 4D (277.8 mg, 0.789 mmol) and Preparation 1G (210.2 mg, 0.792 mmol) according to the general procedure shown for Preparation 1I. Preparation 4E was obtained as a cream solid (420.2 mg, 89%). $^1$H NMR (400 MHz, CDCl$_3$) δ ppm 7.55-7.65 (3H, m), 7.48 (1H, d, J=7.5 Hz), 7.36-7.45 (4H, m), 5.51 (1H, d, J=7.8 Hz), 3.49 (3H, s), 2.87-2.92 (1H, m), 2.63 (1H, s), 2.47-2.58 (1H, m), 2.16-2.36 (2H, m), 1.93-2.06 (1H, m), 1.80 (1H, s), 1.51 (9H, s); LCMS: RT=4.02 min (MeOH/H$_2$O/0.1% TFA, CHROMOLITH® RP-18e 2.0×50 mm, 4 min gradient, wavelength=254 nm); MS (ES):m/z=600 [M+H$^+$].

Preparation 4F: (2S,3R)-6,6,6-Trifluoro-3-(((3S)-1-methyl-2-oxo-5-phenyl-2,3-dihydro-1H-1,4-benzodiazepin-3-yl)carbamoyl)-2-(2,2,2-trifluoroethyl)hexanoic acid

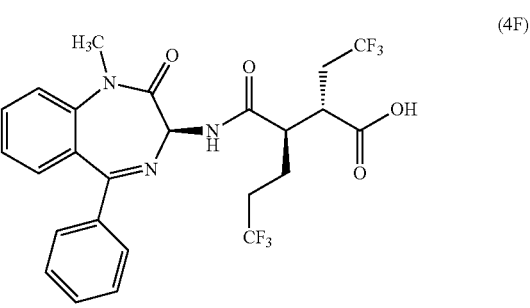 [SMILES: CN1C(=O)[C@@H](NC(=O)[C@H](CCC(F)(F)F)[C@H](CC(F)(F)F)C(=O)O)N=C(c2ccccc2)c2ccccc21]

(4F)

Preparation 4F was prepared from Preparation 4E (417.2 mg, 0.696 mmol) according to the general procedure shown for Preparation 1K. Preparation 4F was obtained as a TFA solvate as an amber solid (476.0 mg, 96%). $^1$H NMR (400 MHz, CDCl$_3$) δ ppm 8.25 (1H, d, J=8.0 Hz), 7.73-7.82 (1H, m), 7.56-7.67 (2H, m), 7.34-7.54 (3H, m), 5.67 (1H, d, J=8.3 Hz), 3.49-3.60 (2H, m), 3.05-3.13 (1H, m), 2.81-2.97 (1H, m), 2.39-2.60 (1H, m), 2.18-2.33 (1H, m), 1.95-2.13 (1H, m); LCMS: RT=3.43 min (MeOH/H$_2$O/0.1% TFA, CHROMOLITH® RP-18e 2.0×50 mm, 4 min gradient, wavelength=254 nm); MS (ES):m/z=544 [M+H$^+$].

Example 4

Example 4 was prepared from Preparation 4F (476.3 mg, 0.667 mmol) according to the general procedure shown for Example 1. After separation of the diastereoisomers, Example 4 was obtained as a cream solid (120.3 mg, 32%). HPLC: RT=9.446 min (H$_2$O/CH$_3$CN with TFA, Sunfire C18 3.5 μm, 4.6×150 mm, 4.6×150 mm, gradient=15 min, wavelength=220 and 254 nm); MS (ES):m/z=543 [M+H$^+$]; $^1$H NMR (400 MHz, DMSO-d$_6$) δ ppm 9.56 (1H, d, J=7.03 Hz), 7.82 (1H, s), 7.70-7.78 (1H, m), 7.64-7.70 (1H, m), 7.50-7.63 (3H, m), 7.47 (2H, d, J=7.78 Hz), 7.30-7.42 (2H, m), 7.21 (1H, s), 5.30 (1H, d, J=7.03 Hz), 3.39 (3H, s), 2.67-2.80 (2H, m), 2.51-2.62 (2H, m), 2.19-2.29 (1H, m), 2.07-2.21 (1H, m), 1.60-1.72 (2H, m).

Example 5

(2R,3S)—N-((3S)-1-($^2$H$_3$)Methyl-2-oxo-5-phenyl-2,3-dihydro-1H-1,4-benzodiazepin-3-yl)-2,3-bis(3,3,3-trifluoropropyl)succinamide

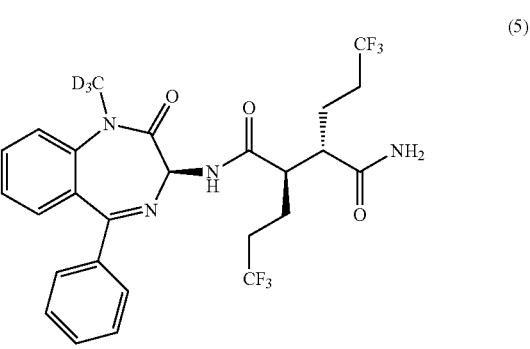 [SMILES: [2H]C([2H])([2H])N1C(=O)[C@@H](NC(=O)[C@H](CCC(F)(F)F)[C@H](CCC(F)(F)F)C(N)=O)N=C(c2ccccc2)c2ccccc21]

(5)

In a 5 mL screw top vial was added Example 2 (50 mg, 0.092 mmol), cesium carbonate (60.1 mg, 0.184 mmol), and iodomethane-$d_3$ (6.88 μL, 0.111 mmol) in DMF (2 mL) to give a suspension. The mixture was stirred at room temperature under nitrogen overnight. LCMS showed the reaction was complete. The reaction mixture was dissolved in 2 ml of 1:1 DMF/AcOH and purified by Preparative HPLC on Luna ODS 5 um 21.2×100 mm which was eluted with a 7 min gradient from 10% to 100% ACN/water 0.1% TFA to 100%. The appropriate fractions was concentrated to afford Example 5 (35 mg, 65%): HPLC: RT=3.04 min (CHROMOLITH® S5 ODS column 4 6×50 mm, 10-90% aqueous methanol over 4 minutes containing 0.1% TFA, 4 mL/min, monitoring at 220 nm); MS (ES): m/z=599 [M+H]$^+$; $^1$H NMR (400 MHz, DMSO-$d_6$) δ ppm 9.55 (1H, d, J=7.5 Hz), 7.71-7.80 (1H, m), 7.67 (2H, d, J=8.3 Hz), 7.51-7.60 (3H, m), 7.42-7.49 (2H, m), 7.30-7.39 (2H, m), 7.15 (1H, s), 5.30 (1H, d, J=7.3 Hz), 2.75-2.87 (1H, m), 2.40-2.48 (1H, m), 2.04-2.31 (4H, m), 1.46-1.76 (4H, m).

Examples 6 to 11

The compounds listed below were prepared according to the general synthetic procedure described in Example 1, using the appropriate benzodiazepinone obtained by methods known to one skilled in the art, for example, Carter, M. C. et al., *J. Med. Chem.*, 49:2311-2319 (2006).

TABLE 6

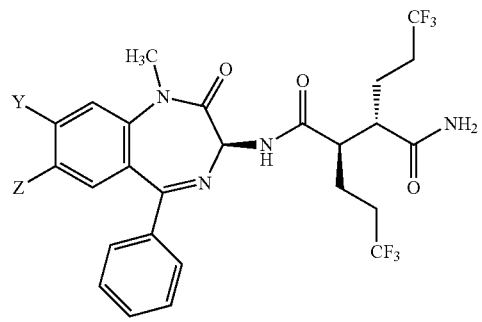

| Ex. No. | Y | Z | Compound Name | [M + H]$^+$ | HPLC Ret Time (min) |
|---|---|---|---|---|---|
| 6 | H | Cl | (2R,3S)-N-((3S)-7-chloro-1-methyl-2-oxo-5-phenyl-2,3-dihydro-1H-1,4-benzodiazepin-3-yl)-2,3-bis(3,3,3-trifluoropropyl) succinamide | 591 | 17.21 [a] |
| 7 | OCH$_3$ | H | (2R,3S)-N-((3S)-8-methoxy-1-methyl-2-oxo-5-phenyl-2,3-dihydro-1H-1,4-benzodiazepin-3-yl)-2,3-bis(3,3,3-trifluoropropyl)succinamide | [M − H] = 585 | 15.86 [a] |
| 8 | F | H | (2R,3S)-N-((3S)-8-fluoro-1-methyl-2-oxo-5-phenyl-2,3-dihydro-1H-1,4-benzodiazepin-3-yl)-2,3-bis(3,3,3-trifluoropropyl) succinamide | 575 | 10.317 [b] |
| 9 | H | OCH$_3$ | (2R,3S)-N-((3S)-7-methoxy-1-methyl-2-oxo-5-phenyl-2,3-dihydro-1H-1,4-benzodiazepin-3-yl)-2,3-bis(3,3,3-trifluoropropyl)succinamide | 587 | 15.92 [a] |
| 10 | H | F | (2R,3S)-N-((3S)-7-fluoro-1-methyl-2-oxo-5-phenyl-2,3-dihydro-1H-1,4-benzodiazepin-3-yl)-2,3-bis(3,3,3-trifluoropropyl) succinamide | 575 | 16.15 [a] |
| 11 | Cl | H | (2R,3S)-N-((3S)-8-chloro-1-methyl-2-oxo-5-phenyl-2,3-dihydro-1H-1,4-benzodiazepin-3-yl)-2,3-bis(3,3,3-trifluoropropyl) succinamide | 591 | 17.58 [a] |

[a] Xbridge Phenyl (4.6 × 150 mm), 3.5 micron; 1 mL/min flow rate; gradient 10-100% B over 30 min (A: 0.05% TFA in water/CH$_3$CN (95:5), B: 0.05% TFA in water/CH$_3$CN (5:95) @ 220 and 250 nm); 30 min run.

[b] Xbridge Phenyl (4.6 × 150 mm), 3.5 micron; 1 mL/min flow rate; gradient 10-100% B over 15 min (A: 0.05% TFA in water/CH$_3$CN (95:5), B: 0.05% TFA in water/CH$_3$CN (5:95) @ 220 and 250 nm); 15 min run.

Examples 12 to 18

The compounds listed below were prepared according to the general synthetic procedure described in Example 1, using the appropriate benzodiazepinone obtained by methods known to one skilled in the art, for example, Carter, M. C. et al., *J. Med. Chem.*, 49:2311-2319 (2006).

TABLE 7

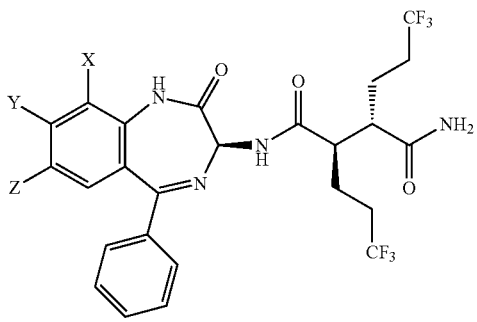

| Ex. No. | X | Y | Z | Compound Name | [M + H]⁺ | HPLC Ret Time (min) |
|---|---|---|---|---|---|---|
| 12 | OCH₃ | H | H | (2R,3S)-N-((3S)-9-methoxy-2-oxo-5-phenyl-2,3-dihydro-1H-1,4-benzodiazepin-3-yl)-2,3-bis(3,3,3-trifluoropropyl)succinamide | 573 | 14.741 $^a$ |
| 13 | H | OCH₃ | H | (2R,3S)-N-((3S)-8-methoxy-2-oxo-5-phenyl-2,3-dihydro-1H-1,4-benzodiazepin-3-yl)-2,3-bis(3,3,3-trifluoropropyl)succinamide | [M − H] = 571 | 9.38 $^b$ |
| 14 | H | H | OCH₃ | (2R,3S)-N-((3S)-7-methoxy-2-oxo-5-phenyl-2,3-dihydro-1H-1,4-benzodiazepin-3-yl)-2,3-bis(3,3,3-trifluoropropyl)succinamide | [M − H] = 571 | 9.14 $^b$ |
| 15 | OCH₃ | CN | H | (2R,3S)-N-((3S)-8-cyano-9-methoxy-2-oxo-5-phenyl-2,3-dihydro-1H-1,4-benzodiazepin-3-yl)-2,3-bis(3,3,3-trifluoropropyl)succinamide | 598 | 0.95 $^c$ |
| 16 | Cl | Cl | H | (2R,3S)-N-((3S)-8,9-dichloro-2-oxo-5-phenyl-2,3-dihydro-1H-1,4-benzodiazepin-3-yl)-2,3-bis(3,3,3-trifluoropropyl)succinamide | 611 | 2.095 $^d$ |
| 17 | F | H | H | (2R,3S)-N-((3S)-9-fluoro-2-oxo-5-phenyl-2,3-dihydro-1H-1,4-benzodiazepin-3-yl)-2,3-bis(3,3,3-trifluoropropyl)succinamide | 561 | 2.698 $^e$ |
| 18 | Cl | H | H | (2R,3S)-N-((3S)-9-chloro-2-oxo-5-phenyl-2,3-dihydro-1H-1,4-benzodiazepin-3-yl)-2,3-bis(3,3,3-trifluoropropyl)succinamide | 577 | 1.982 $^d$ |

$^a$ Xbridge Phenyl (4.6 × 150 mm), 3.5 micron; 1 mL/min flow rate; gradient 10-100% B over 12 min (A: 0.05% TFA in water/CH₃CN (95:5), B: 0.05% TFA in water/CH₃CN (5:95) @ 220 and 250 nm); 25 min run.
$^b$ Xbridge Phenyl (4.6 × 150 mm), 3.5 micron; 1 mL/min flow rate; gradient 10-100% B over 12 min (A: 0.05% TFA in water/CH₃CN (95:5), B: 0.05% TFA in water/CH₃CN (5:95) @ 220 and 250 nm); 15 min run.
$^c$ LCMS: MeOH/H₂O/0.1% TFA, BEH C18 2.1 × 50 mm 1.7 u, 2 min gradient, wavelength = 254 nm.
$^d$ MeOH/H₂O/0.1% TFA, Waters Sunfire C₁₈ 2.1 × 30 mm, 2 min gradient, wavelength = 254 nm.
$^e$ CHROMOLITH ® ODS 4.6 × 50 mm (4 min grad) eluting with 10-90% aqueous MeOH over 4 minutes containing 0.% TFA, 4 mL/min, monitoring at 220 nm.

Example 19

(2R,3S)—N-((3S)-2-Oxo-5-phenyl-2,3-dihydro-1H-1,4-benzodiazepin-3-yl)-3-(4,4,4-trifluorobutyl)-2-(3,3,3-trifluoropropyl)succinamide

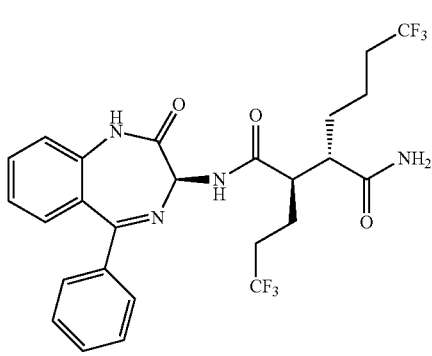

(19)

Preparation 19A: (2R,3R)-3-(tert-Butoxycarbonyl)-7,7,7-trifluoro-2-(3,3,3-trifluoropropyl)heptanoic acid

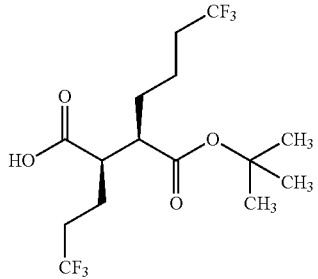

(19A)

Preparation 19A was prepared from Preparation 9A (674 mg, 2.59 mmol) and Preparation 1P (500 mg, 1.850 mmol) according to the alternate procedure shown for Preparation 1E. Obtained Preparation 19A (521 mg, 28%): MS (ES): m/z=379 [M−H]⁻.

Preparation 19B: (2R,3S)-3-(tert-Butoxycarbonyl)-7,7,7-trifluoro-2-(3,3,3-trifluoropropyl)heptanoic acid

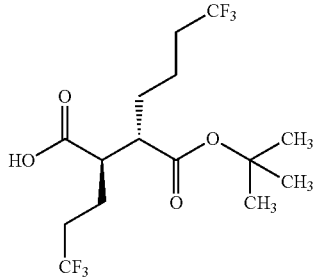

(19B)

Preparation 19B was prepared from Preparation 19A (198 mg, 0.521 mmol) according to the general procedure shown to enrich the mixture of Preparation 1E and Preparation 1F. Obtained Preparation 19B (192 mg, 98%): MS (ES): m/z=379 [M−H]⁻; ¹H NMR (500 MHz, CDCl₃) δ ppm 2.65-2.72 (1H, m), 2.60 (1H, ddd, J=10.33, 8.81, 3.61 Hz), 2.19-2.30 (2H, m), 2.06-2.16 (3H, m), 1.85-1.96 (1H, m), 1.70-1.81 (2H, m), 1.51-1.67 (3H, m), 1.47 (7H, s).

Preparation 19C: tert-Butyl (2S,3R)-6,6,6-trifluoro-3-(((3S)-2-oxo-5-phenyl-2,3-dihydro-1H-1,4-benzodiazepin-3-yl)carbamoyl)-2-(4,4,4-trifluorobutyl)hexanoate

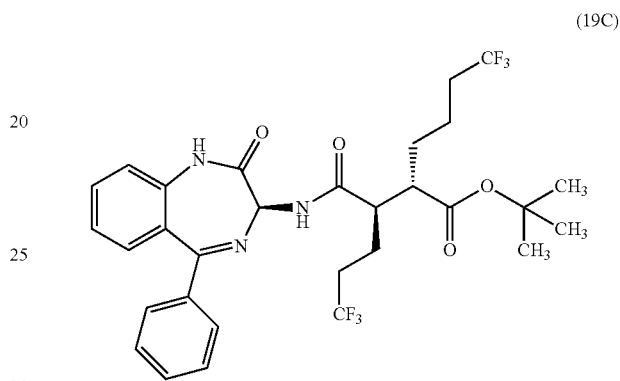

(19C)

Preparation 19C was prepared from Preparation 19B (45.4 mg, 0.119 mmol) and Preparation 2A (30 mg, 0.119 mmol) according to the general procedure shown for Preparation 1I. Obtained Preparation 19C (82 mg, 100%): HPLC: RT=3.475 min (CHROMOLITH® 5 u C18 4.6×30 mm (4 min grad) eluting with 10-90% aqueous MeOH over 4 minutes containing 0.1% TFA, monitoring at 220 nm); MS (ES): m/z=614 [M+H]⁺.

Preparation 19D: (2S,3R)-6,6,6-Trifluoro-3-(((3S)-2-oxo-5-phenyl-2,3-dihydro-1H-1,4-benzodiazepin-3-yl)carbamoyl)-2-(4,4,4-trifluorobutyl)hexanoic acid

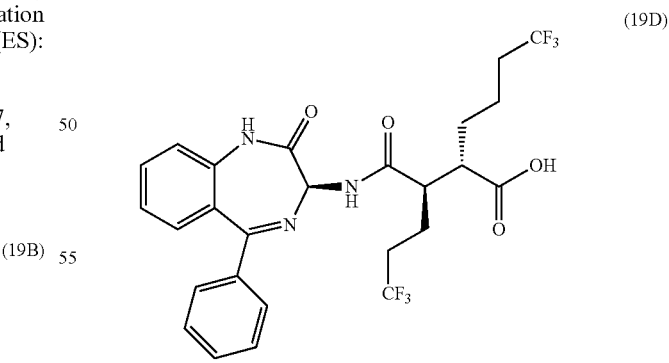

(19D)

Preparation 19D was prepared from Preparation 19C (73 mg, 0.119 mmol) according to the general procedure shown for Preparation 1K. Obtained Preparation 19D (80 mg, 100%) as a TFA solvate: HPLC: RT=2.926 min (CHROMOLITH® 5 u C18 4.6×30 mm (4 min grad) eluting with 10-90% aqueous MeOH over 4 minutes containing 0.1% TFA, monitoring at 220 nm).

Example 19

Example 19 was prepared from Preparation 19D (80 mg, 0.119 mmol) according to the general procedure shown for Example 1. After separation of the diastereoisomers, Example 19 (35 mg, 49%) was obtained. HPLC: RT=2.731 min (CHROMOLITH® 5 u C18 4.6×30 mm (4 min grad) eluting with 10-90% aqueous MeOH over 4 minutes containing 0.1% TFA, monitoring at 220 nm); MS (ES): m/z=557 [M+H]$^+$; $^1$H NMR (500 MHz, DMSO-d$_6$) δ ppm 10.82 (1H, s), 9.42 (1H, d, J=7.21 Hz), 7.65 (1H, ddd, J=8.32, 7.07, 1.53 Hz), 7.60 (1H, d, J=2.22 Hz), 7.49-7.57 (3H, m), 7.42-7.49 (2H, m), 7.29-7.35 (2H, m), 7.20-7.28 (1H, m), 7.03 (1H, s), 5.23 (1H, d, J=7.21 Hz), 2.70-2.79 (1H, m), 2.57-2.69 (1H, m), 2.39-2.47 (1H, m), 2.05-2.32 (3H, m), 1.50-1.67 (3H, m), 1.40-1.49 (1H, m), 1.24-1.39 (2H, m).

Example 20

(2R,3S)—N1-((3S)-8-Methoxy-2-oxo-5-phenyl-2,3-dihydro-1H-1,4-benzodiazepin-3-yl)-3-(4,4,4-trifluorobutyl)-2-(3,3,3-trifluoropropyl)succinamide (20)

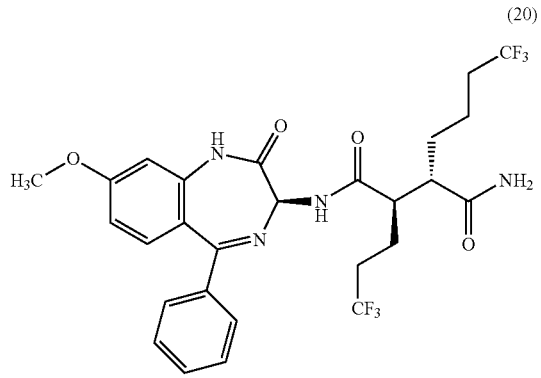 [SMILES: COc1ccc2c(c1)NC(=O)[C@@H](NC(=O)[C@H](CCC(F)(F)F)[C@H](CCCC(F)(F)F)C(N)=O)N=C2c1ccccc1]

Example 20 was prepared by using a sequence of reactions as outlined for Example 19 using Preparation 19B instead of Preparation 1E. The mixture of diastereoisomers obtained was separated via chiral HPLC to provide Example 20. HPLC RT=0.89 min. (BEH C18 2.1×50 mm, 1.7 u, 0 to 100 B in 1 min with 0.5 min hold time, Flow rate=1 ml/min, detection at 254 nm, Solvent A: 100% water/0.1% TFA; Solvent B: 100% ACN1/0.1% TFA). MS (ES): m/z=587.2 [M+H]$^+$.

Example 21

(2R,3S)—N-((3S)-9-((2-Methoxyethyl)amino)-2-oxo-5-phenyl-2,3-dihydro-1H-1,4-benzodiazepin-3-yl)-2,3-bis(3,3,3-trifluoropropyl)succinamide (21)

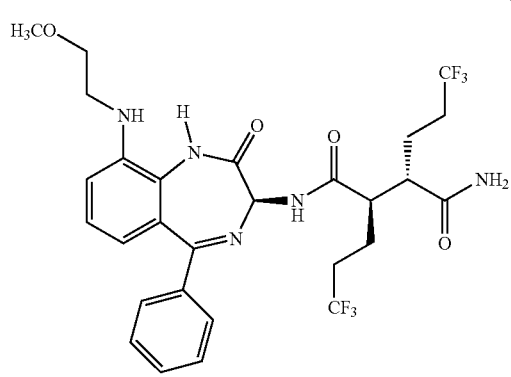

Preparation 21A: (3-((4-Methoxybenzyl)(2-methoxyethyl)amino)-2-nitrophenyl)(phenyl)methanone

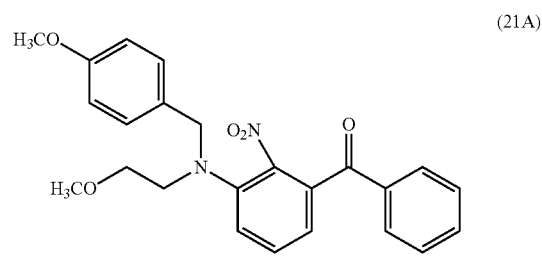 [SMILES: COCCN(Cc1ccc(OC)cc1)c1cccc(C(=O)c2ccccc2)c1[N+](=O)[O-]]

(21A)

A mixture of (3-chloro-2-nitrophenyl)(phenyl)methanone (850 mg, 3.25 mmol) and 2-methoxy-N-(4-methoxybenzyl)ethanamine (3171 mg, 16.24 mmol) was heated at 100° C. for 16 hours. The reaction mixture was partitioned between water (50 mL) and DCM (50 mL), extracted with DCM (3×50 mL), dried over Na$_2$SO$_4$, and purified using silica gel chromatography (stepwise gradient: 30 to 50% ethyl acetate/hexanes) to isolate Preparation 21A (780 mg, 57.1% yield) as a brown oil: LC/MS (PHENOMENEX® Luna 5 micron C18 4.6×30 mm, 0 to 100 B in 2 min with 1 min hold time, Flow rate=5 ml/min, detection at 254 nm, Solvent A: 10% methanol/90% water/0.1% TFA; Solvent B: 10% water/90% methanol/0.1% TFA) RT=2.32; MS (ES) m/z=443.10 [M+Na]$^+$.

Preparation 21B: (2-Amino-3-((4-methoxybenzyl)(2-methoxyethyl)amino)phenyl)(phenyl)methanone

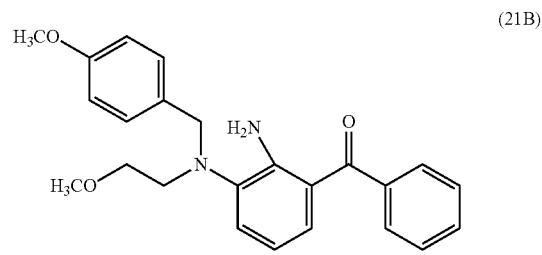 [SMILES: COCCN(Cc1ccc(OC)cc1)c1cccc(C(=O)c2ccccc2)c1N]

(21B)

Preparation 21A (700 mg, 1.665 mmol), zinc (1089 mg, 16.65 mmol), and ammonium chloride (891 mg, 16.65 mmol) in EtOH (40 mL) and water (20 mL) was heated to 90° C. for 5 minutes. The reaction mixture was filtered through CELITE®, partitioned between water/DCM, extracted 3×10 mL DCM, dried over Na$_2$SO$_4$, and concentrated to isolate Preparation 21B (580 mg, 89% yield): LC/MS (PHENOMENEX® Luna 5 micron C18 4.6×30 mm, 30 to 100 B in 4 min with 1 min hold time, Flow rate=5 ml/min, detection at 254 nm, Solvent A: 10% methanol/90% water/0.1% TFA; Solvent B: 10% water/90% methanol/0.1% TFA): RT=2.47 min; MS (ES): m/z=391.16 [M+H]$^+$.

Preparation 21C: Benzyl 9-((4-methoxybenzyl)(2-methoxyethyl)amino)-2-oxo-5-phenyl-2,3-dihydro-1H-benzo[e][1,4]diazepin-3-ylcarbamate (21C)

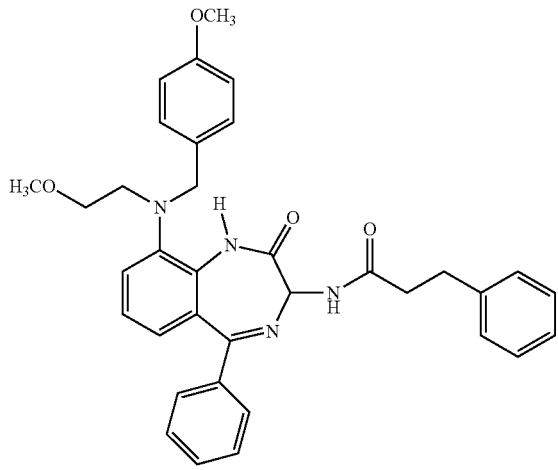

Preparation 21C was prepared from Preparation 21B following the general procedure for Preparation 50D (38.6% yield): LC/MS (PHENOMENEX® Luna 5 micron C18 4.6× 30 mm, 30 to 100 B in 4 min with 1 min hold time, Flow rate=5 ml/min, detection at 254 nm, Solvent A: 10% methanol/90% water/0.1% TFA; Solvent B: 10% water/90% methanol/0.1% TFA) RT=2.42 min; MS (ES): m/z=579.22 [M+H]$^+$.

Example 21

Example 21 was prepared from Preparation 21C by using the general sequence of reactions as outlined for Example 1. The mixture of diastereoisomers obtained was separated via chiral HPLC to provide Example 21: LC/MS (PHENOMENEX® Luna 5 micron C18 4.6×30 mm, 30 to 100 B in 4 min with 1 min hold time, Flow rate=5 ml/min, detection at 254 nm, Solvent A: 10% methanol/90% water/0.1% TFA; Solvent B: 10% water/90% methanol/0.1% TFA) RT=2.13 min; MS (ES): m/z=616.22 [M+H]$^+$.

Comparative Compounds 22 to 25

Comparative Compounds 22 to 25 can be prepared according to the procedures described in U.S. Pat. No. 7,053,084 for Examples 8, 12a, 38, and 45a, respectively.

| Comparative Compound | U.S. Pat. No. 7,053,084 | Structure |
|---|---|---|
| 22 | Ex. 8 | 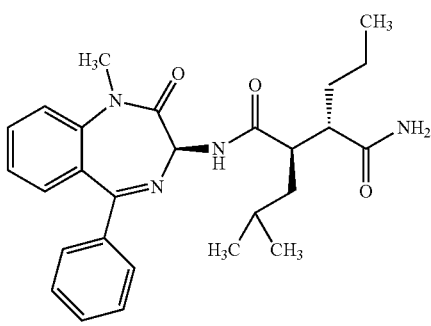 [SMILES: CCC[C@H](C(N)=O)[C@@H](CC(C)C)C(=O)N[C@H]1N=C(c2ccccc2)c2ccccc2N(C)C1=O] |
| 23 | Ex. 12a | 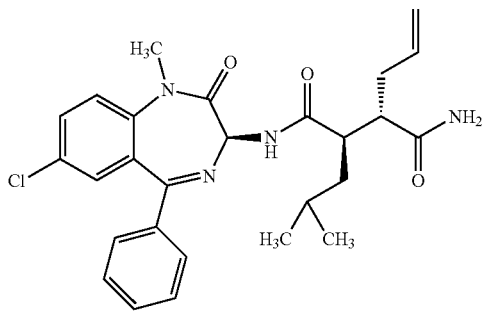 [SMILES: C=CC[C@H](C(N)=O)[C@@H](CC(C)C)C(=O)N[C@H]1N=C(c2ccccc2)c2cc(Cl)ccc2N(C)C1=O] |

-continued

| Comparative Compound | U.S. Pat. No. 7,053,084 | Structure |
|---|---|---|
| 24 | Ex. 38 | 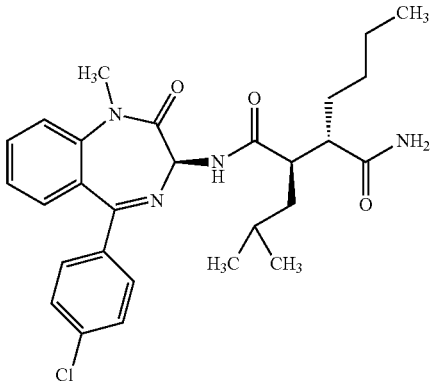 [SMILES: CCCC[C@H](C(N)=O)[C@@H](CC(C)C)C(=O)N[C@H]1N=C(c2ccc(Cl)cc2)c2ccccc2N(C)C1=O] |
| 25 | Ex. 45a | 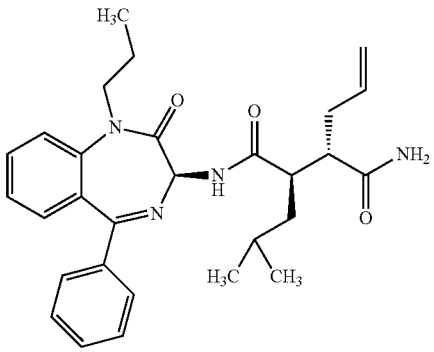 [SMILES: C=CC[C@H](C(N)=O)[C@@H](CC(C)C)C(=O)N[C@H]1N=C(c2ccccc2)c2ccccc2N(CCC)C1=O] |

Example 26

Pharmaceutical Formulation Comprising (2R,3S)—N-((3S)-1-Methyl-2-oxo-5-phenyl-2,3-dihydro-1H-1,4-benzodiazepin-3-yl)-2,3-bis(3,3,3-trifluoropropyl)succinamide An injection drug product was formulated comprising 2R,3S)—N-((3S)-1-methyl-2-oxo-5-phenyl-2,3-dihydro-1H-1,4-benzodiazepin-3-yl)-2,3-bis(3,3,3-trifluoropropyl) succinamide, Example 1, as a single-use, ready-to-use (RTU) sterile solution for intravenous (IV) administration using 50:50 (v/v) combinations of purified polyoxyethylated castor oil (a surfactant) and dehydrated alcohol (a solvent). The drug product was a clear to slightly hazy (opalescent), colorless to pale yellow sterile solution, stored in 5-mL Type I flint glass vials, closed with 20-mm stoppers, and sealed with 20-mm aluminum seals. The concentrated formulation can be diluted prior to administration with commonly used intravenous diluents, such as Normal Saline (NS) or 5% Dextrose, to provide a physiologically acceptable diluted product.

TABLE 11

Concentrated Pharmaceutical Composition

| Component | | Quantity (mg/mL) |
|---|---|---|
| Example 1 | active pharmaceutical ingredient | 1.2 |
| Purified Polyoxyethylated Castor Oil | solubilizer | 0.5 |
| Dehydrated Alcohol | solvent | 0.5 |

Purified Polyoxyethylated Castor Oil: CREMOPHOR (BASF Corp.)

The concentrated pharmaceutical formulation was found to be stable upon storage at 25° C./60% relative humidity, 40° C./75% relative humidity, and 50° C. for a period of three months. Also, a photo-stability study (HIL/UVA) indicated that the product did not need to be protected from light. The concentrated formulation of Example 1 had long-term shelf stability including chemical and physical stability.

Prior to IV administration, the concentrated pharmaceutical formulation was diluted with Normal Saline (NS) or 5% Dextrose in Water (D5W) to concentrations between 0.01 mg/mL and 0.06 mg/mL. The use-time/compatibility results indicated that the product diluted in NS or D5W to concentrations in the range from 0.01 mg/mL to 0.06 mg/mL was compatible with non-PVC, non-DEHP IV infusion bags. The results showed essentially no changes through 24 hours of storage at 2° C. to 8° C. or room temperature/room light (25° C. and approximately 5000 lux).

BIOLOGICAL ASSAYS

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pcDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask ($4.5 \times 10^6$ cells/flask) using the Monster Transfection Kit (Minis #MIR2906) according to manufacturers specifications. Table 12 denotes respective DNA quantity for the transfections.

TABLE 12

|  | DNA (µg) | CBF1 (µg) | Vector (µg) | Total DNA (µg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of $5 \times 10^3$ cells/well in 95 µl, assay media (DMEM (high glucose with HEPES), 1× glutamine/penicillin/streptomycin, 0.0125% BSA, 1× non-essential amino acids). Assay media (5 mL) containing test compounds in final concentrations ranging from 5 µM to $8.4 \times 10^{-5}$ µM (3 fold serial dilutions) were added to the cells and the cell plates were then incubated for 18 hours at 37° C. and 5% $CO_2$. Control wells contained DMSO vehicle (total counts) or 0.5 µM of an in-house small molecule inhibitor (background counts). Duplicates were used for each sample. Luciferase activity was measured after a 20-minute incubation with 50 µl STEADY-GLO® luciferase reagents according to manufacturer's specifications (Promega, Cat. #: E2550) and analyzed by Envision plate reader (PerkinElmer, Boston, Mass.).

The antagonist effect of compounds was expressed as 100× [1−(average sample−average background)/(average total−average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 13 below lists the Notch 1 and Notch 3 $IC_{50}$ values for Examples 1 to 21 of this invention and Comparative Compounds 22 to 25 measured in the Notch-CBF1 Transactivation Assay hereinabove. The results in Table 13 were rounded to 2 digits. The compounds of the present invention, as exemplified by the Examples 1 to 21 showed Notch 1 values of 6.6 nM or less and Notch 3 $IC_{50}$ values of 13 nM or less.

TABLE 13

| Example | Notch 1 ($IC_{50}$, nM) | Notch 3 ($IC_{50}$, nM) |
|---|---|---|
| 1 | 1.6 | 3.4 |
| 2 | 1.7 | 3.3 |
| 3 | 3.1 | 4.7 |
| 4 | 1.5 | 2.5 |
| 5 | 1.2 | 5.9 |
| 6 | 6.5 | 10 |
| 7 | 1.5 | 2.8 |
| 8 | 4.9 | 8.1 |
| 9 | 4.4 | 8.2 |

TABLE 13-continued

| Example | Notch 1 ($IC_{50}$, nM) | Notch 3 ($IC_{50}$, nM) |
|---|---|---|
| 10 | 2.9 | 4.6 |
| 11 | 1.3 | 2.0 |
| 12 | 2.5 | 4.2 |
| 13 | 2.1 | 3.8 |
| 14 | 5.2 | 13 |
| 15 | 12 | 16 |
| 16 | 4.2 | 6.4 |
| 17 | 3.6 | 7.1 |
| 18 | 0.53 | 2.3 |
| 19 | 1.3 | 3.8 |
| 20 | 2.9 | 4.2 |
| 21 | 1.5 | 4.2 |
| Comparative Compound 22 | 64 | 48 |
| Comparative Compound 23 | 42 | 75 |
| Comparative Compound 24 | 5.1 | 13 |
| Comparative Compound 25 | 12 | 12 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining). In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 14.

TABLE 14

Metabolic Stability - Result Interpretation Guidelines

| CYP-Mediated Clearance | Percent Remaining after 10 minutes | | | | |
|---|---|---|---|---|---|
|  | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Table 15 below lists the CYP-mediated metabolic stability for Examples 1 to 21 of this invention and Comparative Compounds 22 to 25 measured in the human and mouse metabolic stability assays. The results in Table 15 were rounded to 2 digits. In the liver microsome assays, a value of 0% remaining indicated complete CYP-mediated metabolism of a test compound, and a value of 100% indicated no detectable CYP-mediated metabolism of a test compound. The compounds of the present invention, as exemplified by Examples 1 to 21 had metabolic stability values of 80% or greater remaining for human liver microsomes (HLM) and 72% or greater remaining for mouse liver microsomes (MsLM). In contrast, Comparative Compounds 22 to 25 had metabolic stability values of 39% or less remaining for human liver microsomes and 15% or less remaining for mouse liver microsomes.

TABLE 15

| Example | 0.5 µM HLM (% Remaining) | 0.5 µM MsLM (% Remaining) |
|---|---|---|
| 1 | 97 | 91 |
| 2 | 88 | 86 |
| 3 | 84 | 91 |
| 4 | 100 | 91 |
| 5 | 100 | 98 |
| 6 | 100 | 100 |
| 7 | 93 | 72 |
| 8 | 96 | 100 |
| 9 | 100 | 87 |
| 10 | 96 | 98 |
| 11 | 97 | 98 |
| 12 | 100 | 100 |
| 13 | 100 | 97 |
| 14 | 100 | 95 |
| 15 | 100 | 93 |
| 16 | 80 | 91 |
| 17 | 100 | 96 |
| 18 | 100 | 100 |
| 19 | 96 | 97 |
| 20 | 100 | 100 |
| 21 | 98 | 82 |
| Comparative Compound 22 | 39 | 15 |
| Comparative Compound 23 | 19 | 9.0 |
| Comparative Compound 24 | 21 | 13 |
| Comparative Compound 25 | 2.7 | 0.18 |

The compounds of the present invention (Examples 1 to 21) have been compared to the Comparative Compounds 22 to 25 disclosed in U.S. Pat. No. 7,456,172, and have been found to be especially advantageous. The compounds of the present invention had the surprising advantage of the combination of activity as inhibitors of Notch 1 and Notch 3 and superior metabolic stability to liver microsomes. As shown in Tables 13 and 15, in the reported tests, Examples 1 to 21 of this invention had Notch 1 $IC_{50}$ values of 6.6 nM or less and Notch 3 $IC_{50}$ values of 13 nM or less; and metabolic stability values of 80% or greater remaining for human liver microsomes (HLM) and 72% or greater remaining for mouse liver microsomes (MsLM). In contrast, in similar tests, the Comparative Compounds 22 to 25 had Notch 1 $IC_{50}$ values of 5.1 nM or greater and Notch 3 $IC_{50}$ values of 13 nM or greater; and metabolic stability values of 39% or less remaining for human liver microsomes and 15% or less remaining for mouse liver microsomes.

Methods and Materials

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 µl of liver microsome suspension, protein concentration of 1.1 mg/ml in 100 mM $NaP_i$, pH 7.4, 5 mM $MgCl_2$ buffer, was pre-warmed at 37° C.

2. 1.7 µl of 50 µM compound (98.6% ACN, 1.4% DMSO) was added to the same tube and pre-incubated at 37° C. for 5 minutes.

3. The reaction was initiated by the addition of 17 µl of pre-warmed 10 mM NADPH solution in 100 mM $NaP_i$, pH 7.4.

The reaction components were mixed well, and 75 µl of the reaction mixture was immediately transferred into 150 µl quench/stop solution (zero-time point, $T_0$). Reactions were incubated at 37° C. for 10 minutes and then an additional 75 µl aliquot was transferred into 150 µl quench solution. Acetonitrile containing 100 µM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for UV-LC/MS-MS analysis to determine the percent of parent compound that remained in the mixture.

TABLE 16

Metabolic Stability Assay - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0 minutes and 10 minutes |
| Quench/Stop Solution (ACN + 100 µM DMN) | 150 µl |
| Sample of Reaction | 75 µl |
| Sedimentation of Denatured Microsomes | 15 minutes |
| UV-LC/MS analysis of supernatant | 0.17 µM |

Sample Analysis—Instrumentation

HPLC: Pump—Thermo Surveyor; Autosampler—CTC/LEAP HTS; UV detector—Thermo Surveyor PDA plus; Column—Varian C18, 3 µm, 2×20 mm with a 0.5 µm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer Thermo TSQ Quantum Ultra triple-quadrapole mass spectrometer;

Sample Analysis Structural Integrity Pre-Analysis.

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-$H_2O$.

The resulting solutions (200 μM) were analyzed for structural integrity by LC-UV/MS on a Thermo LCQ Deca XP Plus ion trap mass spectrometer, using a Waters XBridge C18, 5 μm, 2×50 mm column with a Waters Sentry 2.1 mm guard column, and the LC conditions described in the table below, with a 5 μl injection and a flow rate of 1 ml/min. The acquired data reflected purity by UV absorbance at 220 nm. Only results for those compounds with purity greater than 50% were reported.

TABLE 17

Metabolic Stability - Structural Integrity Gradient

| Gradient Time (min) | A % | B % |
| --- | --- | --- |
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ Quantum triple-quadrapole mass spectrometer equipped with a heated-electrospray (H-ESI) source by automated infusion to obtain the SRM transitions and their corresponding collision energy values. Compound solutions at a concentration of 20 μM in 1:1 methanol:water were infused at a flow rate of 90 μL/min, then combined with the mobile phase at a flow rate of 50 μL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a Microsoft Access database.

The mass spectrometric conditions obtained from automated infusion were used to analyze incubation samples from the Metabolic Stability assay. The injection volume was 5 μl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 18

Metabolic Stability - Sample Analysis Gradient

| Gradient Time (min) | A % (or C %) | B % (or D %) |
| --- | --- | --- |
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the $T_{10minute}$ samples to those from the $T_{10minute}$ samples for each compound.

Quality Control

A set of three compounds was tested along with the test compound in each assay plate. Data was accepted and uploaded only if the results for these control compounds fall into the expected ranges shown below.

TABLE 19

Metabolic Stability Assay - Control Compound Values by Microsome Species

| | Average Percent Remaining ± SD | | | | |
| --- | --- | --- | --- | --- | --- |
| Compound | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al., *J. Pharmacol. Exp. Ther.*, 283:46-58 (1997); Obach, *Drug Metab. Dispos.*, 27:1350-1359 (1999)).

The metabolic stability half-life assay panel evaluates the time-course and the rate of CYP-mediated (NADPH-dependent) metabolism in vitro in human, rat, mouse, dog and monkey microsomes. The time course spans a 45 minute incubation, and includes 0, 5, 10, 15, 30, and 45 minute time-points, at each of which the amount of test compound remaining in the mixture was measured.

Result Interpretation Guideline

The results of these assays were expressed as a half-life ($T_{1/2}$, min), and the fraction of parent compound remaining in the reaction mixture at each time-point (Percent Remaining) was also reported. In general, these results should be used to evaluate only the extent of CYP-mediated, or NADPH-dependent, metabolism of the test compound. When the compound was significantly metabolized ($T_{1/2}$<8-14 min), this indicated high clearance in vivo due to CYP-mediated metabolism. However, if the compound demonstrated moderate (50-80%) or low (>85%) metabolism in these in vitro assays, high clearance was still possible in vivo via other metabolism and elimination pathways.

The results of these assays was predictive of compound clearance in vivo, assuming that CYP-mediated metabolism was a predominant elimination pathway. In different microsomal species, the ranges of results were approximately as shown in the following table:

TABLE 20

Metabolic Stability Half-Life - Result Interpretation Guidelines

| CYP-Mediated Clearance | $T_{1/2}$, minutes | | | | |
|---|---|---|---|---|---|
| | Human | Rat | Mouse | Dog | Monkey |
| Low | >70 | >40 | >50 | >65 | >40 |
| Medium | 14-70 | 8-40 | 10-50 | 12-65 | 8-40 |
| High | <14 | <8 | <10 | <12 | <8 |

Methods and Materials

Liver microsomes were purchased from BD-Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 μM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 μl of liver microsome suspension, protein concentration of 1.1 mg/ml in 100 mM NaP$_i$, pH 7.4, 5 mM MgCl$_2$ buffer, was pre-warmed at 37° C.

2. 5 μl of 50 μM compound (98.6% ACN, 1.4% DMSO) was added to the same tube and pre-incubated at 37° C. for 5 minutes.

3. The reaction was initiated by the addition of 50 μl of pre-warmed 10 mM NADPH solution in 100 mM NaP$_i$, pH 7.4.

Reaction components were mixed well, and 65 μl were immediately transferred into 130 μl quench/stop solution (zero-time point, T$_0$). Reactions were incubated at 37° C. for 5, 10, 15, 30 and 45 minutes and at each time-point a 65 μl aliquot was transferred into 130 μl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 μl of supernatant extract, containing the mixture of parent compound and its metabolites, was then transferred to a separate 96-well plate for LC/MS-MS analysis to determine the percent of parent compound that was remaining in the mixture.

TABLE 21

Metabolic Stability Half-Life Assays - Reaction Components

| Reaction Components | Final Concentration in the Metabolic Stability Assay |
|---|---|
| Compound (Substrate) | 0.5 μM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| MgCl$_2$ | 5.0 mM |
| 37° C. Incubation time | 0, 5, 10, 15, 30, and 45 minutes |
| Quench/Stop Solution (ACN + 100 μM DMN) | 130 μl |
| Sample of Reaction | 65 μl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

The exemplified compounds of the invention showed the surprising advantage of low clearance due to CYP-mediated metabolism in both the human (HLM) and mouse (MsLM) metabolic stability assays. The compounds of the present invention, as exemplified by Examples 1-2, 5-7, 9-14, 16, 18, 21-23, and 26, had percent remaining values in the range of 60% to 100% for the human liver microsome assay, and 25% to 100% for the mouse liver microsome assay. In contrast, Comparative Compounds 60-61 had percent remaining values of 7.0% or less in both the human and mouse liver microsome assays. Comparative Compounds 61-62 showed high clearance in both the human and mouse metabolic stability assays, indicating that the compounds were removed by CYP-mediated metabolism in the liver.

Human Tumor Xenograft Models in Mice

All rodents were obtained from Harlan Sprague Dawley Co. (Indianapolis, Ind.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromized balb/c nu/nu nude or NOD-SCID mice (Harlan Sprague Dawley). Tumors were propagated as subcutaneous transplants in the appropriate mouse strain (Table 22) using tumor fragments obtained from donor mice.

TABLE 22

Histological Types and Host Mouse Strain/Gender Requirement for the Propagation of Various Human Tumor Xenografts in Mice

| Tumor Type | Histology | Mouse Strain | Sex |
|---|---|---|---|
| TALL-1 | ALL | NOD-SCID | female |
| HPB-ALL | ALL | NOD-SCID | female |
| ALL-SIL | ALL | NOD-SCID | female |
| MDA-MB-157 | breast | NOD-SCID | female |
| MDA-MB-468 | breast | NOD-SCID | female |
| PAT-34 | ovarian | nude | female |
| PAT-50 | ovarian | nude | female |
| PAT-26 | pancreas | nude | female |
| PAT-27 | pancreas | nude | female |

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups, with the exception of experiments conducted in the SAL-IGF (this is not included in Table 22) tumor model, in which there were typically 5 mice per treatment and control group. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

Tumor weight=(length×width$^2$)÷2

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e., TGI≥50%) for a period equivalent to at least 1 tumor volume doubling time and drug treatment must be for a period equivalent to at least 2 tumor volume doubling time.

Tumor response was also expressed in terms of tumor growth delay (TGD value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e., more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at $P<0.05$.

Drug Administration

In in vitro studies, all agents were dissolved in 100% DMSO and serially diluted in media/10% fetal bovine serum. For administration of Notch inhibitors to rodents, two different excipients were used: [1] 94% Labrafil/5% ETOH/1% TW80 or [2] ETOH/TPGS/PEG300 (10:10:80). Notch inhibitors were typically administered orally on a schedule of QD×15, 10 day-on-2 day-off, although other schedules had also been evaluated and shown to be efficacious. For example, dosing regimen consisting of QD×12, 4 day-on-3 day-off was shown to be equally efficacious as QD×15, 10 day-on-2 day-off.

In Vivo Antitumor Activity

Figure 6:
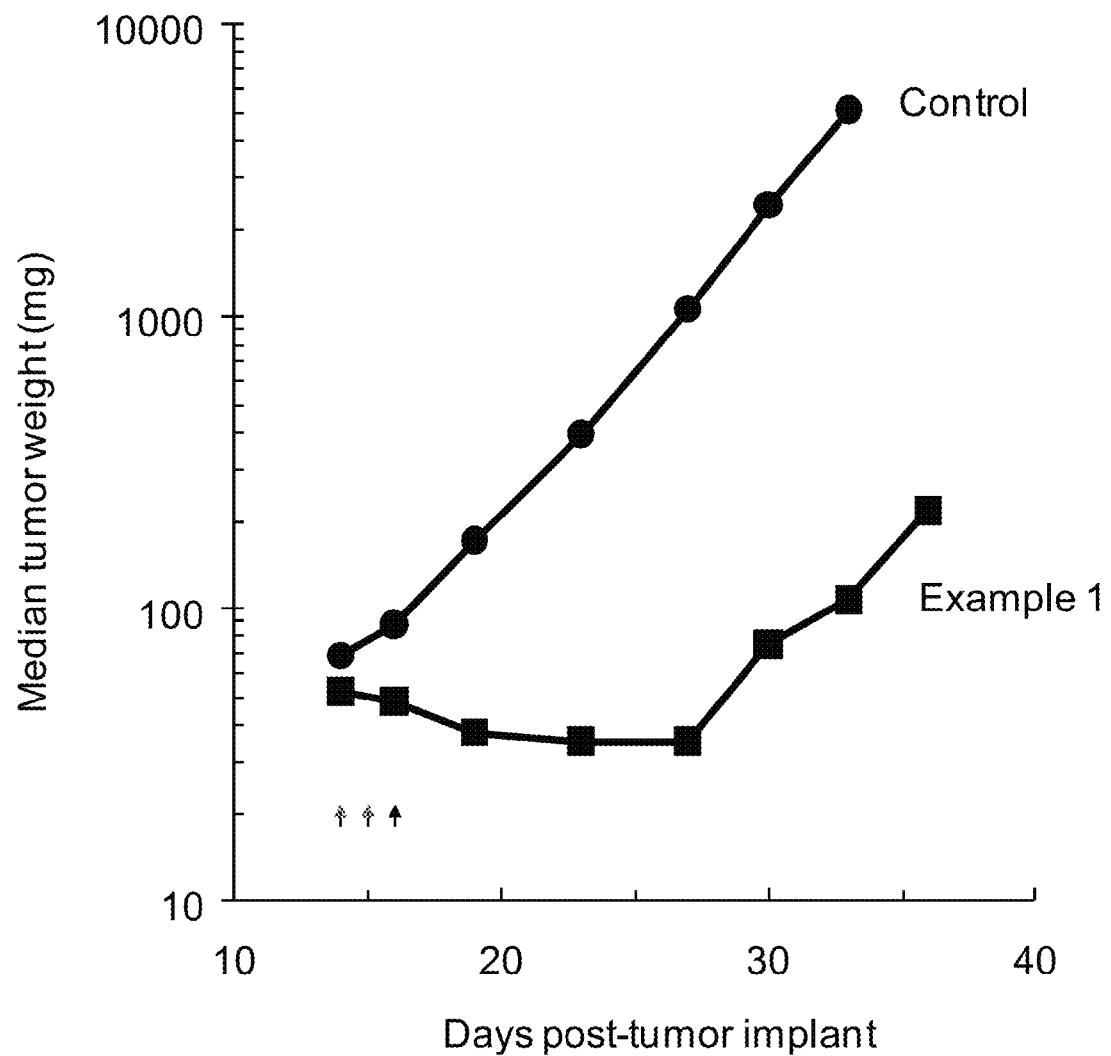
FIG. 6 shows the antitumor efficacy of Example 1 against TALL1 Human T-cell acute lymphoblastic leukemia. Each symbol represents the median tumor burden of a group of 8 mice. (●) Control; (■) Example 1, 5 mg/kg/adm, QD×3, IV.

The antitumor activity of Example 1 administered via the intravenous route (IV) was evaluated in human tumor xenografts implanted in mice. As shown in FIG. 6, Example 1 exhibited antitumor activity.

Table 23 below lists the antitumor activity of examples of this invention measured in the Human Tumor Xenograft Models in mice. The compounds of the present invention, as exemplified by Examples 1 and 2, showed antitumor activity with oral administration (PO).

TABLE 23

Schedule: QDx15, 10 Day-on-2 Day-off; Oral Administration

| | | Antitumor Activity | | |
|---|---|---|---|---|
| Example | Dose (mg/kg) | TALL1 (LCK) | MDA-MB-157 (% TGI) | MDA-MB-468 (% TGI) |
| 1 | 7.5-10 | >4.7 | 89 | 78 |
| 2 | 24 | 2.4 | 85 | 87 |

QD - once daily
LCK—Log Cell Kill

Example 1 demonstrates broad-spectrum antineoplastic activity against a wide array of human cancer xenografts grown in mice. Significant antitumor activity was demonstrated in 16 human cancer xenografts, including human T-cell acute lymphoblastic leukemia, breast carcinoma, pancreatic carcinoma, ovarian carcinoma, glioblastoma, non-small cell lung carcinoma, colon carcinoma, osteogenic sarcoma, and neuroblastoma (Table 24).

TABLE 24

| Tumor | Histology | Antitumor Activity (% TGI)$^a$ |
|---|---|---|
| TALL1 | T-Cell acute lymphoblastic leukemia | 112 |
| Pat-24 | pancreatic cancer | 111 |
| BT-474 | HER2+ breast cancer | 96 |
| Pat-26 | pancreatic cancer | 93 |
| MDA-MB468 | TN breast cancer | 91 |
| Pat-50 | ovarian cancer | 91 |
| Pat-34 | ovarian cancer | 89 |
| U-87 | glioblastoma multiforme (GBM) | 82 |
| MDA-MB157 | TN breast cancer | 81 |
| Calu-6 | Non small cell lung cancer | 81 |
| HCT116 | colon cancer | 75 |

TABLE 24-continued

| Tumor | Histology | Antitumor Activity (% TGI)[a] |
|---|---|---|
| G292 | osteogenic sarcoma | 75 |
| Pat-21/Abx R | TN breast cancer (abx R) | 73 |
| MCF7 | estrogen-dependent breast cancer | 73 |
| SK-N-AS | neuroblastoma | 67 |
| MCF7i | estrogen-independent breast cancer | 63 |

[a]All treatments were PO, QDx15, 10 day-on-2 day-off, at dosages ranging from 5-10 mg/kg/adm.

Combination Chemotherapy

A series of studies were conducted to evaluate the combinability of Example 1 with a number of anti-cancer agents including dasatinib, paclitaxel, Tamoxifen, dexamethasone, and carboplatin

I. Example 1 and Dasatinib

Figure 7:
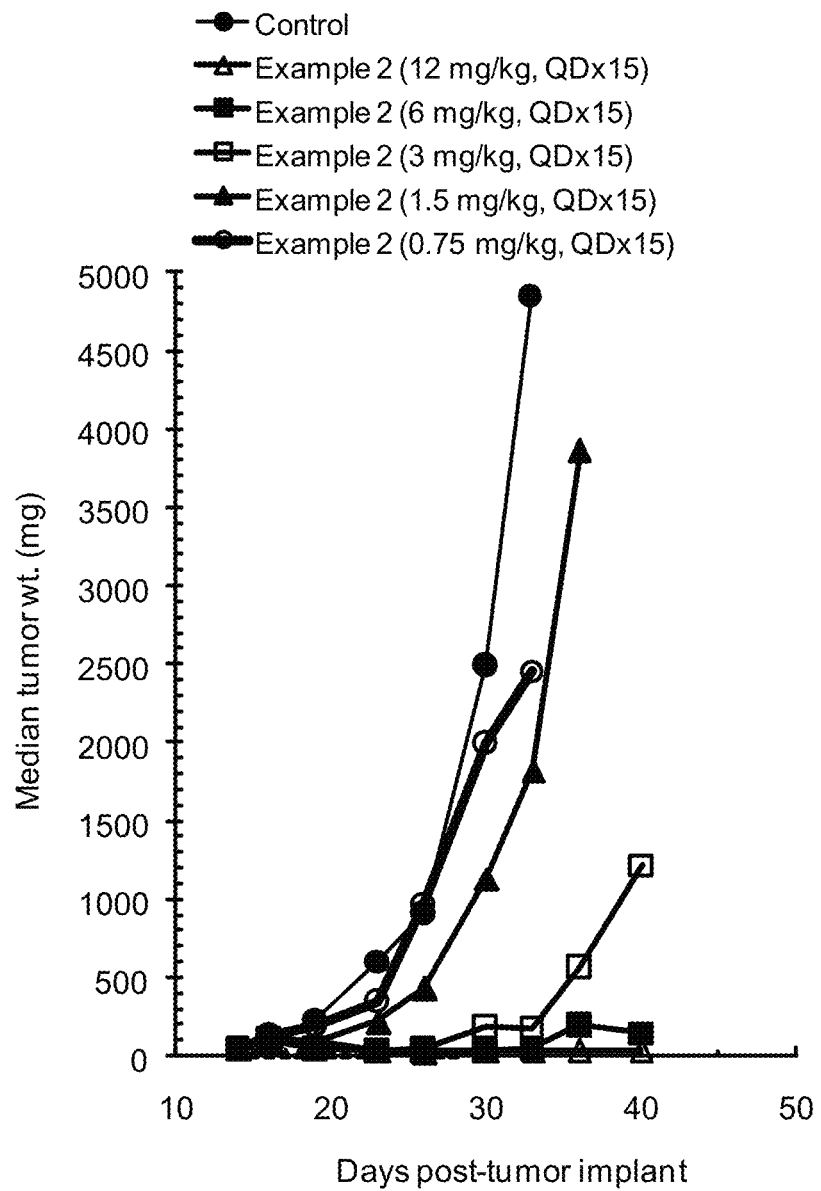
FIG. 7 shows the in vivo antitumor activity of Example 2 in T-cell acute lymphoblastic leukemia cell line TALL1. Each symbol represents the median tumor burden of a group of 8 mice. (●) control; (Δ) Example 2, 12 mg/kg, QD×15; (■) Example 2, 6 mg/kg, QD×15; ( ) Example 2, 3 mg/kg, QD×15; (▲) Example 2, 1.5 mg/kg, QD×15; (○) Example 2, 0.75 mg/kg, QD×15.

The human T-cell lymphoblastic leukemia was used to evaluate the combined efficacy Example 1 and dasatinib. Dasatinib treatment alone produced an antitumor effect of 1.7 LCK (10 mg/kg/adm, QD×49, PO). Example 1 compound produced only modest activity of 0.1-0.5 LCK at dose range of 3.75-7.5 mg/kg. However, combination of the two agents produced synergistic antitumor activity, yielding antitumor efficacy of >>2.6 LCK that was significantly superior to dasatinib single agent alone (P<0.05). In addition, the combination regimen yielded complete response (CR) in 100% of mice, whereas none of the single agent produced CR (FIGS. 7-8 and Table 25).

TABLE 25

Antitumor Efficacy by Combined Chemotherapy with Example 1 and Dasatinib in ALL-SIL T-cell Lymphoblastic Leukemia

| Treatment | | Efficacy | | | | |
|---|---|---|---|---|---|---|
| Example 1 Dose[a] (mg/kg) | Dasatinib Dose[b] (mg/kg) | Tumor Growth Delay[c] | | PR (%) | CR (%) | P |
| | | (LCK) | (days) | | | |
| 7.5 | — | 0.1 | 1.9 | 0 | 0 | — |
| 3.75 | — | 0.5 | 8.7 | 0 | 0 | — |
| — | 10 | 1.7 | 30.2 | 0 | 0 | 1 |
| 7.5 | 10 | >>2.6 | 44 | 0 | 100 | <0.05 |
| 3.75 | 10 | >>2.6 | 44 | 0 | 100 | <0.05 |

[a]Regimen = PO, QD x3, weekly x7
[b]Regimen = PO, QD x49
[c]Target tumor size = 1000 mg

II. Example 1 and Paclitaxel

The antitumor efficacy of Example 1 in combination with paclitaxel was evaluated in the MDA-MB-468 breast carcinoma. Example 1 as a single agent produced 0.5-1.4 LCK at the dose range of 3.75-7.5 mg/kg/adm. Paclitaxel administered weekly at a dose of 12 mg/kg/adm yielded 0.5 LCK (FIGS. 9-10 and Table 26). The combination of Example 1 at the dose-range of 3.75-7.5 mg/kg/adm and paclitaxel produced 3.4-4.1 LCK of antitumor effects which was significantly superior to single agent Example 1 compound alone (P=0.0006 and 0.0002, respectively).

TABLE 26

Antitumor Efficacy by Combined Chemotherapy with Example 1 and Paclitaxel in MDA-MB-468 Human Breast Carcinoma

| Treatment | | Efficacy | | | | |
|---|---|---|---|---|---|---|
| Example 1 Dose[a] (mg/kg) | Paclitaxel Dose[b] (mg/kg) | Tumor Growth Delay[c] | | PR (%) | CR (%) | P |
| | | (LCK) | (days) | | | |
| 7.5 | — | 1.4 | 21.2 | 0 | 0 | 1 |
| 3.75 | — | 0.5 | 7.8 | 0 | 0 | — |
| — | 12 | 0.5 | 7.8 | 0 | 0 | — |
| 7.5 | 12 | 4.1 | 61.8 | 50 | 0 | 0.0002 |
| 3.75 | 12 | 3.4 | 51.2 | 0 | 0 | 0.0006 |

[a]Regimen = PO, QD x3, weekly x7
[b]Regimen = IV, Q7D x6
[c]Target tumor size = 500 mg

III. Example 1 and Tamoxifen

The antitumor efficacy of Example 1 in combination with Tamoxifen was evaluated in the ER receptor positive human breast carcinoma xenograft MCF7 grown in female nu/nu mice. Example 1 as a single agent produced tumor growth inhibition (TGI) of 43-58% at the dose range of 3.75-7.5 mg/kg/adm with no CR or PR. Tamoxifen, administered at the MTD dose of 20 mg/kg/adm, IP, Q2 DX12, produced % TGI of 78%, with no CR or PR. The combinations of Example 1 compound and Tamoxifen were clearly synergistic producing % TGI of 101 and 99, respectively, at Example 1 doses of 7.5 and 3.75 mg/kg/adm. Moreover, approximately 50% of mice receiving the combinations experienced tumor shrinkage, either as PR or CR (FIGS. 11-12 and Table 27).

TABLE 27

Antitumor Efficacy by Combined Chemotherapy with Example 1 and Tamoxifen in the MCR7 Human Breast Carcinoma

| Treatment | | Efficacy | | | |
|---|---|---|---|---|---|
| Example 1 Dose[a] (mg/kg) | Tamoxifen Dose[b] (mg/kg) | Tumor Growth Inhibition TGI[c] | PR (%) | CR (%) | P |
| 7.5 | — | 58 | 0 | 0 | 0 |
| 3.75 | — | 43 | 0 | 0 | — |
| — | 20 | 78 | 0 | 0 | 1 |
| 7.5 | 20 | 101 | 43 | 0 | 0.0012 |
| 3.75 | 20 | 99 | 43 | 14 | 0.0087 |

[a]Regimen = PO, QD x3, weekly x3
[b]Regimen = IP, Q2D x10
[c]Target tumor size = 500 mg

IV. Example 1 and Dexamethasone

The antitumor efficacy of Example 1 in combination with the glucocorticoid, dexamethasone, was evaluated in the human T-ALL leukemia xenografts HPB-ALL grown in NOD-SCID mice. Example 1 as a single agent was active in this model yielding 1.1 LCK at 7.5 mpk. Dexamethasone was modestly active as a single agent producing 0.7 LCK at its MTD of 7.5 mpk. The combination of Example 1 and dexamethasone produced 1.9 LCK, significantly superior to either individual single agents alone (FIG. 13 and Table 28).

TABLE 28

Antitumor Efficacy by Combined Chemotherapy with Example 1 and Dexamethasone in HPB-ALL Human Acute Lymphoblastic Leukemia

| Treatment | | Efficacy | | | | |
|---|---|---|---|---|---|---|
| Example 1 Dose[a] | Dexamethasone Dose[b] | Tumor Growth Delay[c] | | PR | | |
| (mg/kg) | (mg/kg) | (LCK) | (days) | (%) | CR (%) | P |
| 7.5 | — | 1.1 | 9.5 | 0 | 0 | 0.0007 |
| 3.75 | — | 0.9 | 7.8 | 0 | 0 | 0.0007 |
| — | 7.5 | 0.7 | 5.8 | 0 | 0 | 0.0007 |
| — | 3.75 | 0.6 | 5.6 | 0 | 0 | 0.0007 |
| 3.75 | 7.5 | 1.9 | 16.5 | 0 | 0 | 1 |

[a]Regimen = PO, QD x3, weekly x3
[b]Regimen = IP, QD x14
[c]Target tumor size = 3000 mg V. Example 1 and Carboplatin The antitumor efficacy of Example 1 in combination with carboplatin was evaluated in the human ovarian teratocarcinoma xenograft PA-1 grown in female nu/nu mice. Example 1 as a single agent produced 0.2 LCK at the dose of 1 mg/kg/adm. Carboplatin administered weekly at a dose of 90 mg/kg/adm yielded 2.1 LCK (FIG. 14 and Table 29). The combination of Example 1 at the dose of 1 mg/kg/adm and carboplatin produced >3.1 LCK of antitumor effects which was significantly superior to single agent Example 1 compound alone (P=0.004).

TABLE 29

Antitumor Efficacy by Combined Chemotherapy with Example 1 and Carboplatin in PA-1 Human Ovarian Teratocarcinoma

| Treatment | | Efficacy | | | | | |
|---|---|---|---|---|---|---|---|
| Example 1 Dose[a] | Dexamethasone Dose[b] | Tumor Growth Delay[c] | | CR | PR | Cure | |
| (mg/kg) | (mg/kg) | (LCK) | (days) | (%) | (%) | (%) | P |
| 1 | — | 0.2 | 4 | 0 | 0 | 0 | |
| — | 90 | 2.1 | 34.7 | 13 | 71 | 13 | 1 |
| 1 | 90 | >3.1 | >51.4 | 67 | 33 | 67 | 0.004 |

[a]Regimen = PO, QD x21 (1 mg/kg)
[b]Regimen = IV, Q7D x3
[c]Target tumor size = 500 mg Single Crystal X-Ray Diffractometry The single crystal data were collected on a Bruker-AXS APEX2 CCD system using Cu Kα radiation (λ=1.5418 Å). Indexing and processing of the measured intensity data were carried out with the APEX2 software program suite. When indicated, crystals were cooled in the cold stream of an Oxford cryo system during data collection. The structures were solved by the direct methods and refined on the basis of observed reflections using the SHELXTL. The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Typically, all the non-H atoms were refined anisotropically and all H-atoms other than those attached to N and O atoms were calculated by geometrical methods and refined using a riding model.

X-Ray Powder Diffractometry

X-ray powder diffraction (PXRD) data were obtained using a Bruker GADDS (General Area Detector Diffraction System) manual chi platform goniometer. Powder samples were placed in thin walled glass capillaries of 0.7 mm in diameter; the capillaries were rotated during data collection. The sample-to-detector distance was kept at 17 cm. Data were collected with Cu Kα radiation (λ=1.5418 Å) in the range 2.5<2θ<35° with a sample exposure time of 600 seconds.

What is claimed is:

1. A compound of Formula (I):

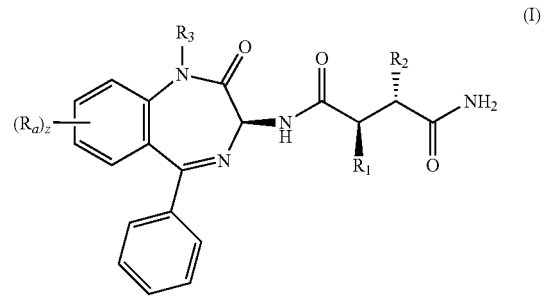

(I)

wherein:
R$_1$ is —CH$_2$CF$_3$ or —CH$_2$CH$_2$CF$_3$;
R$_2$ is —CH$_2$CF$_3$, —CH$_2$CH$_2$CF$_3$, or —CH$_2$CH$_2$CH$_2$CF$_3$;
R$_3$ is H or —CH$_3$;
each R$_a$ is independently F, Cl, —CN, —OCH$_3$, and/or —NHCH$_2$CH$_2$OCH$_3$; and
z is 1 or 2.

2. The compound according to claim 1 wherein:
R$_2$ is —CH$_2$CF$_3$ or —CH$_2$CH$_2$CF$_3$.

3. The compound according to claim 1 wherein:
z is 1.

4. The compound according to claim 3 selected from: (2R,3S)—N-((3S)-7-chloro-1-methyl-2-oxo-5-phenyl-2,3-dihydro-1H-1,4-benzodiazepin-3-yl)-2,3-bis(3,3,3-trifluoropropyl)succinamide (6); (2R,3S)—N-((3S)-8-methoxy-1-methyl-2-oxo-5-phenyl-2,3-dihydro-1H-1,4-benzodiazepin-3-yl)-2,3-bis(3,3,3-trifluoropropyl)succinamide (7); (2R,3S)—N-((3S)-8-fluoro-1-methyl-2-oxo-5-phenyl-2,3-dihydro-1H-1,4-benzodiazepin-3-yl)-2,3-bis(3,3,3-trifluoropropyl)succinamide (8); (2R,3S)—N-((3S)-7-methoxy-1-methyl-2-oxo-5-phenyl-2,3-dihydro-1H-1,4-benzodiazepin-3-yl)-2,3-bis(3,3,3-trifluoropropyl)succinamide (9); (2R,3S)—N-((3S)-7-fluoro-1-methyl-2-oxo-5-phenyl-2,3-dihydro-1H-1,4-benzodiazepin-3-yl)-2,3-bis(3,3,3-trifluoropropyl)succinamide (10); (2R,3S)—N-((3S)-8-chloro-1-methyl-2-oxo-5-phenyl-2,3-dihydro-1H-1,4-benzodiazepin-3-yl)-2,3-bis(3,3,3-trifluoropropyl)succinamide (11); (2R,3S)—N-((3S)-9-methoxy-2-oxo-5-phenyl-2,3-dihydro-1H-1,4-benzodiazepin-3-yl)-2,3-bis(3,3,3-trifluoropropyl)succinamide (12); (2R,3S)—N-((3S)-8-methoxy-2-oxo-5-phenyl-2,3-dihydro-1H-1,4-benzodiazepin-3-yl)-2,3-bis(3,3,3-trifluoropropyl)succinamide (13); (2R,3S)—N-((3S)-7-methoxy-2-oxo-5-phenyl-2,3-dihydro-1H-1,4-benzodiazepin-3-yl)-2,3-bis(3,3,3-trifluoropropyl)succinamide (14); (2R,3S)—N-((3S)-9-fluoro-2-oxo-5-phenyl-2,3-dihydro-1H-1,4-benzodiazepin-3-yl)-2,3-bis(3,3,3-trifluoropropyl)succinamide (17); and (2R,3S)—N-((3S)-9-chloro-2-oxo-5-phenyl-2,3-dihydro-1H-1,4-benzodiazepin-3-yl)-2,3-bis(3,3,3-trifluoropropyl)succinamide (18).

5. The compound according to claim 1 wherein:
z is 2.

6. The compound according to claim 5 selected from: (2R,3S)—N-((3S)-8-cyano-9-methoxy-2-oxo-5-phenyl-2,3-dihydro-1H-1,4-benzodiazepin-3-yl)-2,3-bis(3,3,3-trifluoropropyl)succinamide (15); and (2R,3S)—N-((3S)-8,9-dichloro-2-oxo-5-phenyl-2,3-dihydro-1H-1,4-benzodiazepin-3-yl)-2,3-bis(3,3,3-trifluoropropyl)succinamide (16).

* * * * *

UNITED STATES PATENT AND TRADEMARK OFFICE
CERTIFICATE OF CORRECTION

PATENT NO. : 8,822,454 B2
APPLICATION NO. : 14/100896
DATED : September 2, 2014
INVENTOR(S) : Ashvinikumar Gavai et al.

Page 1 of 1

It is certified that error appears in the above-identified patent and that said Letters Patent is hereby corrected as shown below:

Title Page, References Cited:

Page 2, Col. 2, line 12, (Other Publications)
Delete "Salzberg," and insert -- Salzburg, --, Page 2, Col. 2, line 28, (Other Publications)
Delete "Salzberg," and insert -- Salzburg, --, In the Claims:

Claim 4, col. 93, lines 2-3, delete "trifluoropropyl) succinamide" and insert
-- trifluoropropyl)succinamide --.

Signed and Sealed this
Twelfth Day of May, 2015

Michelle K. Lee
*Director of the United States Patent and Trademark Office*